US008835611B2

(12) United States Patent
Kunz et al.

(10) Patent No.: US 8,835,611 B2
(45) Date of Patent: *Sep. 16, 2014

(54) CALICHEAMICIN DERIVATIVE-CARRIER CONJUGATES

(75) Inventors: Arthur Kunz, New City, NY (US); Justin Keith Moran, Valley Cottage, NY (US); Joseph Thomas Rubino, Towace, NJ (US); Neera Jain, New City, NY (US); Eugene Joseph Vidunas, Middletown, NY (US); John McLean Simpson, Upper Nyack, NY (US); Paul David Robbins, Upper Nyack, NY (US); Nishith Merchant, Palisades Park, NJ (US); John Francis Dijoseph, Woodbridge, NJ (US); Mark Edward Ruppen, Garnerville, NY (US); Nitin Krishnaji Damle, Upper Saddle River, NJ (US); Andrew George Popplewell, Middlesex (GB)

(73) Assignee: Wyeth Holdings LLC, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/372,172

(22) Filed: Feb. 13, 2012

(65) Prior Publication Data

US 2012/0213804 A1 Aug. 23, 2012

Related U.S. Application Data

(63) Continuation of application No. 10/428,894, filed on May 2, 2003, now Pat. No. 8,153,768.

(60) Provisional application No. 60/377,440, filed on May 2, 2002.

(51) Int. Cl.
*C07K 16/00* (2006.01)
*A61K 47/48* (2006.01)

(52) U.S. Cl.
CPC ..... *A61K 47/48384* (2013.01); *A61K 47/48407* (2013.01); *A61K 47/48561* (2013.01)
USPC .................. 530/391.7; 530/391.1; 530/391.9

(58) Field of Classification Search
USPC ................... 530/391.1, 391.7, 391.9
See application file for complete search history.

(56) References Cited

U.S. PATENT DOCUMENTS

| | | |
|---|---|---|
| 5,134,075 A | 7/1992 | Hellstrom et al. |
| 5,225,539 A | 7/1993 | Winter |
| 5,382,510 A | 1/1995 | Levine |
| 5,436,265 A | 7/1995 | Black |
| 5,530,101 A | 6/1996 | Queen |
| 5,558,864 A | 9/1996 | Bendig |
| 5,686,072 A | 11/1997 | Uhr et al. |
| 5,693,762 A | 12/1997 | Queen |
| 5,712,374 A | 1/1998 | Kuntsmann et al. |
| 5,714,350 A | 2/1998 | Co |
| 5,714,586 A | 2/1998 | Kunstmann |
| 5,789,554 A | 8/1998 | Leung |
| 6,180,377 B1 | 1/2001 | Morgan |
| 6,183,477 B1 | 2/2001 | Pepper |
| 6,183,744 B1 | 2/2001 | Goldenberg |
| 6,267,958 B1 | 7/2001 | Andya et al. |
| 6,777,390 B1 | 8/2004 | Matthiessen |
| 7,012,135 B2 | 3/2006 | Athwal |
| 7,115,723 B1 | 10/2006 | Hong |
| 7,129,053 B1 | 10/2006 | Reiter |
| 7,147,851 B1 | 12/2006 | Ponath |
| 7,355,011 B2 | 4/2008 | Popplewell et al. |
| 7,541,034 B1 | 6/2009 | Fitzgerald |
| 7,910,103 B2 | 3/2011 | Goldenberg |
| 7,939,073 B2 | 5/2011 | Goldenberg |
| 8,153,768 B2 * | 4/2012 | Kunz et al. .................. 530/391.1 |
| 2002/0141990 A1 | 10/2002 | Deen |
| 2004/0082764 A1 | 4/2004 | Kunz et al. |
| 2005/0095238 A1 | 5/2005 | Brettman |
| 2006/0073137 A1 | 4/2006 | Adair |
| 2007/0172920 A1 | 7/2007 | Leung |

FOREIGN PATENT DOCUMENTS

| | | |
|---|---|---|
| EP | 0263526 | 4/1988 |
| JP | 11-508232 | 7/1999 |
| JP | 2001-128691 | 5/2001 |
| JP | 2001-518930 | 10/2001 |
| WO | WO 91/09967 | 7/1991 |
| WO | WO 92/00311 | 1/1992 |
| WO | WO 96/04925 | 2/1996 |
| WO | WO 96/05306 | 2/1996 |
| WO | WO 98/41641 | 2/1996 |

(Continued)

OTHER PUBLICATIONS

Teagarden et al. (European Journal of Pharmaceutical Sciences, Mar. 2002, 15: 115-133).*
PubMed publication of Teagarden et al (Eur J Pharm Sci. Mar. 2002;15(2):115-33).*
Bendig, Mary M.; "Humanization of Rodent Monoclonal Antibodies by CDR Grafting" *Methods*: A Companion to Methods in Enzymology; vol. 8, pp. 83-93, 1995.
Benhar et al., "Mutations of two lysine residues in the CDR loops of a recombinant immunotoxin that reduce its sensitivity to chemical derivatization," *Bioconjugate Chem.*, 1994, 5: 321-326.
Browning et al., "B cells move to centre stage: novel opportunities for autoimmune disease treatment," *Nat. Rev. Drug Discov.*, 2006, 5: 564-576.
Carnahan et al., "Epratuzumab, a humanized nomoclonal antibody targeting CD22: characterization of in vitro properties," *Clinical Cancer Res.*, 2003, 9, suppl.: 3982s-3990s.

(Continued)

*Primary Examiner* — Mark Halvorson
*Assistant Examiner* — Yan Xiao
(74) *Attorney, Agent, or Firm* — Womble Carlyle Sandridge & Rice, LLP

(57) ABSTRACT

Methods for preparing monomeric cytotoxic drug/carrier conjugates with a drug loading significantly higher than in previously reported procedures and with decreased aggregation and low conjugate fraction (LCF) are described. Cytotoxic drug derivative/antibody conjugates, compositions comprising the conjugates and uses of the conjugates are also described. Monomeric calicheamicin derivative/anti-CD22 antibody conjugates, compositions comprising the conjugates and uses of the conjugates are also described.

40 Claims, 35 Drawing Sheets

(56) References Cited

FOREIGN PATENT DOCUMENTS

| WO | WO 96/40261 | 12/1996 |
|----|-------------|---------|
| WO | WO 98/42378 | 10/1998 |
| WO | WO 98/56418 | 12/1998 |
| WO | WO 99/66031 | 12/1999 |
| WO | WO 00/74718 | 12/2000 |

OTHER PUBLICATIONS

DiJoseph et al., "Antibody-targeted chemotherapy of B-cell lymphoma using calicheamicin conjugated to murine or humanized antibody against CD22," *Cancer Immunol. Immunother.*, 2005, 54: 11-24.
DiJoseph et al., "Antibody-targeted chemotherapy with CMC-544: a CD22-targed immunoconjugte of calicheamicin for the treatment of B-lymphoid malignancies," *Blood*, 2004, 103: 1807-1814.
Ghetie et al, "The Antitumor Activity of an Anti-CD22 Immunotoxin in SCID Mice With Disseminated Daudi Lymphoma is Enhanced by Either an Anti-CD19 Antibody or an Anti-CD19 Immunotixin" *Blood* 1992:80(9): 2315-2320.
Gura et al "Systems for Identifying New Drugs Are Often Faulty", *Science* 1997; 278: 1041-1042.
Güssow et al, "Humanization of Monoclonal Antibodies" *Methods in Enzymology*, (1991)203:99-121.
Hamann et al., "An Anti-MUC1 Antibody-Calicheamicin Conjugate for Treatment of Solid Tumors. Choice of Linker and Overcoming Drug Resistance" *Bioconjugate Chem.* 2005, 16, 346-353.
Hamann et al., "An anti-CD33 antibody-calicheamicin conjugate for treatment of acute myeloid leukemia. Choice of linker.", Bioconjug. Chem., 2002, 13:40-46.
Hinman et al., "Preparation and characterization of monoclonal antibody conjugates of the calicheamicins: a novel and potent family of antitumor antibiotics," Cancer Res., 1993, 53:3336-3342.
Jendreyko et al., "Antitumour activity of Calicheamicin theta, Doxorubicin and anti-CD19 immunoconjugates in a human pre-B ALL cell line," Blood, 2001, 98: 105a (Abstract #440).
Kashmiri et al, "SDR grafting—a new approach to antibody hmanization", *Methods* 2005, 36:25-34.
Leung et al., "Construction and characterization of a humanized, internalizing, B-cell (CD22)-specific, leukemia/lymphoma antibody, LL2," *Mol. Immunol.*, 1995, 32: 1413-1427.
Leung et al., "Effect of Vk framework-1 glycosylation on the binding affinity of lymphoma-specific murine and chimeric LL2 antibodies and its potential use as a novel conjugation site," *Intl. J. Cancer.*, 1995, 60: 534-538.
Low et al, "Mimicking Somatic Hypermutation: Affinity Maturation of Antibodies Displayed on Bacteriohage Using a Bacterial Mutator Strain", *J. Mol. Biol* (1996) 260, 359-368.

Maloney et al, "IDEC-C2B8 (Rituximab) Anti-CD20 Monoclonal Antibody Therapy in Patients with Relapsed Low-Grade Grade Non-Hodgkin's Lymphoma" *Blood* 1997; 90(6): 2188-2195.
Newton et al, "Potent and specific antitumor effects of an anti-CD22-targeted cytotoxic ribonuclease: potential for the treatment of non-Hodgkin lymphoma" *Blood* 2001; 97(2): 528-535.
Paul: "Fv Structure and Diversity in Three Dimensions" Fundamental Immunology, 3rd Ed.: pp. 292-295, 1993.
Press et al, "Immunotherapy of Non-Hodgkin's Lymphomas" *Hematology Am Soc Hematol Educ Program*, 2001:22-40.
Riechmann et al., "Reshaping human antibodies for therapy," *Nature*, 1988, 332:323-327.
Rudikoff et al, *Proc. Natl. Acad. Sci. USA*, vol. 79, pp. 1979-1983, Mar. 1982.
Saijo et al, "What are the reasons for negative phase III trials of molecular-target-based drugs?" *Cancer Sci.* 2004; 95(10): 772-776.
Siegel et al., "Calicheamicin derivatives conjugated to monoclonal antibodies: determination of loading values and distributions by infrared and UV matrix-assisted laser desorption/ionization mass spectrometry and electrospray ionization mass spectrometry," Anal. Chem., 1997, 69: 2716-2726.
Trail et al "Monoclonal antibody drug conjugates in the treatment of cancer " Current Opinion in Immunology 1999, 11:584-588.
Tsai et al, "Progressive Intermediate-Grade Non-Hodgkin's Lymphoma After High-Dose Therapy and Autologous Peripheral Stem-Cell Transplantation: Changing the Natural History with Monoclonal Antibody Therapy", *Clinical Lymphoma*. Jun. 2000: 1(1):62-66).
Van Rossenberg et al., "A structure-function study of ligand recognition by CD22 beta," *J. Bio. Chem.*, 2001, 276: 12967-12973.
Vaughan et al., "Human antibodies by design," *Nature Biotech*. 1998, 16: 535-539.
Verhoeyen et al., "Reshaping human antibodies: Grafting an antilysozyme activity," *Science*, 1988, 239:1534-1536.
Vose, J.M., "Therapeutic uses of MAbs directed against CD20" *Cytotherapy*, 2000, 2:455-461.
Wu et al, "Humanization of a Murine Monoclonal Antibody by Simulaneous Optimization of Framework and CDR Residues" *J. Mol. Biol*. (1999)294, 151-162.
Yelton et al, "Affinity maturation of BR96 anti-carcinoma antibody by condon-based mutagenesis.", *The Journal of Immunology*, 1995, vol. 155 pp. 1994-2004.
ISR dated Dec. 10, 2003 issued in corresponding International Application No. PCT/US2003/013910.
DiJoseph et al, "CMC-544 (inotuzumab ozogamicin): A CD22-targeted immunoconjugate of calicheamicin", *Hematology Meeting Reports* (2008) 5(6):74-77.

* cited by examiner

FIGURE 1: SEQUENCE OF CDRS OF MOUSE MONOCLONAL 5/44

| | | |
|---|---|---|
| H1 | NYWIH | (SEQ ID NO:1) |
| H2 | GINPGNNYTTYKRNLKG | (SEQ ID NO:2) |
| H3 | EGYGNYGAWFAY | (SEQ ID NO:3) |
| L1 | RSSQSLANSYGNTFLS | (SEQ ID NO:4) |
| L2 | GISNRFS | (SEQ ID NO:5) |
| L3 | LQGTHQPYT | (SEQ ID NO:6) |

FIGURE 2: DNA/PROTEIN SEQUENCE OF 5/44 V$_L$

```
            10              20              30              40              50
   GAT GTT GTG GTG ACT CAA ACT CCA CTC TCC CTG CCT GTC AGC TTT GGA GAT CAA GTT
   CTA CAA CAC CAC TGA GTT TGA GGT GAG AGG GAC GGA CAG TCG AAA CCT CTA GTT CAA
    D   V   V   V   T   Q   T   P   L   S   L   P   V   S   F   G   D   Q   V>

60              70              80              90             100             110
   TCT ATC TCT TGC AGG TCT AGT CAG AGT CTT GCA AAC AGT TAT GGG AAC ACC TTT TTG
   AGA TAG AGA ACG TCC AGA TCA GTC TCA GAA CGT TTG TCA ATA CCC TTG TGG AAA AAC
    S   I   S   C   R   S   S   Q   S   L   A   N   S   Y   G   N   T   F   L>

120             130             140             150             160             170
   TCT TGG TAC CTG CAC AAG CCT GGC CAG TCT CCA CAG CTC CTC ATC TAT GGG ATT TCC
   AGA ACC ATG GAC GTG TTC GGA CCG GTC AGA GGT GTC GAG GAG TAG ATA CCC TAA AGG
    S   W   Y   L   H   K   P   G   Q   S   P   Q   L   L   I   Y   G   I   S>

180             190             200             210             220
   AAC AGA TTT TCT GGG GTG CCA GAC AGG TTC ACT GGC AGT GGT TCA GGG ACA GAT TTC
   TTG TCT AAA AGA CCC CAC GGT CTG TCC AAG TGA CCG TCA CCA AGT CCC TGT CTA AAG
    N   R   F   S   G   V   P   D   R   F   T   G   S   G   S   G   T   D   F>

230             240             250             260             270             280
   ACA CTC AAG ATC AGC ACA ATA AAG CCT GAG GAC TTG GGA ATG TAT TAC TGC TTA CAA
   TGT GAG TTC TAG TCG TGT TAT TTC GGA CTC CTG AAC CCT TAC ATA ATG ACG AAT GTT
    T   L   K   I   S   T   I   K   P   E   D   L   G   M   Y   Y   C   L   Q>

290             300             310             320             330
   GGT ACA CAT CAG CCG TAC ACG TTC GGA GGG GGG ACC AAG CTG GAA ATA AAA CGT
   CCA TGT GTA GTC GGC ATG TGC AAG CCT CCC CCC TGG TTC GAC CTT TAT TTT GCA
    G   T   H   Q   P   Y   T   F   G   G   G   T   K   L   E   I   K   R>
```

FIGURE 3: DNA/PROTEIN SEQUENCE OF 5/44 V$_H$

```
            10          20          30          40          50
    GAG GTC CAA CTG CAG CAG TCT GGG ACT GTA CTG GCA AGG CCT GGG GCT TCC GTG AAG
    CTC CAG GTT GAC GTC GTC AGA CCC TGA CAT GAC CGT TCC GGA CCC CGA AGG CAC TTC
     E   V   Q   L   Q   Q   S   G   T   V   L   A   R   P   G   A   S   V   K>

60          70          80          90         100         110
    ATG TCC TGC AAG GCT TCT GGC TAC AGG TTT ACC AAC TAC TGG ATT CAC TGG GTA AAA
    TAC AGG ACG TTC CGA AGA CCG ATG TCC AAA TGG TTG ATG ACC TAA GTG ACC CAT TTT
     M   S   C   K   A   S   G   Y   R   F   T   N   Y   W   I   H   W   V   K>

120         130         140         150         160         170
    CAG AGG CCT GGG CAG GGT CTA GAA TGG ATT GGT GGT ATT AAT CCT GGA AAT AAT TAT
    GTC TCC GGA CCC GTC CCA GAT CTT ACC TAA CCA CCA TAA TTA GGA CCT TTA TTA ATA
     Q   R   P   G   Q   G   L   E   W   I   G   G   I   N   P   G   N   N   Y>

180         190         200         210         220
    ACT ACG TAT AAG AGG AAC TTG AAG GGC AAG GCC ACA CTG ACT GCA GTC ACA TCC GCC
    TGA TGC ATA TTC TCC TTG AAC TTC CCG TTC CGG TGT GAC TGA CGT CAG TGT AGG CGG
     T   T   Y   K   R   N   L   K   G   K   A   T   L   T   A   V   T   S   A>

230         240         250         260         270         280
    AGC ACT GCC TAC ATG GAC CTC AGC AGC CTG ACA AGT GAG GAC TCT GCG GTC TAT TAC
    TCG TGA CGG ATG TAC CTG GAG TCG TCG GAC TGT TCA CTC CTG AGA CGC CAG ATA ATG
     S   T   A   Y   M   D   L   S   S   L   T   S   E   D   S   A   V   Y   Y>

290         300         310         320         330         340
    TGT ACA AGA GAG GGC TAT GGT AAC TAC GGG GCC TGG TTT GCT TAC TGG GGC CAG GGG
    ACA TGT TCT CTC CCG ATA CCA TTG ATG CCC CGG ACC AAA CGA ATG ACC CCG GTC CCC
     C   T   R   E   G   Y   G   N   Y   G   A   W   F   A   Y   W   G   Q   G>

350         360
    ACT CTG GTC ACC GTC TCC TCA
    TGA GAC CAG TGG CAG AGG AGT
     T   L   V   T   V   S   S>
```

FIGURE 4: REMOVAL OF GLYCOSYLATION SITE AND REACTIVE LYSINE: PCR STRATEGY TO MUTATE CDR-H2 IN CH VECTOR
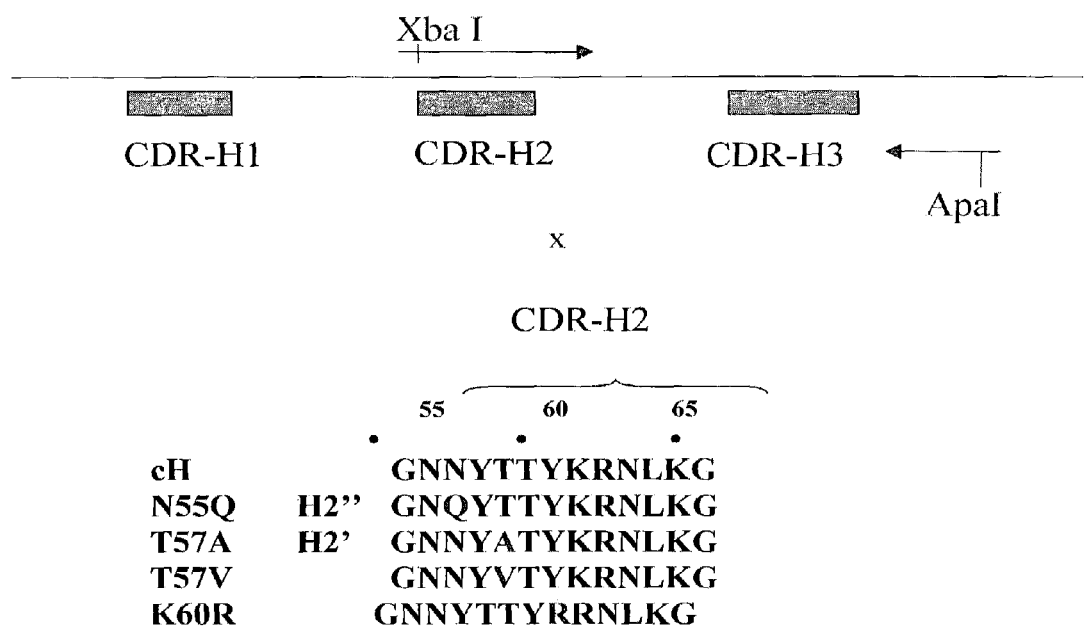

FIGURE 5: 5/44 LIGHT CHAIN SEQUENCE GRAFT DESIGN

```
               10         20                                    40
V_L    DVVVTQTPLSLPVSFGDQVSISC  RSSQSLANSYGNTFLS  WYLHKPGQSPQLLIY
       |||   |  |  ||  |   |  |                   ||    || |
DPK9   DIQMTQSPSSLSASVGDRVTITC                    WYQQKPGKAPKLLIY
       | |                                        ||        |
gL1    DVQVTQSPSSLSASVGDRVTITC  RSSQSLANSYGNTFLS  WYLHKPGKAPQLLIY
gL2    DVVVTQSPSSLSASVGDRVTITC  RSSQSLANSYGNTFLS  WYLHKPGKAPQLLIY 60        70        80        90
V_L    GISNRFS  GVPDRFTGSGSGTDFTLKISTIKPEDLGMYYC  LQGTHQPYT
                |  |           |  |||    |||
DPK9            GVPSRFSGSGSGTDFTLTISSLQPEDFATYYC
                                              |
gL1    GISNRFS  GVPDRFSGSGSGTDFTLTISSLQPEDFATYYC  LQGTHQPYT
gL2    GISNRFS  GVPDRFSGSGSGTDFTLTISSLQPEDFATYYC  LQGTHQPYT

100
V_L    FGGGTKLEIKR
       |       |
JK1    FGQGTKVEIKR gL1    FGQGTKVEIKR gL2    FGQGTKVEIKR
```

FIGURE 6: 5/44 HEAVY CHAIN SEQUENCE GRAFT DESIGN

```
              10         20         30         40         50
Vh    EVQLQQSGTVLARPGASVKMSCKASGYRFT NYWIH WVKQRPGQGLEWIG GINP
      |    |||||         |                 ||           |
DP7   QVQLVQSGAEVKKPGASVKVSCKASGYTFT       WVRQAPGQGLEWMG
      |                       |            |
gH1   EVQLVQSGAEVKKPGASVKVSCKASGYRFT NYWIH WVRQAPGQGLEWIG GINP
gH4,5&7 EVQLVQSGAEVKKPGASVKVSCKASGYRFT NYWIH WVRQAPGQGLEWIG GINP 60          70         80         90        100
Vh    GNNYTTYKRNLKG RAPLTAVTSASTAYMDLSSLTSEDSAVYYCTR EGYGNYG
          ||  ||||  |  ||   | |  |     |   |       |
DP7           KFQG  RVTMTRDTSTSTVYMELSSLRSEDTAVYYCAR
              |||                                  |
gH1   GNQYTTYKRNLKG RAPLTADTSTSTVYMELSSLRSEDTAVYYCTR EGYGNYG
gH4   GNNYATYRRNLKG RAPLTADTSTSTVYMELSSLRSEDTAVYYCTR EGYGNYG
gH5   GNNYATYRRNLKG RVTMTADTSTSTVYMELSSLRSEDTAVYYCTR EGYGNYG
gH6   GNNYATYRRKFQG RAPLTADTSTSTVYMELSSLRSEDTAVYYCTR EGYGNYG
gH7   GNNYATYRRKFQG RVTMTADTSTSTVYMELSSLRSEDTAVYYCTR EGYGNYG

110
JH6         WGQGTLVTVSS

Vh    AWFAY WGQGTLVTVSS gH1   AWFAY WGQGTLVTVSS
gH4,5&7 AWFAY WGQGTLVTVSS
```

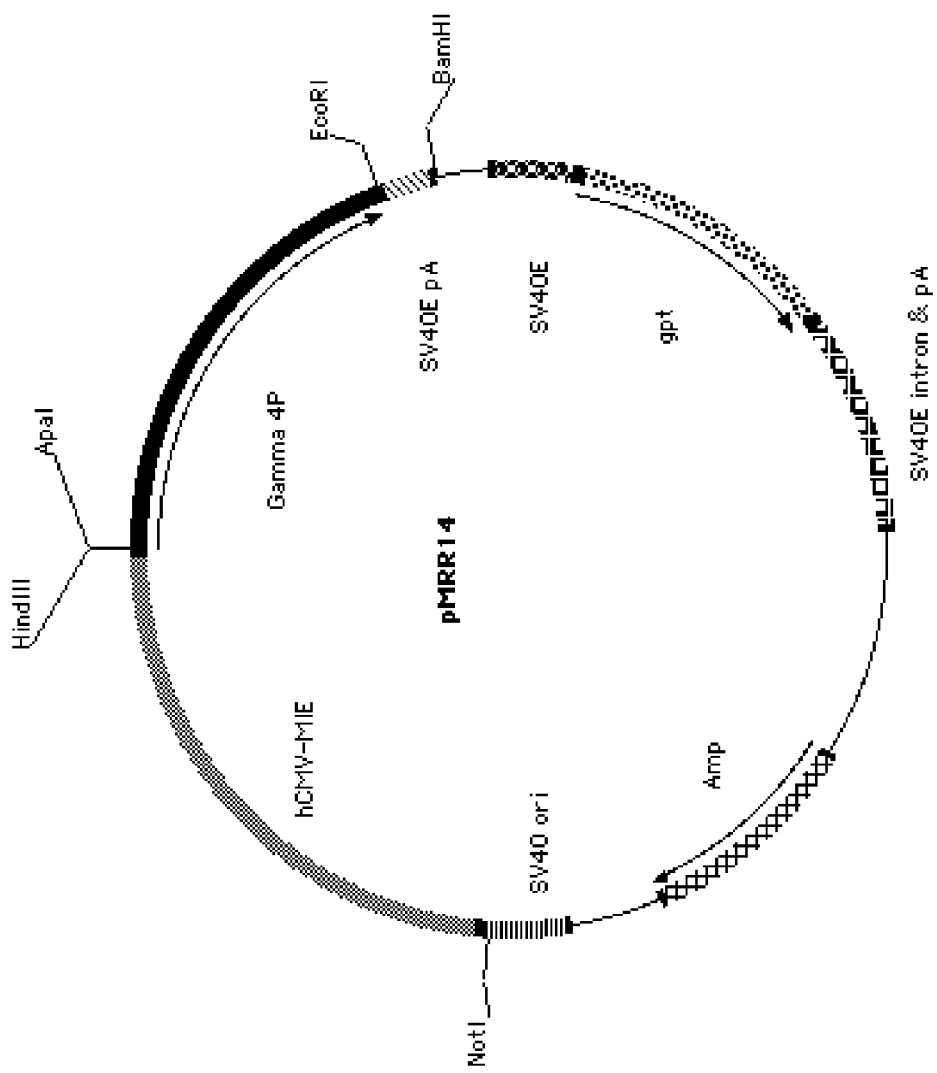
FIGURE 7: MAP OF VECTOR PMRR14

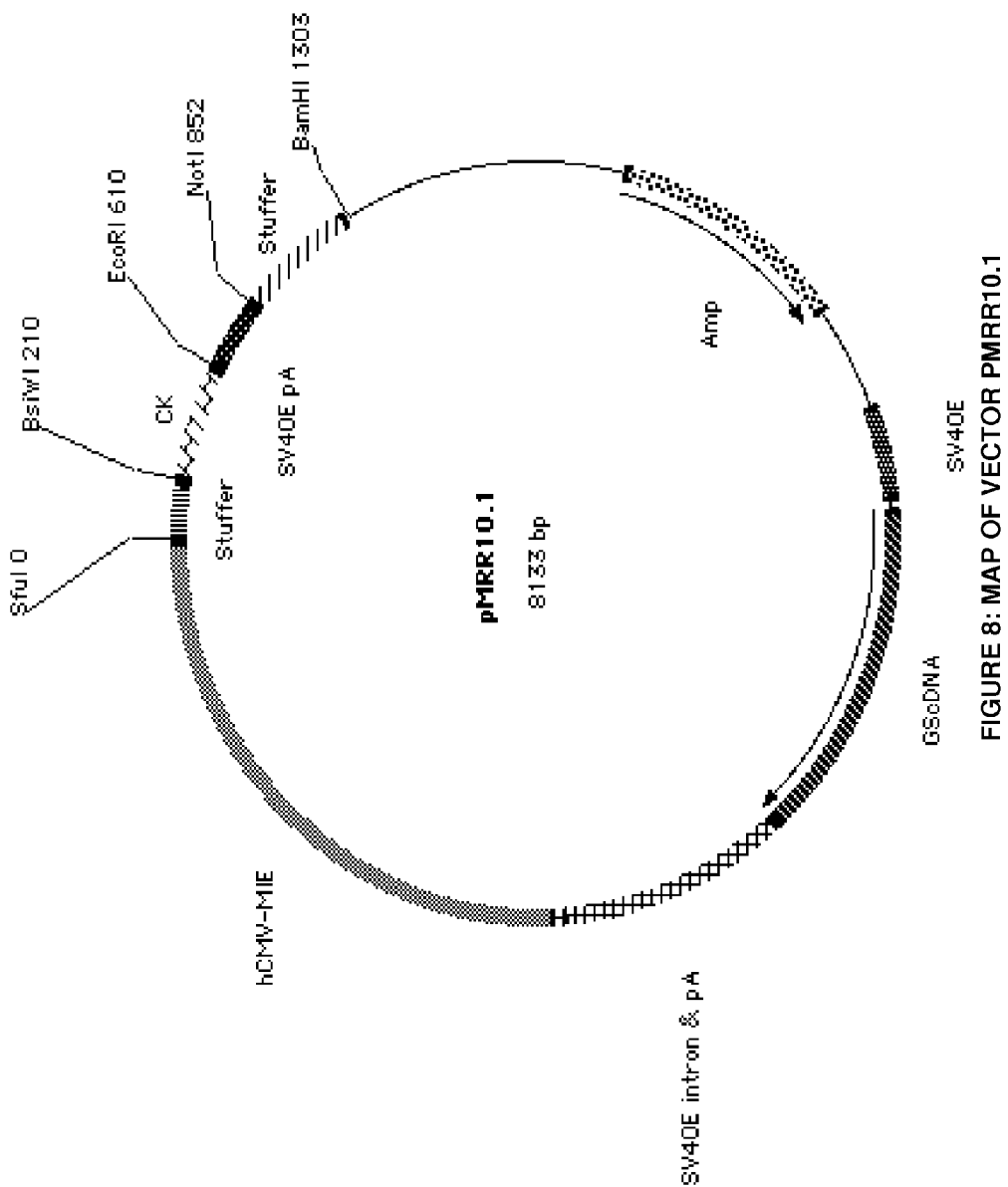
FIGURE 8: MAP OF VECTOR PMRR10.1

FIGURE 9: BIACORE ASSAY OF CHIMERIC 5/44 AND MUTANTS

| 5/44 | Ka $e^5$ | Kd $e^{-4}$ | KD $e^{-10}$ | ~KD nM |
|---|---|---|---|---|
| cLcH | 2.9 | 1.14 | 3.93 | 0.4 |
| N55Q | 5.81 | 1.9 | 3.27 | 0.3 |
| T57A | 7.8 | 0.51 | 0.66 | 0.07 |
| K60R | 4.95 | 1.01 | 2.04 | 0.2 |

FIGURE 10: OLIGONUCLEOTIDES FOR 5/44 GH1 AND GL1 GENE ASSEMBLIES

Heavy Chain

544gH1 T1
AGTGTGAGGTGCAATTGGTCCAGTCAGGAGCAGAGGTTAAGAAGCCTGGTGCTTCCGTC
AAAGTTTCGTGTAAGGCTAGCGGCTACAGGTTCAC

544gH1 T2
GTGGCATTAATCCCGGGAATCAGTACACTACATATAAAAGAAATCTAAAGGGCAGAGCA
ACGCTGACCGCGGACACCTCCACAAGCACTGTCTACA

544gH1 T3
AGAGAAGGCTACGGTAATTACGGAGCCTGGTTCGCCTACTGGGGCCAGGGTACCCTAGT
CACAGTCTCCTCAGCTTCTACAAAGGGCCCAAGAAA 544 gH1 B1
GGACCAATTGCACCTCACACTGCACTCCCTTGAGAATGAGTGCCAGGAACACGAGAGAG
AATCCGAAGTCCATGGTGGCGGCAAGCTTTTATTC 544 gH1 B2
GATTCCCGGGATTAATGCCACCGATCCATTCCAGGCCTTGTCCCGGAGCCTGCCTGACCC
AATGAATCCAATAATTTGTGAACCTGTAGCCGCTAGC

544gH1 B3
CGTAATTACCGTAGCCTTCTCTAGTACAATAGTACACTGCGGTGTCCTCGGATCTCAGAG
ATGACAGCTCCATGTAGACAGTGCTTGTGGAGG

544gH1 F1
GAATAAAAGCTTGCCGCCACC

544gH1 R1
TTTCTTGGGCCCTTTGTAGAAG

FIGURE 10 CONT.

Light Chain 544 gL1 T1
GCTTCCCGGGGTGACGTTCAAGTGACCCAGAGCCCATCCAGCCTGAGCGCATCTGTAGG
AGACCGGGTCACCATCACTTGTAGATCC 544 gL1 T2
TATCTGCACAAACCAGGTAAAGCCCCACAATTGCTCATCTACGGAATCTCTAACAGATTT
AGTGGTGTACCAGACAGGTTCAGCGGTTCC 544gL1 T3
AGATTTCGCCACTTATTACTGTTTACAAGGTACACATCAGCCGTACACATTCGGTCAGGG
TACTAAAGTAGAAATCAAACGTACGGCGTGC 544gL1 B1
GAACGTCACCCCGGGAAGCAGGAATCCAGAACAACAGAAGCACCAACAGCCTAACAGG
CAACTTCATGGTGGCGGCTTCGAATCATCC 544gL1 B2
CTTTACCTGGTTTGTGCAGATACCAAGACAAAAAGGTGTTCCCATAACTGTTTGCAAGAC
TCTGACTGGATCTACAAGTGATGGTGAC 544gL1 B3
AACAGTAATAAGTGGCGAAATCTTCTGGCTGGAGAGACGAGATCGTGAGGGTGAAATCA
GTACCACTTCCGGAACCGCTGAACCTGTCTG 544gL1 F1
GGATGATTCGAAGCCGCCAC 544gL1 R1
GCACGCCGTACGTTTGATTTC

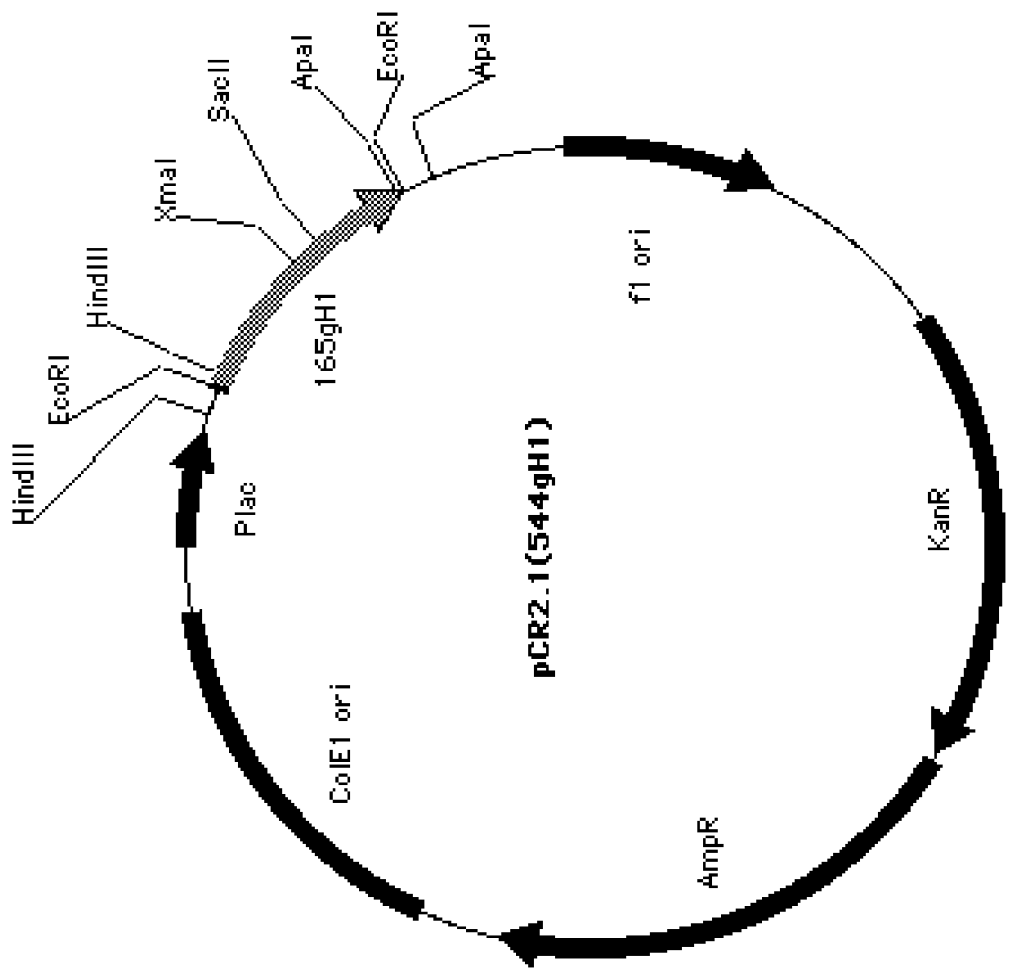
FIGURE 11: PLASMID MAPS OF INTERMEDIATE VECTORS PCR2.1 (544GH1)

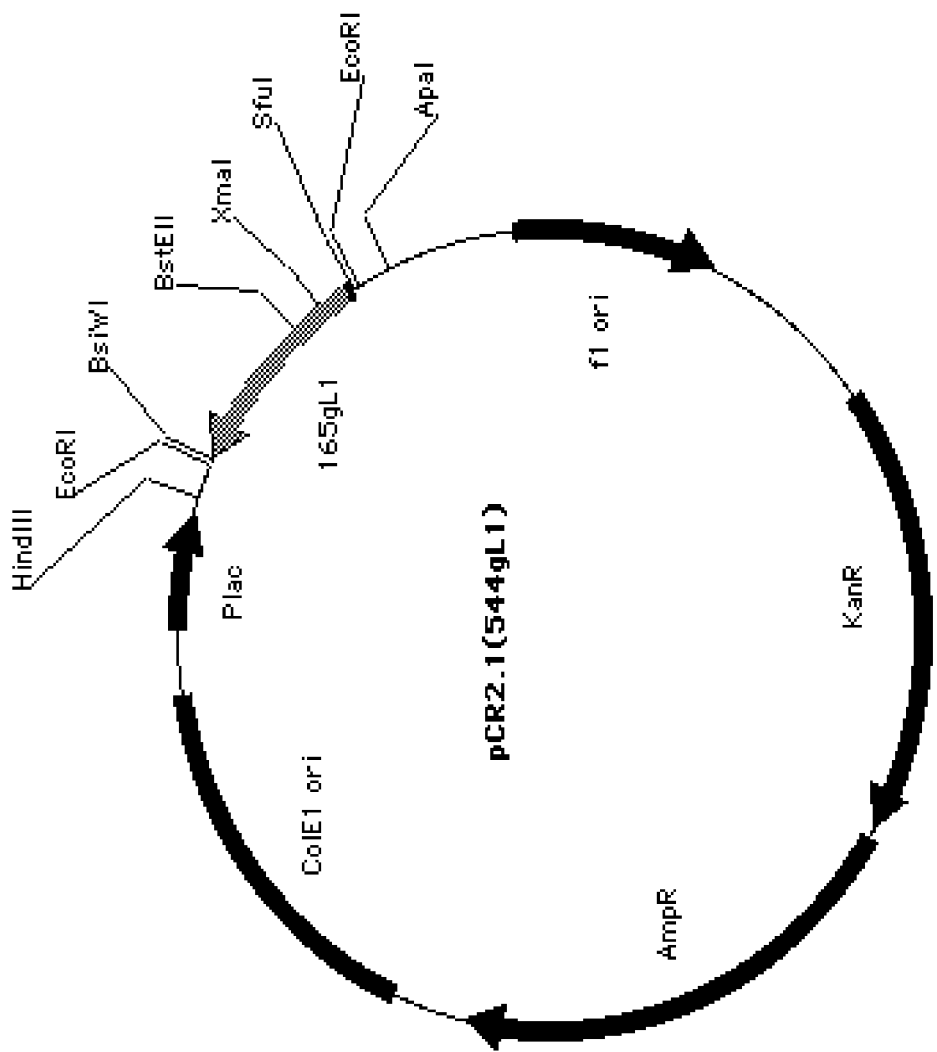
FIGURE 12: PLASMID MAPS OF INTERMEDIATE VECTORS PCR2.1 (544Gl1)

FIGURE 13: OLIGONUCLEOTIDE CASSETTES USED TO MAKE FURTHER GRAFTS gH4

```
    XmaI         10             20             30             40             50         SacII
    CC GGG AAT AAC TAC GCT ACA TAT AGG AGA AAT CTA AAG GGC AGA GCA ACG CTG ACC GC
        C TTA TTG ATG CGA TGT ATA TCC TCT TTA GAT TTC CCG TCT CGT TGC GAC TGG
    P    G    N    N    Y    A    T    Y    R    R    N    L    K    G    R    A    T    L    T    A
``` gH5

```
    XmaI         10             20             30             40             50         SacII
    CC GGG AAT AAC TAC GCT ACA TAT AGG AGA AAT CTA AAG GGC AGA GTT ACG ATG ACC GC
        C TTA TTG ATG CGA TGT ATA TCC TCT TTA GAT TTC CCG TCT CAA TGC TAC TGG
    P    G    N    N    Y    A    T    Y    R    R    K    F    Q    G    R    V    T    M    T    A
``` gH6

```
    XmaI         10             20             30             40             50         SacII
    CC GGG AAT AAC TAC GCT ACA TAT AGG AGA AAA TTC CAG GGC AGA GCA ACG CTG ACC GC
        C TTA TTG ATG CGA TGT ATA TCC TCT TTT AAG GTC CCG TCT CGT TGC GAC TGG
    P    G    N    N    Y    A    T    Y    R    R    K    F    Q    G    R    A    T    L    T    A
``` gH7

```
    XmaI         10             20             30             40             50         SacII
    CC GGG AAT AAC TAC GCT ACA TAT AGG AGA AAA TTC CAG GGC AGA GTT ACG ATG ACC GC
        C TTA TTG ATG CGA TGT ATA TCC TCT TTT AAG GTC CCG TCT CAA TGC TAC TGG
    P    G    N    N    Y    A    T    Y    R    R    K    F    Q    G    R    V    T    M    T    A
``` gL2

```
         XmaI    10             20             30             40             50             60
    BstEII
         C CGG GGT GAC GTT GTC GTG ACC CAG AGC CCA TCC AGC CTG AGC GCA TCT GTA GGA GAC CGG
              CCA CTG CAA CAG CAC TGG GTC TCG GGT AGG TCG GAC TCG CGT AGA CAT CCT CTG GCC CAG TG
         S    R    G    D    V    V    V    T    Q    S    P    S    S    L    S    A    S    V    G    D    R    V    T
```

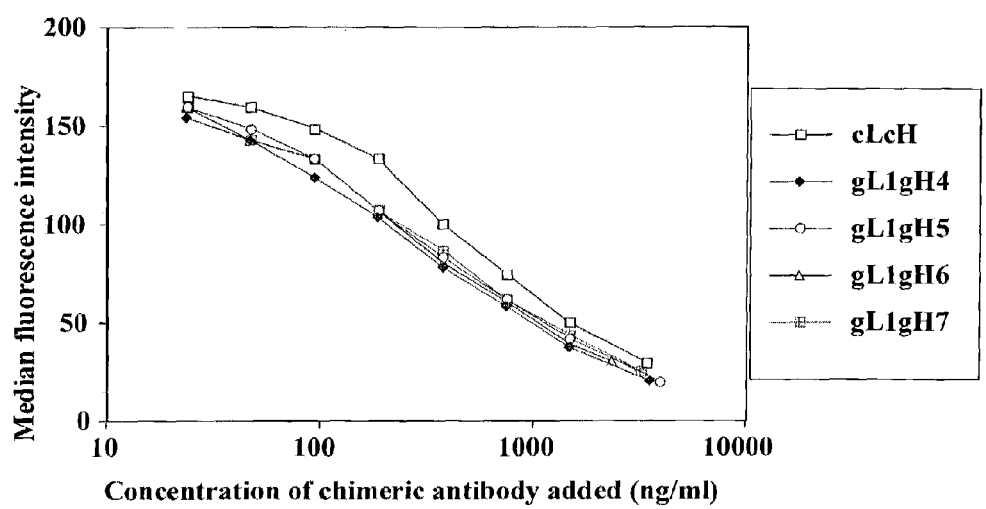
FIGURE 14: COMPETITION ASSAY, COMPETING BINDING OF FLUORESCENTLY LABELLED MOUSE 5/44 ANTIBODY WITH GRAFTED VARIANTS.

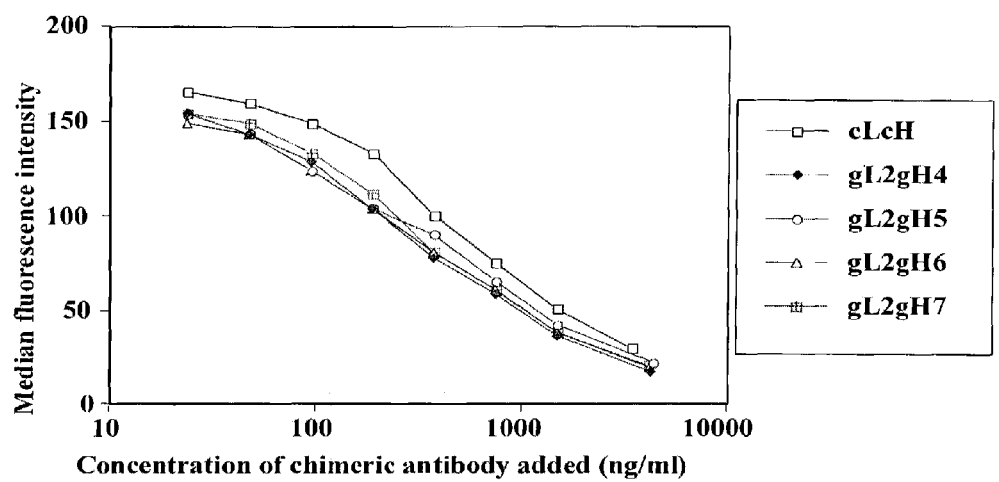
FIGURE 15: COMPETITION ASSAY, COMPETING BINDING OF FLUORESCENTLY LABELLED MOUSE 5/44 ANTIBODY WITH GRAFTED VARIANTS.

FIGURE 16: FULL DNA SEQUENCE OF GRAFTED HEAVY AND LIGHT CHAINS a) Heavy Chain

```
         10            20            30            40            50            60
AAGCTTGCCG CCACC ATG GAC TTC GGA TTC TCT CTC GTG TTC CTG GCA CTC ATT CTC AAG
TTCCAACGGC GGTGG TAC CTG AAG CCT AAG AGA GAG CAC AAG GAC CGT GAG TAA GAG TTC
                  M   D   F   G   F   S   L   V   F   L   A   L   I   L   K>

70            80            90           100           110
GGA GTG CAG TGT GAG GTG CAA TTG GTC CAG TCA GGA GCA GAG GTT AAG AAG CCT GGT
CCT CAC GTC ACA CTC CAC GTT AAC CAG GTC AGT CCT CGT CTC CAA TTC TTC GGA CCA
 G   V   Q   C   E   V   Q   L   V   Q   S   G   A   E   V   K   K   P   G>

120           130           140           150           160           170
GCT TCC GTC AAA GTT TCG TGT AAG GCT AGC GGC TAC AGG TTC ACA AAT TAT TGG ATT
CGA AGG CAG TTT CAA AGC ACA TTC CGA TCG CCG ATG TCC AAG TGT TTA ATA ACC TAA
 A   S   V   K   V   S   C   K   A   S   G   Y   R   F   T   N   Y   W   I>

180           190           200           210           220           230
CAT TGG GTC AGG CAG GCT CCG GGA CAA GGC CTG GAA TGG ATC GGT GCC ATT AAT CCC
GTA ACC CAG TCC GTC CGA GGC CCT GTT CCG GAC CTT ACC TAG CCA CCG TAA TTA GGG
 H   W   V   R   Q   A   P   G   Q   G   L   E   W   I   G   G   I   N   P>

240           250           260           270           280
GGG AAT AAC TAC GCT ACA TAT AGG AGA AAA TTC CAG GGC AGA GTT ACG ATG ACC GCG
CCC TTA TTG ATG CGA TGT ATA TCC TCT TTT AAG GTC CCG TCT CAA TGC TAC TGG CGC
 G   N   N   Y   A   T   Y   R   R   K   F   Q   G   R   V   T   M   T   A>

290           300           310           320           330           340
GAC ACC TCC ACA AGC ACT GTC TAC ATG GAG CTG TCA TCT CTG AGA TCC GAG GAC ACC
CTG TGG AGG TGT TCG TGA CAG ATG TAC CTC GAC AGT AGA GAC TCT AGG CTC CTG TGG
 D   T   S   T   S   T   V   Y   M   E   L   S   S   L   R   S   E   D   T>

350           360           370           380           390           400
GCA GTG TAC TAT TGT ACT AGA GAA GGC TAC GGT AAT TAC GGA GCC TGG TTC GCC TAC
CGT CAC ATG ATA ACA TGA TCT CTT CCG ATG CCA TTA ATG CCT CGG ACC AAG CGG ATG
 A   V   Y   Y   C   T   R   E   G   Y   G   N   Y   G   A   W   F   A   Y>

410           420           430           440           450
TGG GGC CAG GGT ACC CTA GTC ACA GTC TCC TCA GCT TCT ACA AAG GGC CCA TCC GTC
ACC CCG GTC CCA TGG GAT CAG TGT CAG AGG AGT CGA AGA TGT TTC CCG GGT AGG CAG
 W   G   Q   G   T   L   V   T   V   S   S   A   S   T   K   G   P   S   V>

460           470           480           490           500           510
TTC CCC CTG GCG CCC TGC TCC AGG AGC ACC TCC GAG AGC ACA GCC GCC CTG GGC TGC
AAG GGG GAC CGC GGG ACG AGG TCC TCG TGG AGG CTC TCG TGT CGG CGG GAC CCG ACG
 F   P   L   A   P   C   S   R   S   T   S   E   S   T   A   A   L   G   C>

520           530           540           550           560           570
CTG GTC AAG GAC TAC TTC CCC GAA CCG GTG ACG GTG TCG TGG AAC TCA GGC GCC CTG
GAC CAG TTC CTG ATG AAG GGG CTT GGC CAC TGC CAC AGC ACC TTG AGT CCG CGG GAC
 L   V   K   D   Y   F   P   E   P   V   T   V   S   W   N   S   G   A   L>

580           590           600           610           620           630
ACC AGC GGC GTG CAC ACC TTC CCG GCT GTC CTA CAG TCC TCA GGA CTC TAC TCC CTC
TGG TCG CCG CAC GTG TGG AAG GGC CGA CAG GAT GTC AGG AGT CCT GAG ATG AGG GAG
 T   S   G   V   H   T   F   P   A   V   L   Q   S   S   G   L   Y   S   L>
```

FIGURE 16 CONT.

```
          640         650         660         670         680
AGC AGC GTG GTG ACC GTG CCC TCC AGC ACC TTG GGC ACG AAG ACC TAC ACC TGC AAC
TCG TCG CAC CAC TGG CAC GGG AGG TCG TCG AAC CCG TGC TTC TGG ATG TGG ACG TTG
 S   S   V   V   T   V   P   S   S   L   G   T   K   T   Y   T   C   N>

690         700         710         720         730         740
GTA GAT CAC AAG CCC AGC AAC ACC AAG GTG GAC AAG AGA GTT G GTGAGAGGCC
CAT CTA GTG TTC GGG TCG TTG TGG TTC CAC CTG TTC TCT CAA C CACTCTCCGG
 V   D   H   K   P   S   N   T   K   V   D   K   R   V>

750         760         770         780         790         800         810
AGCACAGGCA GGGAGGGTGT CTGCTGGAAG CCAGGCTCAG CCCTCCTGCC TGGACGCACC CCGGCTGTGC
TCGTGTCCCT CCCTCCCACA GACGACCTTC GGTCCGAGTC GGGAGGACGG ACCTGCGTGG GGCCGACACG 820         830         840         850         860         870         880
AGCCCCAGCC CAGGGCAGCA AGGCATGCCC CATCTGTCTC CTCACCCCGA GGCCTCTGAC CACCCCACTC
TCGGGGTCGG GTCCCGTCGT TCCGTACGGG GTAGACAGAG GAGTGGGCCT CCGGAGACTG GTGGGGTGAG 890         900         910         920         930         940         950
ATGCCCAGGG AGAGGGTCTT CTGGATTTTT CCACCAGGCT CCGGGCAGCC ACAGGCTGGA TGCCCCTACC
TACGGGTCCC TCTCCCAGAA GACCTAAAAA GGTGGTCCGA GGCCCGTCGG TGTCCGACCT ACGGGGATGG 960         970         980         990        1000        1010        1020
CCAGGCCCTG CGCATACAGG GGCAGGTGCT GCGCTCAGAC CTGCCAAGAG CCATATCCGG GAGGACCCTG
GGTCCGGGAC GCGTATGTCC CCGTCCACGA CGCGAGTCTG GACGGTTCTC GGTATAGGCC CTCCTGGGAC 1030        1040        1050        1060        1070        1080        1090
CCCCTGACCT AAGCCCACCC CAAAGGCCAA ACTCTCCACT CCCTCAGCTC AGACACCTTC TCTCCTCCCA
GGGGACTGGA TTCGGGTGGG GTTTCCGGTT TGAGAGGTGA GGGAGTCGAG TCTGTGGAAG AGAGGAGGGT 1100        1110        1120         1130        1140        1150
GATCTGAGTA ACTCCCAATC TTCTCTCTGC A GAG TCC AAA TAT GGT CCC CCA TGC CCA CCA
CTAGACTCAT TGAGGGTTAG AAGAGAGACG T CTC AGG TTT ATA CCA GGG GGT ACG GGT GGT
                                    E   S   K   Y   G   P   P   C   P   P>

1160        1170        1180        1190        1200        1210        1220
 TGC CCA GGT AAGCCAACCC AGGCCTCGCC CTCCAGCTCA AGGCGGGACA GGTGCCCTAG AGTAGCCTGC
 ACG GGT CCA TTCGGTTGGG TCCGGAGCGG GAGGTCGAGT TCCGCCCTGT CCACGGGATC TCATCGGACG
  C   P>

1230        1240        1250        1260        1270        1280
ATCCAGGGAC AGGCCCCAGC CGGGTGCTGA CGCATCCACC TCCATCTCTT CCTCA GCA CCT GAG TTC
TAGGTCCCTG TCCGGGGTCG GCCCACGACT GCGTAGGTGG AGGTAGAGAA GGAGT CGT GGA CTC AAG
                                                            A   P   E   F>

1290        1300        1310        1320        1330        1340
CTG GGG GGA CCA TCA GTC TTC CTG TTC CCC CCA AAA CCC AAG GAC ACT CTC ATG ATC
GAC CCC CCT GGT AGT CAG AAG GAC AAG GGG GGT TTT GGG TTC CTG TGA GAG TAC TAG
 L   G   G   P   S   V   F   L   F   P   P   K   P   K   D   T   L   M   I>

1350        1360        1370        1380        1390        1400
TCC CGG ACC CCT GAG GTC ACG TGC GTG GTG GTG GAC GTG AGC CAG GAA GAC CCC GAG
AGG GCC TGG GGA CTC CAG TGC ACG CAC CAC CAC CTG CAC TCG GTC CTT CTG GGG CTC
 S   R   T   P   E   V   T   C   V   V   V   D   V   S   Q   E   D   P   E>
```

FIGURE 16 CONT.

```
         1410           1420          1430           1440           1450
     GTC CAG TTC AAC TGG TAC GTG GAT GGC GTG GAG GTG CAT AAT GCC AAG ACA AAG CCG
     CAG GTC AAG TTG ACC ATG CAC CTA CCG CAC CTC CAC GTA TTA CGG TTC TGT TTC GGC
      V   Q   F   N   W   Y   V   D   G   V   E   V   H   N   A   K   T   K   P>

1460           1470          1480           1490          1500           1510
  CGG GAG GAG CAG TTC AAC AGC ACG TAC CGT GTG GTC AGC GTC CTC ACC GTC CTG CAC
  GCC CTC CTC GTC AAG TTG TCG TGC ATG GCA CAC CAG TCG CAG GAG TGG CAG GAC GTG
   R   E   E   Q   F   N   S   T   Y   R   V   V   S   V   L   T   V   L   H>

1520           1530          1540           1550          1560          1570
     CAG GAC TGG CTG AAC GGC AAG GAG TAC AAG TGC AAG GTC TCC AAC AAA GGC CTC CCG
     GTC CTG ACC GAC TTG CCG TTC CTC ATG TTC ACG TTC CAG AGG TTG TTT CCG GAG GGC
      Q   D   W   L   N   G   K   E   Y   K   C   K   V   S   N   K   G   L   P>

1580          1590          1600           1610          1620          1630
       TCC TCC ATC GAG AAA ACC ATC TCC AAA GCC AAA GGTGG GACCCACGGG GTGCGAGGGC
       AGG AGG TAG CTC TTT TGG TAG AGG TTT CGG TTT CCACC CTGGGTGCCC CACGCTCCCG
        S   S   I   E   K   T   I   S   K   A   K>

1640          1650          1660           1670          1680          1690          1700
     CACATGGACA GAGGTCAGCT CGGCCCACCC TCTGCCCTGG GAGTGACCGC TGTGCCAACC TCTGTCCCTA
     GTGTACCTGT CTCCAGTCGA GCCGGGTGGG AGACGGGACC CTCACTGGCG ACACGGTTGG AGACAGGGAT 1710          1720          1730           1740          1750
     CA GGG CAG CCC CGA GAG CCA CAG GTG TAC ACC CTG CCC CCA TCC CAG GAG GAG ATG
     GT CCC GTC GGG GCT CTC GGT GTC CAC ATG TGG GAC GGG GGT AGG GTC CTC CTC TAC
         G   Q   P   R   E   P   Q   V   Y   T   L   P   P   S   Q   E   E   M>

1760          1770          1780          1790           1800          1810
     ACC AAG AAC CAG GTC AGC CTG ACC TGC CTG GTC AAA GGC TTC TAC CCC AGC GAC ATC
     TGG TTC TTG GTC CAG TCG GAC TGG ACG GAC CAG TTT CCG AAG ATG GGG TCG CTG TAG
      T   K   N   Q   V   S   L   T   C   L   V   K   G   F   Y   P   S   D   I>

1820          1830          1840          1850           1860          1870
     GCC GTG GAG TGG GAG AGC AAT GGG CAG CCG GAG AAC AAC TAC AAG ACC ACG CCT CCC
     CGG CAC CTC ACC CTC TCG TTA CCC GTC GGC CTC TTG TTG ATG TTC TGG TGC GGA GGG
      A   V   E   W   E   S   N   G   Q   P   E   N   N   Y   K   T   T   P   P>

1880          1890          1900          1910           1920
     GTG CTG GAC TCC GAC GGC TCC TTC TTC CTC TAC AGC AGG CTA ACC GTG GAC AAG AGC
     CAC GAC CTG AGG CTG CCG AGG AAG AAG GAG ATG TCG TCC GAT TGG CAC CTG TTC TCG
      V   L   D   S   D   G   S   F   F   L   Y   S   R   L   T   V   D   K   S>

1930          1940          1950          1960           1970          1980
     AGG TGG CAG GAG GGG AAT GTC TTC TCA TGC TCC GTG ATG CAT GAG GCT CTG CAC AAC
     TCC ACC GTC CTC CCC TTA CAG AAG AGT ACG AGG CAC TAC GTA CTC CGA GAC GTG TTG
      R   W   Q   E   G   N   V   F   S   C   S   V   M   H   E   A   L   H   N>

1990          2000          2010          2020           2030          2040
     CAC TAC ACA CAG AAG AGC CTC TCC CTG TCT CTG GGT AAA TGA GTGC CAGGGCCGGC
     GTG ATG TGT GTC TTC TCG GAG AGG GAC AGA GAC CCA TTT ACT CACG GTCCCGGCCG
      H   Y   T   Q   K   S   L   S   L   S   L   G   K   *>

2050          2060          2070          2080           2090          2100          2110
     AAGCCCCCGC TCCCCGGGCT CTCGGGGTCG CGCGAGGATG CTTGGCACGT ACCCCGTCTA CATACTTCCC
     TTCGGGGGCG AGGGGCCCGA GAGCCCCAGC GCGCTCCTAC GAACCGTGCA TGGGGCAGAT GTATGAAGGG
```

FIGURE 16 CONT

```
           2120       2130       2140       2150       2160
     AGGCACCCAG CATGGAAATA AAGCACCCAC CACTGCCCTG GCTCGAATTC
     TCCGTGGGTC GTACCTTTAT TTCGTGGGTG GTGACGGGAC CGAGCTTAAG
```

FIGURE 16 CONT.

b) Light Chain

```
              10         20         30         40         50         60
       TTCGAAGCCG CCACC ATG AAG TTG CCT GTT AGG CTG TTG GTG CTT CTG TTG TTC TGG ATT
       AAGCTTCGGC GGTGG TAC TTC AAC GGA CAA TCC GAC AAC CAC GAA GAC AAC AAG ACC TAA
                         M   K   L   P   V   R   L   L   V   L   L   L   F   W   L>

70         80         90         100        110
       CCT GCT TCC CGG GGT GAC GTT CAA GTG ACC CAG AGC CCA TCC AGC CTG AGC GCA TCT
       GGA CGA AGG GCC CCA CTG CAA GTT CAC TGG GTC TCG GGT AGG TCG GAC TCG CGT AGA
        P   A   S   R   G   D   V   Q   V   T   Q   S   P   S   S   L   S   A   S>

120        130        140        150        160        170
       GTA GGA GAC CGG GTC ACC ATC ACT TGT AGA TCC AGT CAG AGT CTT GCA AAC AGT TAT
       CAT CCT CTG GCC CAG TGG TAG TGA ACA TCT AGG TCA GTC TCA GAA CGT TTG TCA ATA
        V   G   D   R   V   T   I   T   C   R   S   S   Q   S   L   A   N   S   Y>

180        190        200        210        220        230
       GGG AAC ACC TTT TTG TCT TGG TAT CTG CAC AAA CCA GGT AAA GCC CCA CAA TTG CTC
       CCC TTG TGG AAA AAC AGA ACC ATA GAC GTG TTT GGT CCA TTT CGG GGT GTT AAC GAG
        G   N   T   F   L   S   W   Y   L   H   K   P   G   K   A   P   Q   L   L>

240        250        260        270        280
       ATC TAC GGA ATC TCT AAC AGA TTT AGT GGT GTA CCA GAC AGG TTC AGC GGT TCC GGA
       TAG ATG CCT TAG AGA TTG TCT AAA TCA CCA CAT GGT CTG TCC AAG TCG CCA AGG CCT
        I   Y   G   I   S   N   R   F   S   G   V   P   D   R   F   S   G   S   G>

290        300        310        320        330        340
       AGT GGT ACT GAT TTC ACC CTC ACG ATC TCG TCT CTC CAG CCA GAA GAT TTC GCC ACT
       TCA CCA TGA CTA AAG TGG GAG TGC TAG AGC AGA GAG GTC GGT CTT CTA AAG CGG TGA
        S   G   T   D   F   T   L   T   I   S   S   L   Q   P   E   D   F   A   T>

350        360        370        380        390        400
       TAT TAC TGT TTA CAA GGT ACA CAT CAG CCG TAC ACA TTC GGT CAG GGT ACT AAA GTA
       ATA ATG ACA AAT GTT CCA TGT GTA GTC GGC ATG TGT AAG CCA GTC CCA TGA TTT CAT
        Y   Y   C   L   Q   G   T   H   Q   P   Y   T   F   G   Q   G   T   K   V>

410        420        430        440        450
       GAA ATC AAA CGT ACG GTA GCG GCC CCA TCT GTC TTC ATC TTC CCG CCA TCT GAT GAG
       CTT TAG TTT GCA TGC CAT CGC CGG GGT AGA CAG AAG TAG AAG GGC GGT AGA CTA CTC
        E   I   K   R   T   V   A   A   P   S   V   F   I   F   P   P   S   D   E>

460        470        480        490        500        510
       CAG TTG AAA TCT GGA ACT GCC TCT GTT GTG TGC CTG CTG AAT AAC TTC TAT CCC AGA
       GTC AAC TTT AGA CCT TGA CGG AGA CAA CAC ACG GAC GAC TTA TTG AAG ATA GGG TCT
        Q   L   K   S   G   T   A   S   V   V   C   L   L   N   N   F   Y   P   R>

520        530        540        550        560        570
       GAG GCC AAA GTA CAG TGG AAG GTG GAT AAC GCC CTC CAA TCG GGT AAC TCC CAG GAG
       CTC CGG TTT CAT GTC ACC TTC CAC CTA TTG CGG GAG GTT AGC CCA TTG AGG GTC CTC
        E   A   K   V   Q   W   K   V   D   N   A   L   Q   S   G   N   S   Q   E>

580        590        600        610        620        630
       AGT GTC ACA GAG CAG GAC AGC AAG GAC AGC ACC TAC AGC CTC AGC AGC ACC CTG ACG
       TCA CAG TGT CTC GTC CTG TCG TTC CTG TCG TGG ATG TCG GAG TCG TCG TGG GAC TGC
        S   V   T   E   Q   D   S   K   D   S   T   Y   S   L   S   S   T   L   T>

```
CTG AGC AAA GCA GAC TAC GAG AAA CAC AAA GTC TAC GCC TGC GAA GTC ACC CAT CAG
GAC TCG TTT CGT CTG ATG CTC TTT GTG TTT CAG ATG CGG ACG CTT CAG TGG GTA GTC
 L   S   K   A   D   Y   E   K   H   K   V   Y   A   C   E   V   T   H   Q>

690         700         710         720         730         740
GGC CTG AGC TCG CCC GTC ACA AAG AGC TTC AAC AGG GGA GAG TGT TAG AGGGA
CCG GAC TCG AGC GGG CAG TGT TTC TCG AAG TTG TCC CCT CTC ACA ATC TCCCT
 G   L   S   S   P   V   T   K   S   F   N   R   G   E   C   *>

750         760         770         780
    GAAGTGCCCC CACCTGCTCC TCAGTTCCAG CCTGGGAATT C
    CTTCACGGGG GTGGACGAGG AGTCAAGGTC GGACCCTTAA G
```

FIGURE 17: STRUCTURE OF AN ANTIBODY-NAC-GAMMA CALICHEAMICIN DMH CONJUGATE
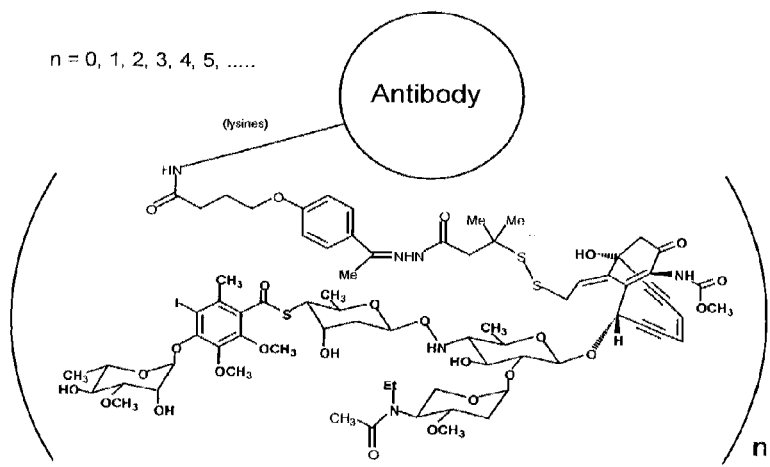

FIGURE 18: EFFECT OF CMC-544 ON GROWTH OF RAMOS B-CELL LYMPHOMA
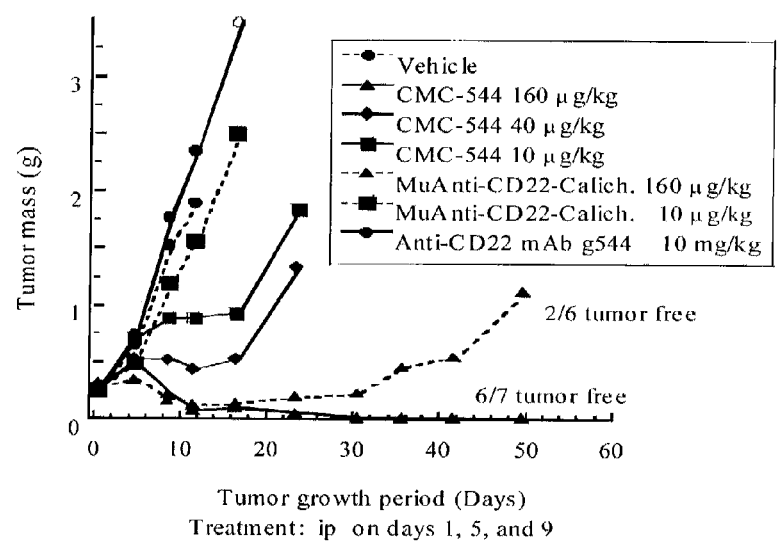

FIGURE 19: EFFECT OF CMC-544 ON LARGE B-CELL LYMPHOMAS
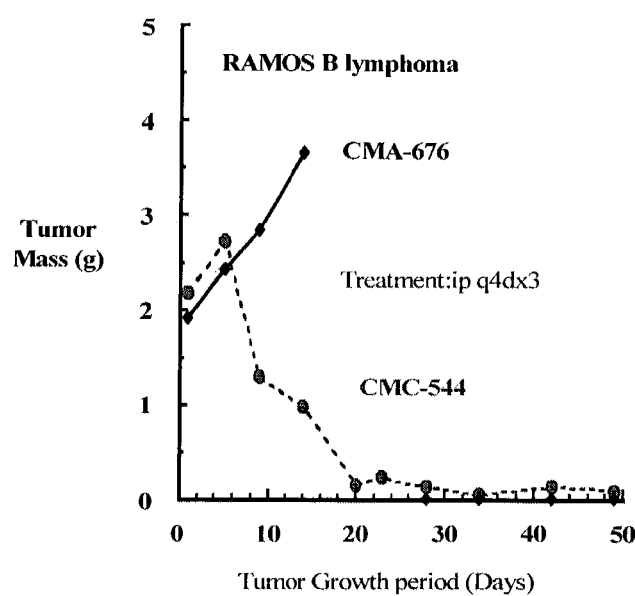

FIGURE 20: EFFECT OF CMC-544 MADE WITH THE CMA AND CMC CONJUGATION PROCEDURES ON THE GROWTH OF RL LYMPHOMA
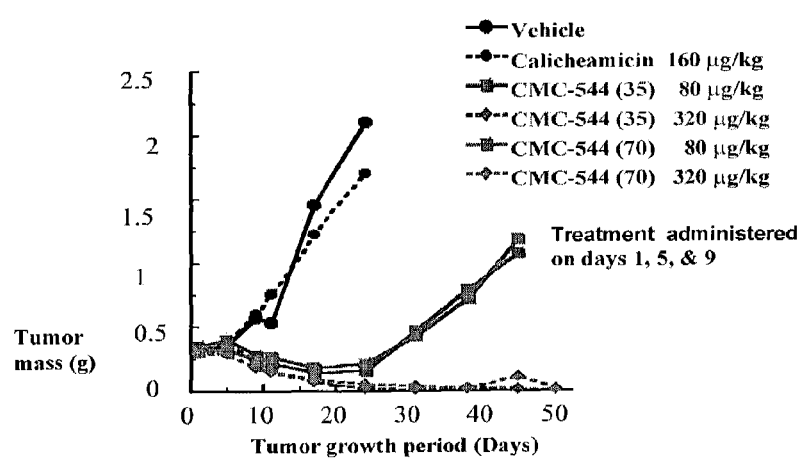

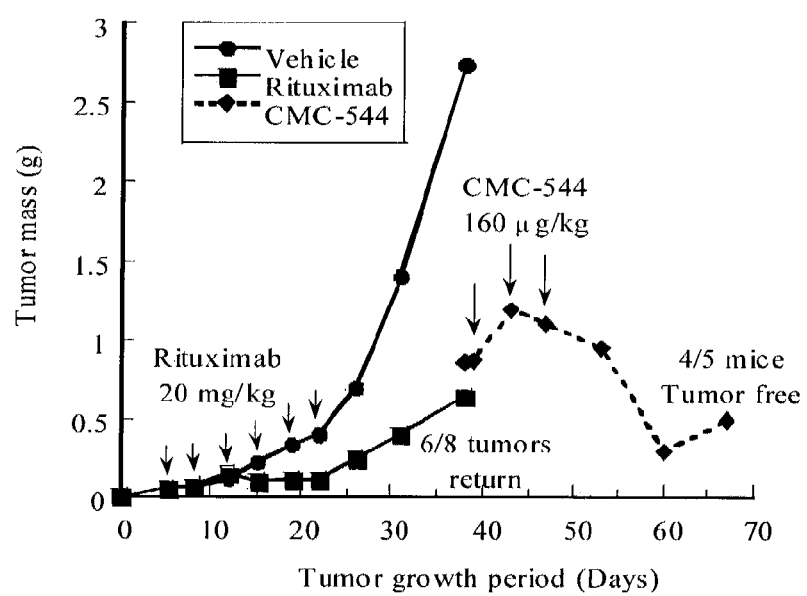
FIGURE 21: RITUXIMAB (RITUXAN™)-TREATED LARGE RL LYMPHOMA IS SUSCEPTIBLE TO CMC-544

FIGURE 22: EFFECT OF RITUXIMAB (RITUXAN™) ON THE CYTOTOXIC ACTIVITY OF CMC-544
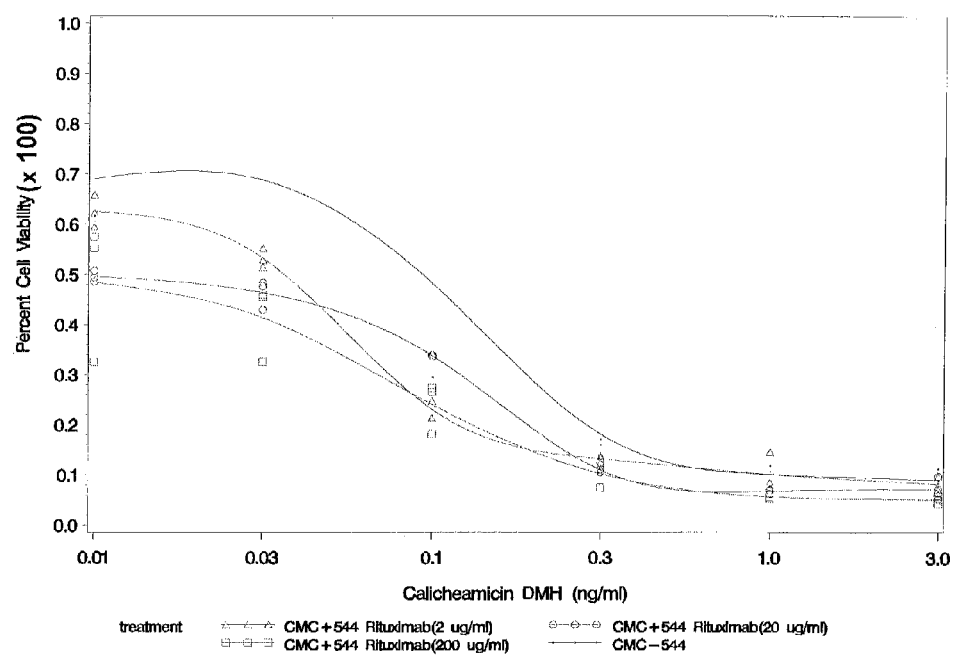

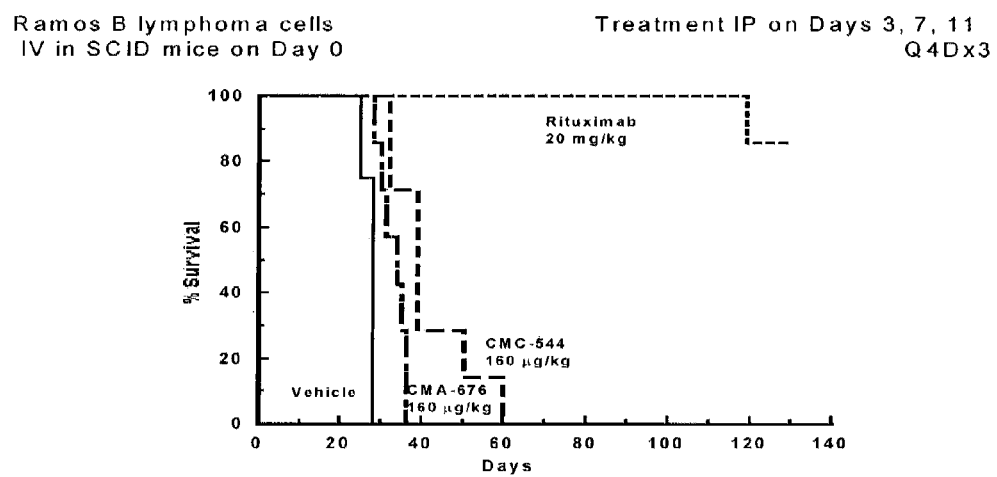
FIGURE 23: EFFECT OF CMC-544, RITUXIMAB (RITUXAN™)-, AND CMA-676 ON SURVIVAL OF SCID MICE WITH DISSEMINATED EARLY RAMOS B LYMPHOMA FIGURE 24: EFFECT OF CMC-544, RITUXIMAB (RITUXAN™), AND CMA-676 ON SURVIVAL OF SCID MICE WITH DISSEMINATED LATE RAMOS B LYMPHOMA
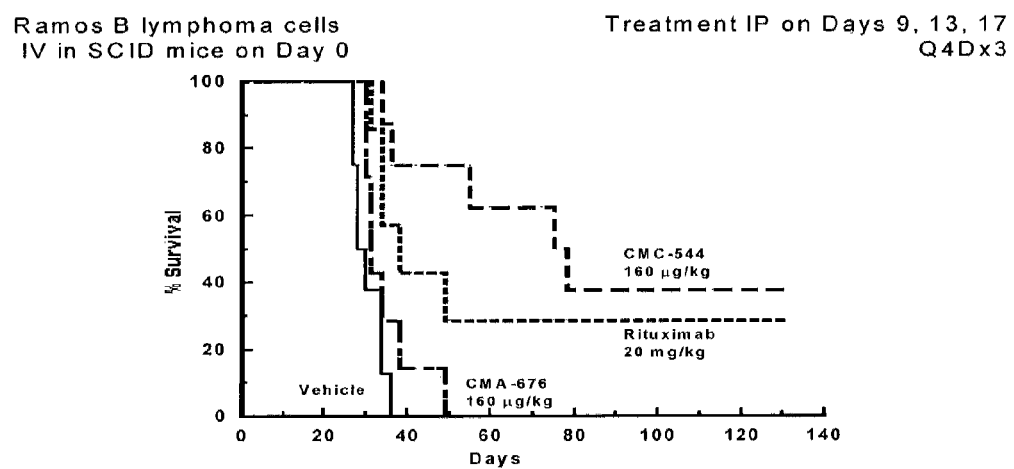

FIGURE 25: EFFECT OF CMC-544, RITUXIMAB (RITUXAN™), AND CMA-676 ON SURVIVAL OF SCID MICE WITH DISSEMINATED LATE RAMOS B LYMPHOMA
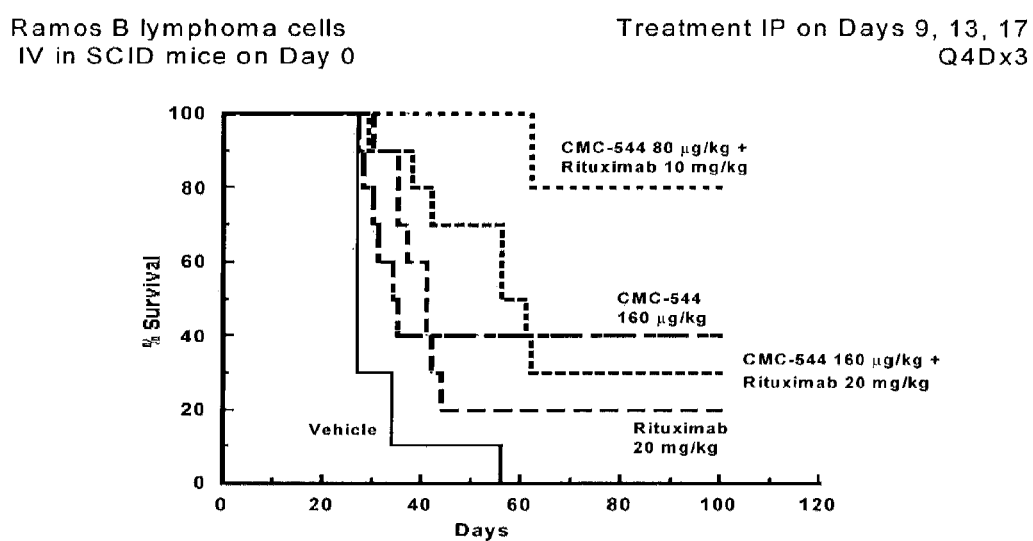

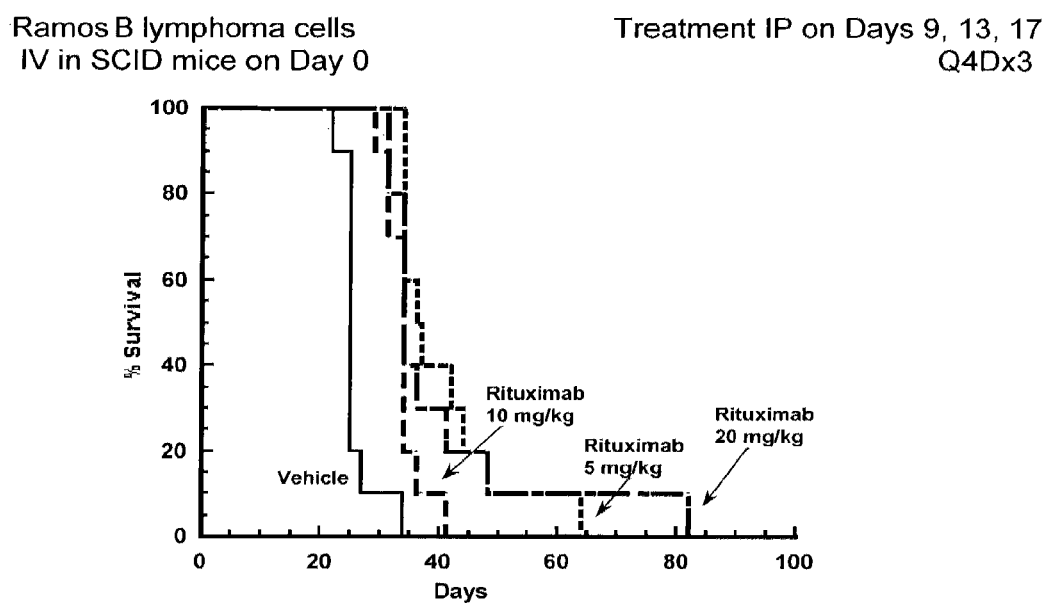
FIGURE 26: EFFECT OF CMC-544, RITUXIMAB (RITUXAN™), AND CMA-676 ON SURVIVAL OF SCID MICE WITH DISSEMINATED LATE RAMOS B LYMPHOMA FIGURE 27: EFFECT OF CMC-544, RITUXIMAB (RITUXAN™), AND CMA-676 ON SURVIVAL OF SCID MICE WITH DISSEMINATED LATE RAMOS B LYMPHOMA
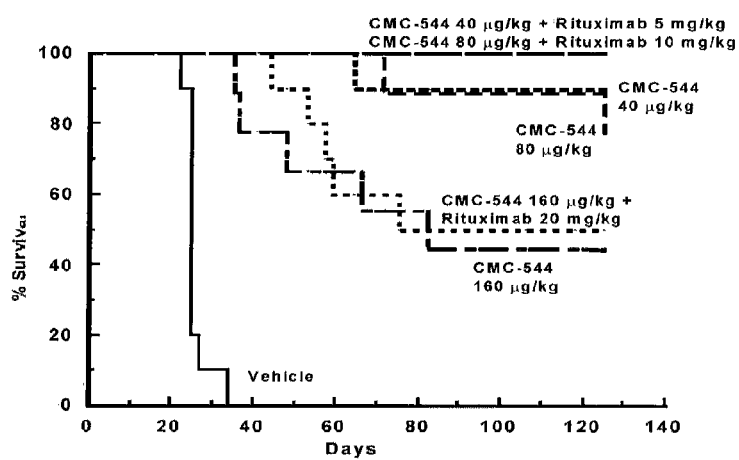

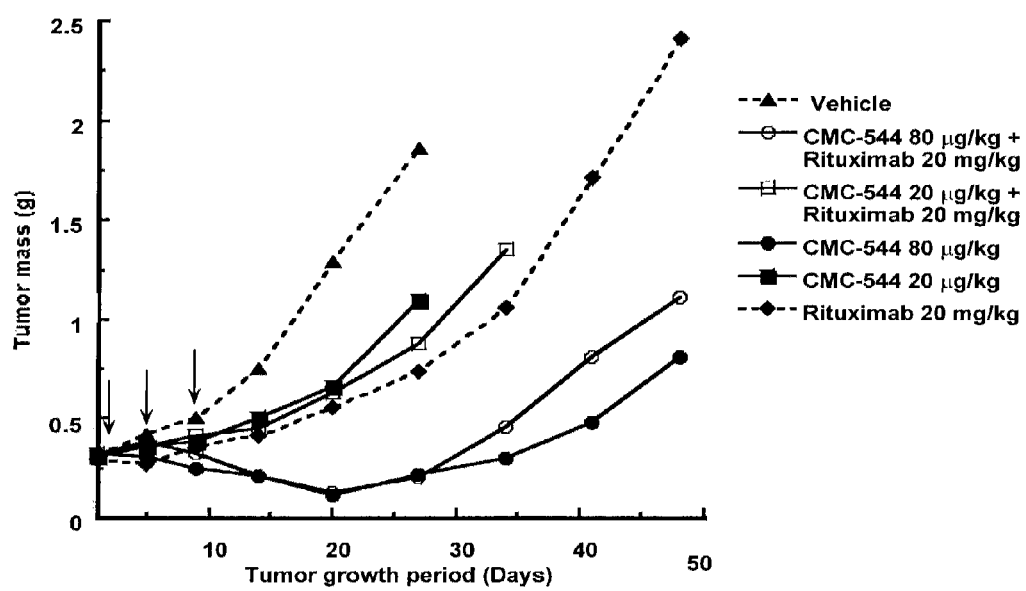
FIGURE 28: ANTI-TUMOR ACTIVITY OF CMC-544 WITH/WITHOUT RITUXIMAB (RITUXAN™) ON RL NON-HODGKINS LYMPHOMA FIGURE 29: ANTI-TUMOR ACTIVITY OF CMC-544 AND CHOP ON RL NON-HODGKINS LYMPHOMA
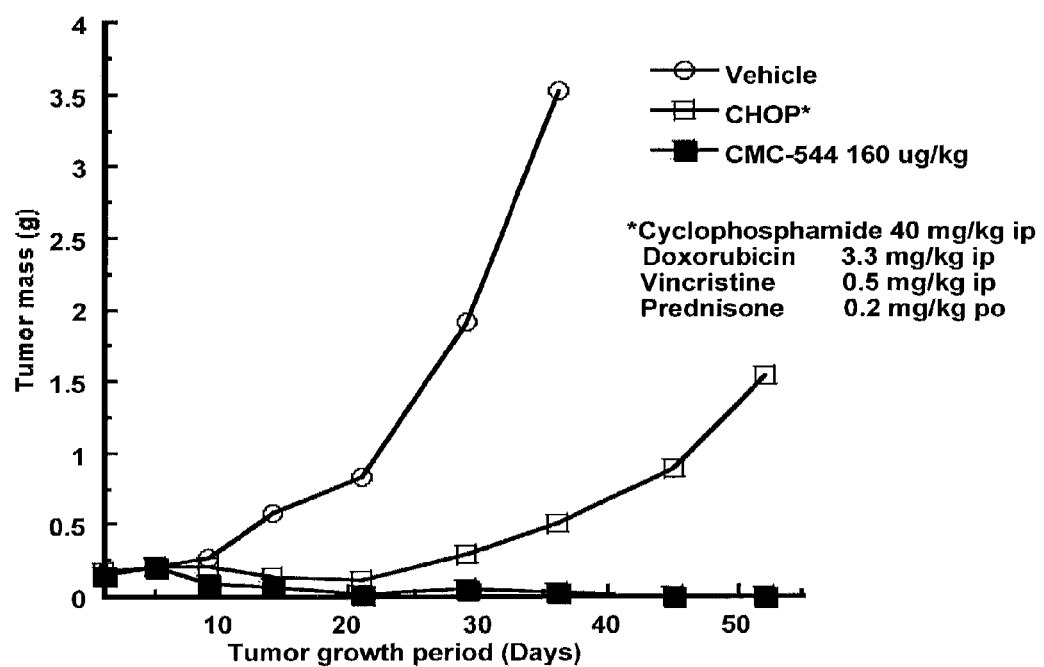

CALICHEAMICIN DERIVATIVE-CARRIER CONJUGATES

CROSS-REFERENCE TO RELATED APPLICATIONS

This is a continuation of U.S. patent application Ser. No. 10/428,894, filed May 2, 2003, which issued as U.S. Pat. No. 8,153,768 on Apr. 10, 2012, which claims the benefit of U.S. Provisional Application No. 60/377,440, filed May 2, 2002.

FIELD OF THE INVENTION

The present invention relates to methods for the production of monomeric cytotoxic drug/carrier conjugates (the "conjugates") with higher drug loading and substantially reduced low conjugate fraction (LCF). Particularly, the invention relates to anti-CD22 antibody-monomeric calicheamicin conjugates. The invention also relates to the conjugates of the invention, to methods of purification of the conjugates, to pharmaceutical compositions comprising the conjugates, and to uses of the conjugates.

BACKGROUND OF THE INVENTION

Drug conjugates developed for systemic pharmacotherapy are target-specific cytotoxic agents. The concept involves coupling a therapeutic agent to a carrier molecule with specificity for a defined target cell population. Antibodies with high affinity for antigens are a natural choice as targeting moieties. With the availability of high affinity monoclonal antibodies, the prospects of antibody-targeting therapeutics have become promising. Toxic substances that have been conjugated to monoclonal antibodies include toxins, low-molecular-weight cytotoxic drugs, biological response modifiers, and radionuclides. Antibody-toxin conjugates are frequently termed immunotoxins, whereas immunoconjugates consisting of antibodies and low-molecular-weight drugs such as methothrexate and ADRIAMYCIN® are called chemoimmunoconjugates. Immunomodulators contain biological response modifiers that are known to have regulatory functions such as lymphokines, growth factors, and complement-activating cobra venom factor (CVF). Radioimmunoconjugates consist of radioactive isotopes, which may be used as therapeutics to kill cells by their radiation or used for imaging. Antibody-mediated specific delivery of cytotoxic drugs to tumor cells is expected to not only augment their anti-tumor efficacy, but also prevent nontargeted uptake by normal tissues, thus increasing their therapeutic indices.

The present invention relates to immunoconjugates comprising an antibody as a targeting vehicle and having specificity for antigenic determinants on the surface of malignant cells conjugated to a cytotoxic drug. The invention relates to cytotoxic drug-antibody conjugates, wherein the antibody has specificity for antigenic determinants on B-malignancies, lymphoproliferative disorders and chronic inflammatory diseases. The present invention also relates to methods for producing immunoconjugates and to their therapeutic use(s).

A number of antibody-based therapeutics for treating a variety of diseases including cancer and rheumatoid arthritis have been approved for clinical use or are in clinical trials for a variety of malignancies including B-cell malignancies such as Non-Hodgkin's lymphoma. One such antibody-based therapeutic is rituximab (RITUXAN®), an unlabelled chimeric human γ1 (+my1V-region) antibody, which is specific for cell surface antigen CD20, which is expressed on B-cells. These antibody based therapeutics rely either on complement-mediated cytotoxicity (CDCC) or antibody-dependent cellular cytotoxicity (ADCC) against B cells, or on the use of radionuclides, such as $^{131}$I or $^{90}$Y, which have associated preparation and use problems for clinicians and patients. Consequently, there is a need for the generation of immunoconjugates which can overcome the shortcomings of current antibody-based therapeutics to treat a variety of malignancies including hematopoietic malignancies like non-Hodgkin's lymphoma (NHL), which can be produced easily and efficiently, and which can be used repeatedly without inducing an immune response.

Immunoconjugates comprising a member of the potent family of antibacterial and antitumor agents, known collectively as the calicheamicins or the LL-E33288 complex, (see U.S. Pat. No. 4,970,198 (1990)), were developed for use in the treatment of myelomas. The most potent of the calicheamicins is designated $\gamma_1$, which is herein referenced simply as gamma. These compounds contain a methyltrisulfide that can be reacted with appropriate thiols to form disulfides, at the same time introducing a functional group such as a hydrazide or other functional group that is useful in attaching a calicheamicin derivative to a carrier. (See U.S. Pat. No. 5,053,394). The use of the monomeric calicheamicin derivative/carrier conjugates in developing therapies for a wide variety of cancers has been limited both by the availability of specific targeting agents (carriers) as well as the conjugation methodologies which result in the formation of protein aggregates when the amount of the calicheamicin derivative that is conjugated to the carrier (i.e., the drug loading) is increased. Since higher drug loading increases the inherent potency of the conjugate, it is desirable to have as much drug loaded on the carrier as is consistent with retaining the affinity of the carrier protein. The presence of aggregated protein, which may be nonspecifically toxic and immunogenic, and therefore must be removed for therapeutic applications, makes the scale-up process for the production of these conjugates more difficult and decreases the yield of the products. The amount of calicheamicin loaded on the carrier protein (the drug loading), the amount of aggregate that is formed in the conjugation reaction, and the yield of final purified monomeric conjugate that can be obtained are all related. A compromise must therefore be made between higher drug loading and the yield of the final monomer by adjusting the amount of the reactive calicheamicin derivative that is added to the conjugation reaction.

The tendency for cytotoxic drug conjugates, especially calicheamicin conjugates to aggregate is especially problematic when the conjugation reactions are performed with the linkers described in U.S. Pat. No. 5,877,296 and U.S. Pat. No. 5,773,001, which are incorporated herein in their entirety. In this case, a large percentage of the conjugates produced are in an aggregated form, and it is quite difficult to purify conjugates made by these original processes (CMA process) for therapeutic use. For some carrier proteins, conjugates with even modest loadings are virtually impossible to make except on a small scale. Consequently, there is a critical need to improve methods for conjugating cytotoxic drugs, such as the calicheamicins, to carriers that minimize the amount of aggregation and thereby allow for as high a drug loading as possible with a reasonable yield of product.

Previously, conjugation methods for preparing monomeric calicheamicin derivative/carrier with higher drug loading/yield and decreased aggregation were disclosed (see U.S. Pat. No. 5,712,374 and U.S. Pat. No. 5,714,586, incorporated herein in their entirety). Although these processes resulted in conjugate preparations with substantially reduced aggregate content, it was discovered later that it produced conjugates containing undesirably high levels (45-65% HPLC Area %) of a low conjugated fraction (LCF), a fraction consisting mostly of unconjugated antibody. The presence of the LCF in the product is an inefficient use of the antibody, as it does not contain the cytotoxic drug. It may also compete with the calicheamicin-carrier conjugate for the target and potentially reduce the targetability of the latter resulting in reduced efficacy of the cytotoxic drug. Therefore, an improved conjugation process that would result in significantly lower levels of the LCF and have acceptable levels of aggregation, without significantly altering the physical properties of the conjugate, is desirable.

SUMMARY OF THE INVENTION

The present invention relates to methods for the production of monomeric cytotoxic drug derivative/carrier conjugates (the "conjugates") with higher loading and substantially reduced low conjugate fraction (LCF). Particularly, the invention relates to the production of monomeric calicheamicin derivative-carrier conjugates, to the conjugates, to compositions, to a method of purification of the conjugates, and to use of the conjugates. More particularly, the invention relates to methods for producing a monomeric calicheamicin derivative-anti-CD22 antibody conjugate (CMC-544).

In one embodiment, the present invention discloses an improved conjugation process for the production of the conjugates that resulted in significantly lower levels of the LCF (below 10 percent) without any significant alteration of the physical or chemical properties. The invention also discloses a further improvement to the conjugation process which results in not only a significant reduction in the levels of the LCF, but also results in a significant reduction in aggregation from previously disclosed processes, and produces substantially increased drug loading. The conjugates of the present invention have the formula:

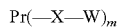

wherein:
Pr is a proteinaceous carrier,
X is a linker that comprises a product of any reactive group that can react with a proteinaceous carrier,
W is a cytotoxic drug;
m is the average loading for a purified conjugation product such that the cytotoxic drug constitutes 7-9% of the conjugate by weight; and
$(-X-W)_m$ is a cytotoxic drug derivative.

The conjugates of the present invention, in one embodiment, are generated by the method of the invention comprising the steps of: (1) adding the cytotoxic drug derivative to the proteinaceous carrier wherein the cytotoxic drug derivative is 4.5-11% by weight of the proteinaceous carrier; (2) incubating the cytotoxic drug derivative and a proteinaceous carrier in a non-nucleophilic, protein-compatible, buffered solution having a pH in a range from about 7 to 9 to produce a monomeric cytotoxic drug/carrier conjugate, wherein the solution further comprises (a) an organic cosolvent, and (b) an additive comprising at least one $C_6$-$C_{18}$ carboxylic acid or its salt, and wherein the incubation is conducted at a temperature ranging from about 30° C. to about 35° C. for a period of time ranging from about 15 minutes to 24 hours; and (3) subjecting the conjugate produced in step (2) to a chromatographic separation process to separate the monomeric cytotoxic drug derivative/proteinaceous carrier conjugates with a loading in the range of 4-10% by weight of cytotoxic drug and with low conjugated fraction (LCF) below 10 percent from unconjugated proteinaceous carrier, cytotoxic drug derivative, and aggregated conjugates.

In one aspect of the invention, the proteinaceous carrier of the conjugate is selected from a group consisting of hormones, growth factors, antibodies, antibody fragments, antibody mimics, and their genetically or enzymatically engineered counterparts.

In one embodiment, the proteinaceous carrier is an antibody. In a preferred embodiment, the antibody is selected from a group consisting of a monoclonal antibody, a chimeric antibody, a human antibody, a humanized antibody, a single chain antibody, a Fab fragment and a $F(ab)_2$ fragment.

In another embodiment, the humanized antibody is directed against the cell surface antigen CD22.

In a preferred embodiment, the humanized anti-CD22 antibody is a CDR-grafted antibody, and comprises a light chain variable region 5/44-gL1 (SEQ ID NO:19), and a heavy chain variable region 5/44-gH7 (SEQ ID NO:27).

In another preferred embodiment, the humanized anti-CD22 antibody is a CDR-grafted antibody comprising a light chain having a sequence set forth in SEQ ID NO:28.

In yet another preferred embodiment, the humanized anti-CD22 antibody is a CDR-grafted antibody comprising a heavy chain having a sequence set forth in SEQ ID NO:30.

In another preferred embodiment, the humanized anti-CD22 antibody is a CDR-grafted antibody comprising a light chain having a sequence set forth in SEQ ID NO:28 and a heavy chain having a sequence set forth in SEQ ID NO:30.

In another embodiment, the humanized anti-CD22 antibody is a CDR-grafted antibody that is a variant antibody obtained by an affinity maturation protocol and has increased affinity for human CD22.

In another aspect, the cytotoxic drug used to generate the monomeric cytotoxic drug/carrier conjugate of the present invention is either an inhibitor of tubulin polymerization, an alkylating agent that binds to and disrupts DNA, an inhibitor protein synthesis, or an inhibitor of tyrosine kinases.

In one embodiment, the cytotoxic drug is selected from calicheamicins, thiotepa, taxanes, vincristine, daunorubicin, doxorubicin, epirubicin, esperamicins, actinomycin, authramycin, azaserines, bleomycins, tamoxifen, idarubicin, dolastatins/auristatins, hemiasterlins, and maytansinoids.

In a preferred embodiment, the cytotoxic drug is calicheamicin. In a particularly preferred embodiment, the calicheamicin is gamma calicheamicin or N-acetyl gamma calicheamicin derivative.

In yet another aspect, the cytotoxic drug is functionalized with 3-mercapto-3-methyl butanoyl hydrazide and conjugated to a proteinaceous carrier via a hydrolyzable linker that is capable of releasing the cytotoxic drug from the conjugate after binding and entry into target cells. In a preferred embodiment of this aspect, the hydrolyzable linker is 4-(4-acetylphenoxy) butanoic acid (AcBut).

In yet another aspect of the invention, octanoic acid or its salt, or decanoic acid or its salt is used as an additive during the conjugation process to decrease aggregation and increase drug loading.

In yet another aspect of the invention, the conjugates of the invention are purified by a chromatographic separation process.

In one embodiment, the chromatographic separation process used to separate the monomeric drug derivative-carrier conjugate is size exclusion chromatography (SEC).

In another embodiment, the chromatographic separation process used to separate the monomeric drug derivative-carrier conjugate is HPLC, FPLC or SEPHACRYL™ S-200 chromatography.

In a preferred embodiment, the chromatographic separation process used to separate the monomeric drug derivative-carrier conjugate is hydrophobic interaction chromatography (HIC). In a particularly preferred embodiment, HIC is carried out using Phenyl SEPHAROSE™ 6 Fast Flow chromatographic medium, Butyl SEPHAROSE™ 4 Fast Flow chromatographic medium, Octyl SEPHAROSE™ 4 Fast Flow chromatographic medium, TOYOPEARL® Ether-650M chromatographic medium, MACRO-PREP® methyl HIC medium or MACRO-PREP® t-Butyl HIC medium. In a more particularly preferred embodiment, HIC is carried out using Butyl SEPHAROSE™ 4 Fast Flow chromatographic medium.

In another aspect, the invention is directed to a monomeric cytotoxic drug derivative/carrier conjugate produced by the method of the invention. In a preferred embodiment of this aspect, the cytotoxic drug used is calicheamicin and the carrier used is an antibody.

In another preferred embodiment, the antibody is selected from a group consisting of a monoclonal antibody, a chimeric antibody, a human antibody, a humanized antibody, a single chain antibody, a Fab fragment and a F(ab)$_2$ fragment.

In a more particularly preferred aspect, a humanized antibody directed against the cell surface antigen CD22 is used.

In one embodiment, the humanized anti-CD22 antibody is a CDR-grafted antibody, and comprises a light chain variable region 5/44-gL1 (SEQ ID NO:19), and a heavy chain variable region 5/44-gH7 (SEQ ID NO:27).

In another embodiment, the humanized anti-CD22 antibody is a CDR-grafted antibody comprising a light chain having a sequence set forth in SEQ ID NO:28.

In a preferred embodiment, the humanized anti-CD22 antibody is a CDR-grafted antibody comprising a heavy chain having a sequence set forth in SEQ ID NO:30.

In another preferred embodiment, the humanized anti-CD22 antibody is a CDR-grafted antibody comprising a light chain having a sequence set forth in SEQ ID NO:28 and a heavy chain having a sequence set forth in SEQ ID NO:30.

In still another embodiment, the humanized anti-CD22 antibody is a CDR-grafted antibody that is a variant antibody obtained by an affinity maturation protocol which has increased affinity for human CD22.

In a preferred embodiment, the calicheamicin is gamma calicheamicin or N-acetyl gamma calicheamicin.

In one embodiment, the calicheamicin derivative is functionalized with 3-mercapto-3-methyl butanoyl hydrazide.

In another embodiment, the linker used to conjugate the drug to the carrier is a hydrolyzable linker that is capable of releasing the cytotoxic drug from the conjugate after binding and entry into target cells. In a preferred embodiment, the hydrolyzable linker is 4-(4-acetylphenoxy)butanoic acid (AcBut).

Another aspect of the invention is directed to a monomeric calicheamicin derivative/anti-CD22 antibody conjugate having the formula, Pr(—X—S—S—W)$_m$ wherein: Pr is an anti-CD22 antibody; X is a hydrolyzable linker that comprises a product of any reactive group that can react with an antibody; W is a calicheamicin radical; m is the average loading for a purified conjugation product such that the calicheamicin constitutes 4-10% of the conjugate by weight; and (—X—S—S—W)$_m$ is a calicheamicin derivative generated by the process of the invention.

In one embodiment of this aspect, the antibody is selected from a group consisting of a monoclonal antibody, a chimeric antibody, a human antibody, a humanized antibody, a single chain antibody, a Fab fragment and a F(ab)$_2$ fragment.

In a preferred embodiment, the antibody is an anti-CD22 antibody that has specificity for human CD22, and comprises a heavy chain wherein the variable domain comprises a CDR having at least one of the sequences given as H1 in FIG. 1 (SEQ ID NO:1) for CDR-H1, as H2 in FIG. 1 (SEQ ID NO:2) or H2' (SEQ ID NO:13) or H2'' (SEQ ID NO:15) or H2''' (SEQ ID NO:16) for CDR-H2, or as H3 in FIG. 1 (SEQ ID NO:3) for CDR-H3, and comprises a light chain wherein the variable domain comprises a CDR having at least one of the sequences given as L1 in FIG. 1 (SEQ ID NO:4) for CDR-L1, as L2 in FIG. 1 (SEQ ID NO:5) for CDR-L2, or as L3 in FIG. 1 (SEQ ID NO:6) for CDR-L3.

In another preferred embodiment, the anti-CD22 antibody comprises a heavy chain wherein the variable domain comprises a CDR having at least one of the sequences given in SEQ ID NO:1 for CDR-H1, SEQ ID NO:2 or SEQ ID NO:13 or SEQ ID NO:15 or SEQ ID NO:16 for CDR-H2, or SEQ ID NO:3 for CDR-H3, and a light chain wherein the variable domain comprises a CDR having at least one of the sequences given in SEQ ID NO:4 for CDR-L1, SEQ ID NO:5 for CDR-L2, or SEQ ID NO:6 for CDR-L3.

In yet another preferred embodiment, the anti-CD22 antibody comprises SEQ ID NO:1 for CDR-H1, SEQ ID NO: 2 or SEQ ID NO:13 or SEQ ID NO:15 or SEQ ID NO:16 for CDR-H2, SEQ ID NO:3 for CDR-H3, SEQ ID NO:4 for CDR-L1, SEQ ID NO:5 for CDR-L2, and SEQ ID NO:6 for CDR-L3.

In another embodiment, the humanized anti-CD22 antibody is a CDR-grafted anti-CD22 antibody and comprises a variable domain comprising human acceptor framework regions and non-human donor CDRs.

In another embodiment, the humanized anti-CD22 antibody has a human acceptor framework wherein regions of the variable domain of the heavy chain of the antibody are based on a human sub-group I consensus sequence and comprise non-human donor residues at positions 1, 28, 48, 71 and 93. In another embodiment, the humanized antibody further comprises non-human donor residues at positions 67 and 69.

In one preferred embodiment, the CDR-grafted humanized antibody comprises a variable domain of the light chain comprising a human acceptor framework region based on a human sub-group I consensus sequence and further comprising non-human donor residues at positions 2, 4, 37, 38, 45 and 60. In another embodiment, the CDR-grafted antibody further comprises a non-human donor residue at position 3.

In yet another embodiment, the CDR-grafted antibody comprises a light chain. variable region 5/44-gL1 (SEQ ID NO:19) and a heavy chain variable region 5/44-gH7 (SEQ ID NO:27).

In another embodiment, the CDR-grafted antibody comprises a light chain having the sequence as set forth in SEQ ID NO:28 and a heavy chain having the sequence as set forth in SEQ ID NO:30.

In yet another embodiment, the CDR-grafted antibody comprises a light chain having the sequence as set forth in SEQ ID NO:28 and a heavy chain having the sequence as set forth in SEQ ID NO:30.

In one embodiment, the anti-CD22 CDR-grafted antibody is a variant antibody obtained by an affinity maturation protocol and has increased affinity for human CD22.

In another embodiment, the anti-CD22 antibody is a chimeric antibody comprising the sequences of the light and heavy chain variable domains of the monoclonal antibody set forth in SEQ ID NO:7 and SEQ ID NO:8, respectively.

In yet another embodiment, the anti-CD22 antibody comprises a hybrid CDR with a truncated donor CDR sequence wherein the missing portion of the donor CDR is replaced by a different sequence and forms a functional CDR.

In a particularly preferred embodiment, the cytotoxic drug derivative is either a gamma calicheamicin or a N-acetyl gamma calicheamicin derivative.

In another aspect, the invention is directed to a method for the preparation of a stable lyophilized composition of a monomeric cytotoxic drug derivative/carrier conjugate. In a preferred embodiment, the stable lyophilized composition of the monomeric cytotoxic drug derivative/carrier conjugate is prepared by (a) dissolving the monomeric cytotoxic drug derivative/carrier conjugate to a final concentration of 0.5 to 2 mg/ml in a solution comprising a cryoprotectant at a concentration of 1.5%-5% by weight, a polymeric bulking agent at a concentration of 0.5-1.5% by weight, electrolytes at a concentration of 0.01 M to 0.1 M, a solubility facilitating agent at a concentration of 0.005-0.05% by weight, buffering agent at a concentration of 5-50 mM such that the final pH of the solution is 7.8-8.2, and water; (b) dispensing the above solution into vials at a temperature of +5° C. to +10° C.; (c) freezing the solution at a freezing temperature of −35° C. to −50° C.; (d) subjecting the frozen solution to an initial freeze drying step at a primary drying pressure of 20 to 80 microns at a shelf temperature at −10° C. to −40° C. for 24 to 78 hours; and (e) subjecting the freeze-dried product of step (d) to a secondary drying step at a drying pressure of 20 to 80 microns at a shelf temperature of +10° C. to +35° C. for 15 to 30 hours.

In one embodiment, the cryoprotectant used in the lyophilization of the cytotoxic drug/carrier conjugate is selected from alditol, mannitol, sorbitol, inositol, polyethylene glycol, aldonic acid, uronic acid, aldaric acid, aldoses, ketoses, amino sugars, alditols, inositols, glyceraldehydes, arabinose, lyxose, pentose, ribose, xylose, galactose, glucose, hexose, idose, mannose, talose, heptose, glucose, fructose, gluconic acid, sorbitol, lactose, mannitol, methyl α-glucopyranoside, maltose, isoascorbic acid, ascorbic acid, lactone, sorbose, glucaric acid, erythrose, threose, arabinose, allose, altrose, gulose, idose, talose, erythrulose, ribulose, xylulose, psicose, tagatose, glucuronic acid, gluconic acid, glucaric acid, galacturonic acid, mannuronic acid, glucosamine, galactosamine, sucrose, trehalose, neuraminic acid, arabinans, fructans, fucans, galactans, galacturonans, glucans, mannans, xylans, levan, fucoidan, carrageenan, galactocarolose, pectins, pectic acids, amylose, pullulan, glycogen, amylopectin, cellulose, dextran, pustulan, chitin, agarose, keratin, chondroitin, dermatan, hyaluronic acid, alginic acid, xanthan gum, starch, sucrose, glucose, lactose, trehalose, ethylene glycol, polyethylene glycol, polypropylene glycol, glycerol, and pentaerythritol.

In a preferred embodiment, the cryoprotectant is sucrose, which is present at a concentration of 1.5% by weight. In one embodiment, the polymeric bulking agent used during the lyophilization process is selected from Dextran 40 or hydroxyethyl starch 40, and is at a concentration of 0.9% by weight.

In another embodiment, the electrolyte used in the lyophilization solution is sodium chloride, which is present at a concentration of 0.05 M.

In a preferred embodiment, a solubility-facilitating agent is used during the lyophilization process. Preferably, this solubility-facilitating agent is a surfactant. In a particularly preferred embodiment, the surfactant is polysorbate 80, which is present at a concentration of 0.01% by weight.

In one embodiment, the buffering agent used is tromethamine, which is present at a concentration of 0.02 M. It is preferable for the pH of the solution to be 8.0 at the start of the lyophilization process. The solution containing the cytotoxic drug/carrier conjugate is dispensed into vials at a temperature of +5° C. prior to the start of the process.

In a preferred embodiment, the solution in the vials is frozen at a temperature of −45° C.; the frozen solution is subjected to an initial freeze drying step at a primary drying pressure of 60 microns and at a shelf temperature of −30° C. for 60 hours; and the freeze-dried product is subjected to a secondary drying step at a drying pressure of 60 microns at a shelf temperature of +25° C. for 24 hours.

Another aspect of the invention is directed to a composition comprising a therapeutically effective dose of a monomeric cytotoxic drug derivative/carrier conjugate prepared by a method of the invention.

In one embodiment, the carrier in the monomeric cytotoxic drug derivative/carrier conjugate is a proteinaceous carrier selected from hormones, growth factors, antibodies and antibody mimics.

In a preferred embodiment, the proteinaceous carrier is a human monoclonal antibody, a chimeric antibody, a human antibody or a humanized antibody.

In a preferred embodiment, the humanized antibody is directed against the cell surface antigen CD22.

In a particularly preferred, embodiment of this aspect of the invention, the anti-CD22 antibody has specificity for human CD22, and comprises a heavy chain wherein the variable domain comprises a CDR having at least one of the sequences given as H1 in FIG. 1 (SEQ ID NO:1) for CDR-H1, as H2 in FIG. 1 (SEQ ID NO:2) or H2' (SEQ ID NO:13) or H2'' (SEQ ID NO:15) or H2''' (SEQ ID NO:16) for CDR-H2, or as H3 in FIG. 1 (SEQ ID NO:3) for CDR-H3, and comprises a light chain wherein the variable domain comprises a CDR having at least one of the sequences given as L1 in FIG. 1 (SEQ ID NO:4) for CDR-L1, as L2 in FIG. 1 (SEQ ID NO:5) for CDR-L2, or as L3 in FIG. 1 (SEQ ID NO:6) for CDR-L3.

In another preferred embodiment, anti-CD22 antibody has a heavy chain wherein the variable domain comprises a CDR having at least one of the sequences given in SEQ ID NO:1 for CDR-H1, SEQ ID NO:2 or SEQ ID NO:13 or SEQ ID NO:15 or SEQ ID NO:16 for CDR-H2, or SEQ ID NO:3 for CDR-H3, and a light chain wherein the variable domain comprises a CDR having at least one of the sequences given in SEQ ID NO:4 for CDR-L1, SEQ ID NO:5 for CDR-L2, or SEQ ID NO:6 for CDR-L3.

In yet another preferred embodiment, the anti-CD22 antibody comprises SEQ ID NO:1 for CDR-H1, SEQ ID NO: 2 or SEQ ID NO:13 or SEQ ID NO:15 or SEQ ID NO:16 for CDR-H2, SEQ ID NO:3 for CDR-H3, SEQ ID NO:4 for CDR-L1, SEQ ID NO:5 for CDR-L2, and SEQ ID NO:6 for CDR-L3.

In a particularly preferred embodiment, the humanized anti-CD22 antibody is a CDR-grafted humanized anti-CD22 antibody and comprises a light chain variable region 5/44-gL1 (SEQ ID NO:19), and a heavy chain variable region 5/44-gH7 (SEQ ID NO:27).

In another particularly preferred embodiment, the humanized anti-CD22 antibody is a CDR-grafted antibody having specificity for human CD22 and comprises a light chain having a sequence set forth in SEQ ID NO:28 and a heavy chain having a sequence set forth in SEQ ID NO:30.

In one embodiment, the CDR-grafted antibody is a variant antibody which has increased affinity for human CD22, and the antibody is obtained by an affinity maturation protocol.

In one embodiment, the monomeric cytotoxic drug is calicheamicin and is preferably selected from gamma calicheamicin or N-acetyl calicheamicin.

In one embodiment, the composition may optionally contain an additional bioactive agent. Such a bioactive agent may be a cytotoxic drug, a growth factor or a hormone.

Yet another aspect of the invention is directed to a method of treating a subject with a proliferative disorder by administering to the subject a therapeutically effective dose of the composition of the invention. The composition may be administered subcutaneously, intraperitoneally, intravenously, intraarterially, intramedullarly, intrathecally, transdermally, transcutaneously, intranasally, topically, entereally, intravaginally, sublingually or rectally. In a preferred embodiment, the composition of the invention is administered intravenously.

In one embodiment, the composition is administered to a human subject suffering from a proliferative disorder such as cancer. In a preferred embodiment, the cancer is a B-cell malignancy. The B-cell malignancy may be a leukemia or lymphoma that express cell surface antigen CD22.

In yet another embodiment, the cancer is a carcinoma or a sarcoma.

Another aspect of the present invention is directed to a method of treating a B-cell malignancy by administering to a patient with such malignancy a therapeutically effective composition comprising a cytotoxic drug-anti-CD22-antibody conjugate of the invention. In a preferred embodiment, the B-cell malignancy is a lymphoma, particularly Non-Hodgkin's lymphoma.

In one embodiment, the cytotoxic drug used to prepare the conjugates of the present invention is selected from the group consisting of calicheamicins, thiotepa, taxanes, vincristine, daunorubicin, doxorubicin, epirubicin, actinomycin, authramycin, azaserines, bleomycins, tamoxifen, idarubicin, dolastatins/auristatins, hemiasterlins, maytansinoids, and esperamicins.

In a preferred embodiment, the cytotoxic drug is gamma calicheamicin or N-acetyl calicheamicin.

In another embodiment, the treatment comprises administering the cytotoxic drug conjugate of the invention with one or more bioactive agents selected from antibodies, growth factors, hormones, cytokines, anti-hormones, xanthines, interleukins, interferons, and cytotoxic drugs.

In a preferred embodiment, the bioactive agent is an antibody, and is directed against a cell surface antigen expressed on B-cell malignancies. In a further preferred embodiment, the antibody directed against cell surface antigens expressed on B-cell malignancies is selected from a group consisting of anti-CD19, anti-CD20 and anti-CD33 antibodies. Such antibodies include the anti-CD20 antibody, rituximab (RITUXAN®).

In another embodiment, the bioactive agents are cytokines or growth factors and include, but are not limited to, interleukin 2 (IL-2), TNF, CSF, GM-CSF and G-CSF.

In another embodiment, bioactive agents are hormones and include estrogens, androgens, progestins, and corticosteroids.

In yet another embodiment, the bioactive agent is a cytotoxic drug selected from doxorubicin, daunorubicin, idarubicin, aclarubicin, zorubicin, mitoxantrone, epirubicin, carubicin, nogalamycin, menogaril, pitarubicin, valrubicin, cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, tiazofurin, adriamycin, cisplatin, carboplatin, cyclophosphamide, dacarbazine, vinblastine, vincristine, mitoxantrone, bleomycin, mechlorethamine, prednisone, procarbazine methotrexate, fluorouracils, etoposide, taxol, taxol analogs, and mitomycin.

In a preferred embodiment, the therapeutically effective composition of the cytotoxic drug-anti-CD22-antibody conjugate is administered together with one or more combinations of cytotoxic agents as a part of a treatment regimen, wherein the combination of cytotoxic agents is selected from: CHOPP (cyclophosphamide, doxorubicin, vincristine, prednisone, and procarbazine); CHOP (cyclophosphamide, doxorubicin, vincristine, and prednisone); COP (cyclophosphamide, vincristine, and prednisone); CAP-BOP (cyclophosphamide, doxorubicin, procarbazine, bleomycin, vincristine, and prednisone); m-BACOD (methotrexate, bleomycin, doxorubicin, cyclophosphamide, vincristine, dexamethasone, and leucovorin); ProMACE-MOPP (prednisone, methotrexate, doxorubicin, cyclophosphamide, etoposide, leucovorin, mechloethamine, vincristine, prednisone, and procarbazine); ProMACE-CytaBOM (prednisone, methotrexate, doxorubicin, cyclophosphamide, etoposide, leucovorin, cytarabine, bleomycin, and vincristine); MACOP-B (methotrexate, doxorubicin, cyclophosphamide, vincristine, prednisone, bleomycin, and leucovorin); MOPP (mechloethamine, vincristine, prednisone, and procarbazine); ABVD (ADRIAMYCIN®/doxorubicin, bleomycin, vinblastine, and dacarbazine); MOPP (mechloethamine, vincristine, prednisone, and procarbazine) alternating with ABV (ADRIAMYCIN®/doxorubicin, bleomycin, and vinblastine); MOPP (mechloethamine, vincristine, prednisone, and procarbazine) alternating with ABVD (ADRIAMYCIN®/doxorubicin, bleomycin, vinblastine, and dacarbazine), Ch1VPP (chlorambucil, vinblastine, procarbazine, and prednisone); IMVP-16 (ifosfamide, methotrexate, and etoposide); MIME (methyl-gag, ifosfamide, methotrexate, and etoposide); DHAP (dexamethasone, high-dose cytaribine, and cisplatin); ESHAP (etoposide, methylpredisolone, high-dose cytarabine, and cisplatin); CEPP(B) (cyclophosphamide, etoposide, procarbazine, prednisone, and bleomycin); CAMP (lomustine, mitoxantrone, cytarabine, and prednisone); and CVP-1 (cyclophosphamide, vincristine, and prednisone).

In a preferred embodiment, the therapeutically effective composition of the cytotoxic drug-anti-CD22-antibody conjugate is administered prior to the administration of one or more of the above combinations of cytotoxic drugs. In another preferred embodiment, the therapeutically effective composition of the cytotoxic drug-anti-CD22-antibody conjugate is administered subsequent to the administration of one or more of the above combinations of cytotoxic drugs as a part of a treatment regimen.

Another aspect of the invention is directed to a method of treating aggressive lymphomas comprising administering to a patient in need of said treatment a therapeutically effective composition of a monomeric calicheamicin derivative-anti-CD22-antibody conjugate together with one or more bioactive agents.

Yet another aspect of the present invention is directed to the use of the composition of the invention in treating a subject with a proliferative disorder such as cancer. In particular, the cancer is a B-cell malignancy that expresses CD22 antigen on the cell surface. In particular, the B-cell malignancy is either a leukemia or a lymphoma. In one embodiment, the cancer is a carcinoma or a leukemia.

In one embodiment, a therapeutically effective dose of the composition is administered subcutaneously, intraperitoneally, intravenously, intraarterially, intramedullarly, intrathecally, transdermally, transcutaneously, intranasally, topically, entereally, intravaginally, sublingually or rectally.

In a preferred embodiment, the therapeutically effective dose of the pharmaceutical composition of the invention is administered intravenously.

Another aspect of the invention is directed to the use of a monomeric calicheamicin derivative/anti-CD22 antibody conjugate of the present invention for use in the treatment of a subject with a B-cell malignancy such as Non-Hodgkin's lymphoma. In one embodiment, the monomeric calicheamicin derivative/anti-CD22 antibody conjugate of the present invention is administered with one or more bioactive agents.

In one embodiment, the bioactive agents are selected from a group consisting of antibodies, growth factors, hormones, cytokines, anti-hormones, xanthines, interleukins, interferons, and cytotoxic drugs.

In a preferred embodiment, the bioactive agent is an antibody directed against a cell surface antigen expressed on B-cell malignancies, such as anti-CD19, anti-CD20 and anti-CD33 antibodies. In a preferred embodiment, the anti-CD20 antibody is rituximab (RITUXAN®).

In another embodiment, the bioactive agents include cytokines or growth factors such as interleukin 2 (IL-2), TNF, CSF, GM-CSF and G-CSF or hormones, which include estrogens, androgens, progestins, and corticosteroids.

In another embodiment, the bioactive agent is a cytotoxic drug selected from doxorubicin, daunorubicin, idarubicin, aclarubicin, zorubicin, mitoxantrone, epirubicin, carubicin, nogalamycin, menogaril, pitarubicin, valrubicin, cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, tiazofurin, adriamycin, cisplatin, carboplatin, cyclophosphamide, dacarbazine, vinblastine, vincristine, mitoxantrone, bleomycin, mechlorethamine, prednisone, procarbazine, methotrexate, fluorouracils, etoposide, taxol, taxol analogs, and mitomycin.

In a preferred embodiment, the therapeutically effective dose of the monomeric calicheamicin derivative/anti-CD22 antibody conjugate is administered together with one or more combinations of cytotoxic agents as a part of a treatment regimen, wherein the combination of cytotoxic agents is selected from: CHOPP (cyclophosphamide, doxorubicin, vincristine, prednisone, and procarbazine); CHOP (cyclophosphamide, doxorubicin, vincristine, and prednisone); COP (cyclophosphamide, vincristine, and prednisone); CAP-BOP (cyclophosphamide, doxorubicin, procarbazine, bleomycin, vincristine, and prednisone); m-BACOD (methotrexate, bleomycin, doxorubicin, cyclophosphamide, vincristine, dexamethasone, and leucovorin); ProMACE-MOPP (prednisone, methotrexate, doxorubicin, cyclophosphamide, etoposide, leucovorin, mechloethamine, vincristine, prednisone, and procarbazine); ProMACE-CytaBOM (prednisone, methotrexate, doxorubicin, cyclophosphamide, etoposide, leucovorin, cytarabine, bleomycin, and vincristine); MACOP-B (methotrexate, doxorubicin, cyclophosphamide, vincristine, prednisone, bleomycin, and leucovorin); MOPP (mechloethamine, vincristine, prednisone, and procarbazine); ABVD (ADRIAMYCIN®/doxorubicin, bleomycin, vinblastine, and dacarbazine); MOPP (mechloethamine, vincristine, prednisone and procarbazine) alternating with ABV (ADRIAMYCIN®/doxorubicin, bleomycin, and vinblastine); MOPP (mechloethamine, vincristine, prednisone, and procarbazine) alternating with ABVD (ADRIAMYCIN®/doxorubicin, bleomycin, vinblastine, and dacarbazine); Ch1VPP (chlorambucil, vinblastine, procarbazine, and prednisone); IMVP-16 (ifosfamide, methotrexate, and etoposide); MIME (methyl-gag, ifosfamide, methotrexate, and etoposide); DHAP (dexamethasone, high-dose cytaribine, and cisplatin); ESHAP (etoposide, methylpredisolone, high-dose cytarabine, and cisplatin); CEPP(B) (cyclophosphamide, etoposide, procarbazine, prednisone, and bleomycin); CAMP (lomustine, mitoxantrone, cytarabine, and prednisone); CVP-1 (cyclophosphamide, vincristine, and prednisone), ESHOP (etoposide, methylpredisolone, high-dose cytarabine, vincristine and cisplatin); EPOCH (etoposide, vincristine, and doxorubicin for 96 hours with bolus doses of cyclophosphamide and oral prednisone), ICE (ifosfamide, cyclophosphamide, and etoposide), CEPP(B) (cyclophosphamide, etoposide, procarbazine, prednisone, and bleomycin), CHOP-B (cyclophosphamide, doxorubicin, vincristine, prednisone, and bleomycin), CEPP-B (cyclophosphamide, etoposide, procarbazine, and bleomycin), and P/DOCE (epirubicin or doxorubicin, vincristine, cyclophosphamide, and prednisone).

In one preferred embodiment, the monomeric calicheamicin derivative/anti-CD22 antibody conjugate is administered prior to the administration of one or more combinations of cytotoxic agents as a part of a treatment regimen.

In another preferred embodiment, the therapeutically effective dose of the monomeric calicheamicin derivative/anti-CD22 antibody conjugate is administered subsequent to the administration of one or more combinations of cytotoxic agents as part of a treatment regimen.

In yet another preferred embodiment, the therapeutically effective dose of the monomeric calicheamicin derivative/anti-CD22 antibody conjugate is administered together with an antibody directed against a cell surface antigen on B-cell malignancies, and optionally comprising one or more combinations of cytotoxic agents as part of a treatment regimen.

In another aspect, the invention is directed to the use of the monomeric calicheamicin derivative/anti-CD22 antibody conjugate of the present invention in the manufacture of a medicament for the treatment of a proliferative disorder. Such a medicament can be used to treat B-cell proliferative disorders either alone or in combination with other bioactive agents.

BRIEF DESCRIPTION OF THE SEVERAL VIEWS OF THE DRAWINGS

FIG. 1 shows the amino acid sequence of the CDRs of mouse monoclonal antibody 5/44 (SEQ ID NOS:1 to 6).

FIG. 2 shows the DNA (SEQ ID NOS:52 and 53) and protein (SEQ ID NO:7) sequence of the light chain variable ($V_L$) domain of mouse monoclonal antibody 5/44.

FIG. 3 shows the DNA (SEQ ID NOS:54 and 55) and protein (SEQ ID NO:8) sequence of the heavy chain variable domain ($V_H$) of mouse monoclonal antibody 5/44.

FIG. 4 shows the strategy for removal of the glycosylation site and reactive lysine in CDR-H2 (SEQ ID NOS:9-12 and 14).

FIG. 5 shows the graft design for the 5/44 light chain sequence (SEQ ID NO:7). DPK-9 is the human germ-line acceptor framework sequence (SEQ ID NO:17). Vertical lines indicate differences between mouse and human residues. Sequences underlined indicate donor residues which have been retained in the graft. CDRs are indicated in bold italicized letters (not shown for DPK-9). Graft gL1 (SEQ ID NO:19) has 6 donor framework residues, gL2 (SEQ ID NO:20) has 7.

FIG. 6 shows the graft design for the 5/44 heavy chain sequence (SEQ ID NO:8); DP7 (SEQ ID NO:21) is the human germ-line acceptor framework sequence. Vertical lines indicate differences between mouse and human residues. Sequences underlined indicate donor residues which have been retained in the graft. CDRs are indicated in italicized, bold letters (not shown for DP7). Grafts gH4 (SEQ ID NO:24) and gH6 (SEQ ID NO:26) have 6 donor framework residues. Grafts gH5 (SEQ ID NO:25) and gH7 (SEQ ID NO:27) have 4 donor framework residues.

FIG. 7 shows the map of vector pMRR14.

FIG. 8 shows the map of vector pMRR10.1.

FIG. 9 shows the Biacore assay results of the chimeric 5/44 mutants.

FIG. 10 shows the oligonucleotides for 5/44 gH1 and gL1 gene assemblies (SEQ ID NOS:32-47).

FIG. 11 shows the plasmid map of intermediate vector pCR2.1(544 gH1).

FIG. 12 shows the plasmid map of intermediate vector pCR2.1(544gL1).

FIG. 13 shows the oligonucleotide cassettes used to make further grafts (SEQ ID NOS:56-65).

FIG. 14 is a graph which shows a competition assay between fluorescently labeled mouse 5/44 antibody and grafted variants.

FIG. 15 is a graph which shows a competition assay between fluorescently labeled mouse 5/44 antibody and grafted variants.

FIG. 16 shows the full DNA (SEQ ID NOS:29, 31, 66 and 67) and protein (SEQ ID NOS:28 and 30) sequences of the grafted heavy and light chains.

FIG. 17 is a schematic representation of an antibody-NAc-gamma calicheamicin DMH conjugate.

FIG. 18 is a graph which shows the effect of CMC-544 on growth of RAMOS B-cell lymphoma.

FIG. 19 is a graph which shows the effect of CMC-544 on large B-cell lymphomas in an in vivo xenograft model in nude mice.

FIG. 20 is a graph which compares the effects of CMC-544 made with the CMA-676 conjugation process and the CMC-544 conjugation process on the growth of RL lymphoma.

FIG. 21 is a graph which shows that rituximab (RITUXAN®)-treated large RL lymphoma is susceptible to CMC-544 treatment.

FIG. 22 is a graph which shows the effect of rituximab (RITUXAN®) on the cytotoxic effect of CMC-544.

FIG. 23 is a graph which shows the effect of CMC-544, rituximab (RITUXAN®), and CMA-676 on the survival of SCID mice with disseminated early RAMOS B lymphoma.

FIG. 24 is a graph which shows the effect of CMC-544, rituximab (RITUXAN®), and CMA-676 on the survival of SCID mice with disseminated late RAMOS B lymphoma.

FIG. 25 is a graph which shows the effect of CMC-544, rituximab (RITUXAN®), and CMA-676 on the survival of SCID mice with disseminated late RAMOS B lymphoma.

FIG. 26 is a graph which shows the effect of CMC-544, rituximab (RITUXAN®), and CMA-676 on the survival of SCID mice with disseminated late RAMOS B lymphoma.

FIG. 27 is a graph which shows the effect of CMC-544, rituximab (RITUXAN®), and CMA-676 on the survival of SCID mice with disseminated late RAMOS B lymphoma.

FIG. 28 is a graph which shows the anti-tumor activity of CMC-544 with and without rituximab (RITUXAN®) on RL Non-Hodgkin's lymphoma.

FIG. 29 is a graph which shows the antitumor activity of CMC-544 and CHOP on RL Non-Hodgkin's lymphoma.

DETAILED DESCRIPTION OF THE INVENTION

The conjugates of the present invention comprise a cytotoxic drug derivatized with a linker that includes any reactive group that reacts with a proteinaceous carrier to form a cytotoxic drug derivative-proteinaceous carrier conjugate. Specifically, the conjugates of the present invention comprise a cytotoxic drug derivatized with a linker that includes any reactive group which reacts with an antibody used as a proteinaceous carrier to form a cytotoxic drug derivative-antibody conjugate.

Specifically, the antibody reacts against a cell surface antigen on B-cell malignancies. Described below is an improved process for making and purifying such conjugates. The use of particular cosolvents, additives, and specific reaction conditions together with the separation process results in the formation of a monomeric cytotoxic drug derivative/antibody conjugate with a significant reduction in the LCF. The monomeric form as opposed to the aggregated form has significant therapeutic value, and minimizing the LCF and substantially reducing aggregation results in the utilization of the antibody starting material in a therapeutically meaningful manner by preventing the LCF from competing with the more highly conjugated fraction (HCF).

I. Carriers

The carriers/targeting agents of the present invention are preferably proteinaceous carriers/targeting agents. Included as carrier/targeting agents are hormones, growth factors, antibodies, antibody fragments, antibody mimics, and their genetically or enzymatically engineered counterparts, hereinafter referred to singularly or as a group as "carriers". The essential property of a carrier is its ability to recognize and bind to an antigen or receptor associated with undesired cells and to be subsequently internalized. Examples of carriers that are applicable in the present invention are disclosed in U.S. Pat. No. 5,053,394, which is incorporated herein in its entirety. Preferred carriers for use in the present invention are antibodies and antibody mimics.

A number of non-immunoglobulin protein scaffolds have been used for generating antibody mimics that bind to antigenic epitopes with the specificity of an antibody (PCT Publication No. WO 00/34784). For example, a "minibody" scaffold, which is related to the immunoglobulin fold, has been designed by deleting three beta strands from a heavy chain variable domain of a monoclonal antibody (Tramontano et al., J. Mol. Recognit. 7:9, 1994). This protein includes 61 residues and can be used to present two hypervariable loops. These two loops have been randomized and products selected for antigen binding, but thus far the framework appears to have somewhat limited utility due to solubility problems. Another framework used to display loops is tendamistat, a protein that specifically inhibits mammalian alpha-amylases and is a 74 residue, six-strand beta-sheet sandwich held together by two disulfide bonds, (McConnell and Hoess, J. Mol. Biol. 250:460, 1995). This scaffold includes three loops, but, to date, only two of these loops have been examined for randomization potential.

Other proteins have been tested as frameworks and have been used to display randomized residues on alpha helical surfaces (Nord et al., Nat. Biotechnol. 15:772, 1997; Nord et al., Protein Eng. 8:601, 1995), loops between alpha helices in alpha helix bundles (Ku and Schultz, Proc. Natl. Acad. Sci. USA 92:6552, 1995), and loops constrained by disulfide bridges, such as those of the small protease inhibitors (Markland et al., Biochemistry 35:8045, 1996; Markland et al., Biochemistry 35:8058, 1996; Rottgen and Collins, Gene 164; 243, 1995; Wang et al., J. Biol. Chem. 270:12250, 1995).

Examples of antibody carriers that may be used in the present invention include monoclonal antibodies, chimeric antibodies, humanized antibodies, human antibodies and biologically active fragments thereof. Preferably, such antibodies are directed against cell surface antigens expressed on target cells and/or tissues in proliferative disorders such as cancer. Examples of specific antibodies directed against cell surface antigens on target cells include without limitation, antibodies against CD22 antigen which is over-expressed on most B-cell lymphomas; G5/44, a humanized form of a murine anti-CD22 monoclonal antibody; antibodies against cell surface antigen CD33, which is prevalent on certain human myeloid tumors especially acute myeloid leukemia; hP67.6, a humanized form of the anti-CD33 murine antibody (see U.S. Pat. No. 5,773,001); an antibody against the PEM antigen found on many tumors of epithelial origin designated mP67.6 (see I. D. Bernstein et al., J. Clin. Invest. 79:1153 (1987) and I. D. Bernstein et al., J. Immunol. 128:867-881 (1992)); and a humanized antibody against the Lewis Y carbohydrate antigen overexpressed on many solid tumors designated hu3S193, (see U.S. Pat. No. 6,310,185 B1). In addition, there are several commercially available antibodies such as rituximab (RITUXAN®) and trastuzumab (HERCEPTIN®), which may also be used as carriers/targeting agents. Rituximab (RITUXAN®) is a chimeric anti-CD20 antibody used to treat various B-cell lymphomas and trastuzumab (HERCEPTIN®) is a humanized anti-Her2 antibody used to treat breast cancer.

Exemplified herein for use as a carrier in the present invention is a CDR-grafted humanized antibody molecule directed against cell surface antigen CD22, designated G5/44. This antibody is a humanized form of a murine anti-CD22 monoclonal antibody that is directed against the cell surface antigen CD22, which is prevalent on certain human lymphomas. The term "a CDR-grafted antibody molecule" as used herein refers to an antibody molecule wherein the heavy and/or light chain contains one or more complementarity determining regions (CDRs) including, if desired, a modified CDR (hereinafter CDR) from a donor antibody (e.g., a murine monoclonal antibody) grafted into a heavy and/or light chain variable region framework of an acceptor antibody (e.g., a human antibody). Preferably, such a CDR-grafted antibody has a variable domain comprising human acceptor framework regions as well as one or more of the donor CDRs referred to above.

When the CDRs are grafted, any appropriate acceptor variable region framework sequence may be used having regard to the class/type of the donor antibody from which the CDRs are derived, including mouse, primate and human framework regions. Examples of human frameworks, which can be used in the present invention are KOL, NEWM, REI, EU, TUR, TEI, LAY and POM (Kabat et al., Seq. of Proteins of Immunol. Interest, 1:310-334 (1994)). For example, KOL and NEWM can be used for the heavy chain, REI can be used for the light chain and EU, LAY and POM can be used for both the heavy chain and the light chain.

In a CDR-grafted antibody of the present invention, it is preferred to use as the acceptor antibody one having chains which are homologous to the chains of the donor antibody. The acceptor heavy and light chains do not necessarily need to be derived from the same antibody and may, if desired, comprise composite chains having framework regions derived from different chains.

Also, in a CDR-grafted antibody of the present invention, the framework regions need not have exactly the same sequence as those of the acceptor antibody. For instance, unusual residues may be changed to more frequently occurring residues for that acceptor chain class or type. Alternatively, selected residues in the acceptor framework regions may be changed so that they correspond to the residue found at the same position in the donor antibody or to a residue that is a conservative substitution for the residue found at the same position in the donor antibody. Such changes should be kept to the minimum necessary to recover the affinity of the donor antibody. A protocol for selecting residues in the acceptor framework regions which may need to be changed is set forth in PCT Publication No. WO 91/09967, which is incorporated herein in its entirety.

Donor residues are residues from the donor antibody, i.e., the antibody from which the CDRs were originally derived.

The antibody of the present invention may comprise a heavy chain wherein the variable domain comprises as CDR-H2 (as defined by Kabat et al., (supra)) an H2' in which a potential glycosylation site sequence has been removed in order to increase the affinity of the antibody for the antigen.

Alternatively or additionally, the antibody of the present invention may comprise a heavy chain wherein the variable domain comprises as CDR-H2 (as defined by Kabat et al., (supra)) an H2" in which a lysine residue is at position 60. This lysine residue, which is located at an exposed position within CDR-H2, and is considered to have the potential to react with conjugation agents resulting in a reduction of antigen binding affinity, is substituted with an alternative amino acid.

Additionally, the antibody of the present invention may comprise a heavy chain wherein the variable domain comprises as CDR-H2 (as defined by Kabat et al., (supra))' an H2''' in which both the potential glycosylation site sequence and the lysine residue at position 60, are substituted with alternative amino acids.

The antibody of the present invention may comprise: a complete antibody having full length heavy and light chains; a biologically active fragment thereof, such as a Fab, modified Fab, Fab', $F(ab')_2$ or Fv fragment; a light chain or heavy chain monomer or dimer; or a single chain antibody, e.g., a single chain Fv in which the heavy and light chain variable domains are joined by a peptide linker. Similarly, the heavy and light chain variable regions may be combined with other antibody domains as appropriate.

The antibody of the present invention may also include a modified Fab fragment wherein the modification is the addition of one or more amino acids to allow for the attachment of an effector or reporter molecule to the C-terminal end of its heavy chain. Preferably, the additional amino acids form a modified hinge region containing one or two cysteine residues to which the effector or reporter molecule may be attached.

The constant region domains of the antibody of the present invention, if present, may be selected having regard to the proposed function of the antibody, and in particular the effector functions which may or may not be required. For example, the constant region domains may be human IgA, IgD, IgE, IgG or IgM domains. In particular, human IgG constant region domains may be used, especially of the IgG1 and IgG3 isotypes when the antibody is intended for therapeutic uses and antibody effector functions are required. Alternatively, IgG2 and IgG4 isotypes may be used or the IgG1 Fc region may be mutated to abrogate the effector function when the antibody is intended for therapeutic purposes and antibody effector functions are not required or desired.

The antibody of the present invention has a binding affinity of at least $5\times10^{-9}$ M, preferably at least $1\times10^{-9}$ M, more preferably at least $0.75\times10^{-10}$ M, and most preferably at least $0.5\times10^{-10}$ M.

In one embodiment, the present invention relates to immunotoxin conjugates and methods for making these conjugates using antibody variants or antibody mimics. In a preferred embodiment, variants of the antibody of the present invention are directed against CD22 and display improved affinity for CD22. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 260, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998).

Any suitable host cell/vector system may be used for expression of the DNA sequences encoding the carrier including antibodies of the present invention. Bacterial, for example *E. coli*, and other microbial systems may be used, in part, for expression of antibody fragments such as Fab and F(ab')$_2$ fragments, and especially Fv fragments and single chain antibody fragments, for example, single chain Fvs. Eukaryotic, e.g. mammalian, host cell expression systems may be used for production of larger antibody, including complete antibody molecules. Suitable mammalian host cells include CHO, myeloma, yeast cells, insect cells, hybridoma cells, NSO, VERO or PER C6 cells. Suitable expression systems also include transgenic animals and plants.

II. Therapeutic Agents

The therapeutic agents suitable for use in the present invention are cytotoxic drugs that inhibit or disrupt tubulin polymerization, alkylating agents that bind to and disrupt DNA, and agents which inhibit protein synthesis or essential cellular proteins such as protein kinases, enzymes and cyclins. Examples of such cytotoxic drugs include, but are not limited to thiotepa, taxanes, vincristine, daunorubicin, doxorubicin, epirubicin, actinomycin, authramycin, azaserines, bleomycins, tamoxifen, idarubicin, dolastatins/auristatins, hemiasterlins, calicheamicins, esperamicins and maytansinoids. Preferred cytotoxic drugs are the calicheamicins, which are an example of the methyl trisulfide antitumor antibiotics. Examples of calicheamicins suitable for use in the present invention are disclosed, for example, in U.S. Pat. No. 4,671,958; U.S. Pat. No. 4,970,198, U.S. Pat. No. 5,053,394, U.S. Pat. No. 5,037,651; and U.S. Pat. No. 5,079,233, which are incorporated herein in their entirety. Preferred calicheamicins are the gamma-calicheamicin derivatives or the N-acetyl gamma-calicheamicin derivatives.

III. Cytotoxic Drug Derivative/Carrier Conjugates

The conjugates of the present invention have the formula Pr(—X—W)$_m$ wherein:

Pr is a proteinaceous carrier,

X is a linker that comprises a product of any reactive group that can react with a proteinaceous carrier, W is the cytotoxic drug;

m is the average loading for a purified conjugation product such that the calicheamicin constitutes 4-10% of the conjugate by weight; and (—X—W)$_m$ is a cytotoxic drug Preferably, X has the formula (CO-Alk$^1$-Sp$^1$—Ar—Sp$^2$-Alk$^2$-C(Z$^1$)=Q-Sp)

wherein

Alk$^1$ and Alk$^2$ are independently a bond or branched or unbranched (C$_1$-C$_{10}$) alkylene chain;

Sp$^1$ is a bond, —S—, —O—, —CONH—, —NHCO—, —NR'—, —N(CH$_2$CH$_2$)$_2$N—, or —X—Ar'-Y—(CH$_2$)$_n$—Z wherein X, Y, and Z are independently a bond, —NR'—, —S—, or —O—, with the proviso that when n=0, then at least one of Y and Z must be a bond and Ar' is 1,2-, 1,3-, or 1,4-phenylene optionally substituted with one, two, or three groups of (C$_1$-C$_5$) alkyl, (C$_1$-C$_4$) alkoxy, (C$_1$-C$_4$) thioalkoxy, halogen, nitro, —COOR', —CONHR', —(CH$_2$)$_n$COOR', —S(CH$^2$)$_n$COOR', —O(CH$_2$)$_n$CONHR', or —S(CH$_2$)$_n$CONHR', with the proviso that when Alk$_1$ is a bond, Sp$_1$ is a bond;

n is an integer from 0 to 5;

R' is a branched or unbranched (C$_1$-C$_5$) chain optionally substituted by one or two groups of —OH, (C$_1$-C$_4$) alkoxy, (C$_1$-C$_4$) thioalkoxy, halogen, nitro, (C$_1$-C$_3$) dialkylamino, or (C$_1$-C$_3$) trialkylammonium-A- where A- is a pharmaceutically acceptable anion completing a salt;

Ar is 1,2-, 1,3-, or 1,4-phenylene optionally substituted with one, two, or three groups of (C$_1$-C$_6$) alkyl, (C$_1$-C$_5$) alkoxy, (C$_1$-C$_4$) thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR' wherein n and R' are as hereinbefore defined or a 1,2-, 1,3-, 1,4-, 1,5-, 1,6-, 1,7-, 1,8-, 2,3-, 2,6-, or 2,7-naphthylidene or

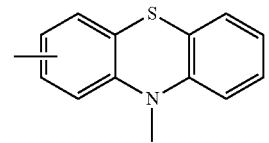

with each naphthylidene or phenothiazine optionally substituted with one, two, three, or four groups of (C$_1$-C$_6$) alkyl, (C$_1$-C$_5$) alkoxy, (C$_1$-C$_4$) thioalkoxy, halogen, nitro, —COOR', —CONHR', —O(CH$_2$)$_n$COOR', —S(CH$_2$)$_n$COOR' or —S(CH$_2$)$_n$CONHR' wherein n and R' are as defined above, with the proviso that when Ar is phenothiazine, Sp$^1$ is a bond only connected to nitrogen; Sp$^2$ is a bond, —S—, or —O—, with the proviso that when Alk$^2$ is a bond, Sp$^2$ is a bond;

Z$^1$ is H, (C$_1$-C$_5$) alkyl, or phenyl optionally substituted with one, two, or three groups of (C$_1$-C$_5$) alkyl, (C$_1$-C$_5$) alkoxy, (C$_1$-C$_4$) thioalkoxy, halogen, nitro, —COOR', —ONHR', —O(CH$_2$)$_n$COOR', —S(CH$_2$)$_n$COOR', —O(CH$_2$)$_n$CONHR', or —S(CH$_2$)$_n$CONHR' wherein n and R' are as defined above;

Sp is a straight or branched-chain divalent or trivalent (C$_1$-C$_{18}$) radical, divalent or trivalent aryl or heteroaryl radical, divalent or trivalent (C$_3$-C$_{18}$) cycloalkyl or heterocycloalkyl radical, divalent or trivalent aryl- or heteroaryl-aryl (C$_1$-C$_{18}$) radical, divalent or trivalent cycloalkyl- or heterocycloalkyl-alkyl (C$_1$-C$_{18}$) radical or divalent or trivalent (C$_2$-C$_{18}$) unsaturated alkyl radical, wherein heteroaryl is preferably furyl, thienyl, N-methylpyrrolyl, pyridinyl, N-methylimidazolyl, oxazolyl, pyrimidinyl, quinolyl, isoquinolyl, N-methylcarbazoyl, aminocourmarinyl, or phenazinyl and wherein if Sp is a trivalent radical, Sp can be additionally substituted by lower (C$_1$-C$_5$) dialkylamino, lower (C$_1$-C$_5$) alkoxy, hydroxy, or lower (C$_1$-C$_5$) alkylthio groups; and Q is =NHNCO—, =NHNCS—, =NHNCONH—, =NHNCSNH—, or =NHO—.

Preferably, Alk$^1$ is a branched or unbranched (C$_1$-C$_{10}$) alkylene chain; Sp' is a bond, —S—, —O—, —CONH—, —NHCO—, or —NR' wherein R' is as hereinbefore defined, with the proviso that when Alk$^1$ is a bond, Sp$^1$ is a bond;

Ar is 1,2-, 1,3-, or 1,4-phenylene optionally substituted with one, two, or three groups of (C$_1$-C$_6$) alkyl, (C$_1$-C$_5$) alkoxy, (C$_1$-C$_4$) thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR' wherein n and R' are as hereinbefore defined, or Ar is a 1,2-, 1,3-, 1,4-, 1,5-, 1,6-, 1,7-, 1,8-, 2,3-, 2,6-, or 2,7-naphthylidene each optionally substituted with one, two, three, or four groups of $(C_1-C_6)$ alkyl, $(C_1-C_5)$ alkoxy, $(C_1-C_4)$ thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR'.

$Z^1$ is $(C_1-C_5)$ alkyl, or phenyl optionally substituted with one, two, or three groups of $(C_1-C_5)$ alkyl, $(C_1-C_4)$ alkoxy, $(C_1-C_4)$ thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR'; Alk$^2$ and Sp$^2$ are together a bond; and Sp and Q are as immediately defined above.

U.S. Pat. No. 5,773,001, incorporated herein in its entirety, discloses linkers that can be used with nucleophilic derivatives, particularly hydrazides and related nucleophiles, prepared from the calicheamicins. These linkers are especially useful in those cases where better activity is obtained when the linkage formed between the drug and the linker is hydrolyzable. These linkers contain two functional groups. One group typically is a carboxylic acid that is utilized to react with the carrier. The acid functional group, when properly activated, can form an amide linkage with a free amine group of the carrier, such as, for example, the amine in the side chain of a lysine of an antibody or other proteinaceous carrier. The other functional group commonly is a carbonyl group, i.e., an aldehyde or a ketone, which will react with the appropriately modified therapeutic agent. The carbonyl groups can react with a hydrazide group on the drug to form a hydrazone linkage. This linkage is hydrolyzable, allowing for release of the therapeutic agent from the conjugate after binding to the target cells.

A most preferred bifunctional linker for use in the present invention is 4-(4-acetylphenoxy) butanoic acid (AcBut), which results in a preferred product wherein the conjugate consists of β-calicheamicin, γ-calicheamicin or N-acetyl γ-calicheamicin functionalized by reacting with 3-mercapto-3-methyl butanoyl hydrazide, the AcBut linker, and a human or humanized IgG antibody targeting carrier.

IV. Monomeric Conjugation

The natural hydrophobic nature of many cytotoxic drugs including the calicheamicins creates difficulties in the preparation of monomeric drug conjugates with good drug loadings and reasonable yields which are necessary for therapeutic applications. The increased hydrophobicity of the linkage provided by linkers, such as the AcBut linker, disclosed in U.S. Pat. No. 5,773,001, as well as the increased covalent distance separating the therapeutic agent from the carrier (antibody), exacerbate this problem.

Aggregation of cytotoxic drug derivative/carrier conjugates with higher drug loadings occurs due to the hydrophobic nature of the drugs. The drug loading often has to be limited to obtain reasonable quantities of monomeric product. In some cases, such as with the conjugates in U.S. Pat. No. 5,877,296, it is often difficult to make conjugates in useful yields with useful loadings for therapeutic applications using the reaction conditions disclosed in U.S. Pat. No. 5,053,394 due to excessive aggregation. These reaction conditions utilized DMF as the co-solvent in the conjugation reaction. Methods which allow for higher drug loadings/yield without aggregation and the inherent loss of material are therefore needed.

Improvements to reduce aggregation are described in U.S. Pat. Nos. 5,712,374 and 5,714,586, which are incorporated herein in their entirety. Disclosed in those patents are proteinaceous carriers including, but not limited to, proteins such as human or humanized antibodies that are used to target the cytotoxic therapeutic agents, such as, for example, hP67.6 the other humanized antibodies disclosed therein. In those patents, the use of a non-nucleophilic, protein-compatible, buffered solution containing (i) propylene glycol as a cosolvent and (ii) an additive comprising at least one $C_6$-$C_{18}$ carboxylic acid was found to generally produce monomeric cytotoxic drug derivative/carrier conjugates with higher drug loading/yield and decreased aggregation having excellent activity. Preferred acids described therein were $C_7$ to $C_{12}$ acids, and the most preferred acid was octanoic acid (such as caprylic acid) or its salts. Preferred buffered solutions for conjugates made from N-hydroxysuccinimide (OSu) esters or other comparably activated esters were phosphate-buffered saline (PBS) or N-2-hydroxyethyl piperazine-N'-2-ethanesulfonic acid (HEPES buffer). The buffered solution used in those conjugation reactions cannot contain free amines or nucleophiles. For other types of conjugates, acceptable buffers can be readily determined. Alternatively, the use of a non-nucleophilic, protein-compatible, buffered solution containing t-butanol without the additional additive was also found to produce monomeric calicheamicin derivative/carrier conjugates with higher drug loading/yield and decreased aggregation.

The amount of cosolvent needed to form a monomeric conjugate varies somewhat from protein to protein and can be determined by those of ordinary skill in the art without undue experimentation. The amount of additive necessary to effectively form a monomeric conjugate also varies from antibody to antibody. This amount can also be determined by one of ordinary skill in the art without undue experimentation. In U.S. Pat. Nos. 5,712,374 and 5,714,586, additions of propylene glycol in amounts ranging from 10% to 60%, preferably 10% to 40%, and most preferably about 30% by volume of the total solution, and an additive comprising at least one $C_6$-$C_{18}$ carboxylic acid or its salt, preferably caprylic acid or its salt, in amounts ranging from 20 mM to 100 mM, preferably from 40 mM to 90 mM, and most preferably about 60 mM to 90 mM were added to conjugation reactions to produce monomeric cytotoxic drug derivative/carrier conjugates with higher drug loading/yield and decreased aggregation. Other protein-compatible organic cosolvents other than propylene glycol, such as ethylene glycol, ethanol, DMF, DMSO, etc., could also be used. Some or all of the organic cosolvent was used to transfer the drug into the conjugation mixture.

Alternatively, in those patents, the concentration of the $C_6$-$C_{18}$ carboxylic acid or its salt could be increased to 150-300 mM and the cosolvent dropped to 1-10%. In one embodiment, the carboxylic acid was octanoic acid or its salt. In a preferred embodiment, the carboxylic acid was decanoic acid or its salt. In another preferred embodiment, the carboxylic acid was caprylic acid or its salt, which was present at a concentration of 200 mM caprylic acid together with 5% propylene glycol or ethanol.

In another alternative embodiment in those patents, t-butanol at concentrations ranging from 10% to 25%, preferably 15%, by volume of the total solution could be added to the conjugation reaction to produce monomeric cytotoxic drug derivative/carrier conjugates with higher drug loading/yield and decreased aggregation.

These established conjugation conditions were applied to the formation of CMA-676 (Gemtuzumab Ozogamicin), which is now commercially sold as MYLOTARG®. Since introduction of this treatment for acute myeloid leukemia (AML), it has been learned through the use of ion-exchange chromatography that the calicheamicin is not distributed on the antibody in a uniform manner. Most of the calicheamicin is on approximately half of the antibody, while the other half exists in a LCF that contains only small amounts of calicheamicin. Consequently, there is a critical need to improve the methods for conjugating cytotoxic drugs such as calicheamicins to carriers which minimize the amount of aggregation and allow for a higher uniform drug loading with a significantly improved yield of the conjugate product.

A specific example is that of the G5/44-NAc-gamma-calicheamicin DMH AcBut conjugate, which is referred to as CMC-544 and is generically shown in FIG. 17. The reduction of the amount of the LCF to <10% of the total antibody was desired for development of CMC-544, and various options for reduction of the levels of the LCF were considered. Other attributes of the immunoconjugate, such as antigen binding and cytotoxicity, must not be affected by the ultimate solution. The options considered included genetic or physical modification of the antibody, the chromatographic separation techniques, or the modification of the reaction conditions.

Reaction of the G5/44 antibody with NAc-gamma-calicheamicin DMH AcBut OSu using the old reaction conditions (CMA-676 Process Conditions) resulted in a product with similar physical properties (drug loading, LCF, and aggregation) as CMA-676. However, the high level (50-60%) of LCF present after conjugation was deemed undesirable. Optimal reaction conditions were determined through statistical experimental design methodology in which key reaction variables such as temperature, pH, calicheamicin derivative input, and additive concentration, were evaluated. Analysis of these experiments demonstrated that calicheamicin input and additive concentration had the most significant effects on the level of the low conjugated fraction LCF and aggregate formation, while temperature and pH exerted smaller influences. In additional experiments, it was also shown that the concentrations of protein carrier (antibody) and cosolvent (ethanol) were similarly of lesser importance (compared to calicheamicin input and additive concentration) in controlling LCF and aggregate levels. In order to reduce the LCF to <10%, the calicheamicin derivative input was increased from 3% to 8.5% (w/w) relative to the amount of antibody in the reaction. The additive was changed from octanoic acid or its salt at a concentration of 200 mM (CMA-676 process) to decanoic acid or its salt at a concentration of 37.5 mM. The conjugation reaction proceeded better at slightly elevated temperature (30-35° C.) and pH (8.2-8.7). The reaction conditions incorporating these changes reduced the LCF to below 10 percent while increasing calicheamicin loading, and is hereinafter referred to as CMC-544 Process Condition or "new" process conditions. A comparison of the results obtained with the CMA-676 and CMC-544 Process Conditions is shown in Table 1.

TABLE 1

COMPARISON OF THE CMA-676 AND CMC-544 PROCESS CONDITIONS

| CONDITIONS/ RESULTS | CMA-676 PROCESS CONDITIONS | CMC-544 PROCESS CONDITIONS |
| --- | --- | --- |
| Calicheamicin Input | 3.0% (w/w powder weight basis) | 8.5% (w/w) |
| Additive Identity and Concentration | Octanoic acid/Sodium octanate; 200 mM | Decanoic acid/Sodium decanoate; 37.5 mM |
| Temperature | 26° C. | 31-35° C. |
| pH | 7.8 | 8.2.-8.7 |
| Calicheamic Loading (percent by weight; by UV assay) | 2.4-3.5 | 7.0-9.0 |
| Low Conjugated Fraction (LCF) (before purification) | 45-65 HPLC Area % | <10% |
| Aggregation (before purification) | ~5% | <5% |
| Aggregation (after purification) | <2% | <2% |

The increase in calicheamicin input increased the drug loading from 2.5-3.0 weight percent to 7.0-9.0 (most typically 7.5-8.5) weight percent, and resulted in no increase in protein aggregation in the reaction. Due to reduction of aggregate and LCF, the CMC-544 Process Conditions resulted in a more homogeneous product. CMC-544 has been reproducibly prepared by this new conjugation procedure at the multigram antibody scale.

In the foregoing reactions, the concentration of antibody can range from 1 to 15 mg/ml and the concentration of the calicheamicin derivative, e.g., N-Acetyl gamma-calicheamicin DMH AcBut OSu ester (used to make the conjugates shown in FIG. 17), ranges from about 4.5-11% by weight of the antibody. The cosolvent was ethanol, for which good results have been demonstrated at concentrations ranging from 6 to 11.4% (volume basis). The reactions were performed in PBS, HEPES, N-(2-Hydroxyethyl)piperazine-N'-(4-butanesulfonic acid) (HEPBS), or other compatible buffer at a pH of 8 to 9, at a temperature ranging from 30° C. to about 35° C., and for times ranging from 15 minutes to 24 hours. Those who are skilled in the art can readily determine acceptable pH ranges for other types of conjugates. For various antibodies the use of slight variations in the combinations of the aforementioned additives have been found to improve drug loading and monomeric conjugate yield, and it is understood that any particular protein carrier may require some minor alterations in the exact conditions or choice of additives to achieve the optimum results.

V. Conjugate Purification and Separation

Following conjugation, the monomeric conjugates may be separated from the unconjugated reactants (such as proteinaceous carrier and free cytotoxic drug/calicheamicin) and/or the aggregated form of the conjugates by conventional methods, for example, size exclusion chromatography (SEC), hydrophobic interaction chromatography (HIC), ion exchange chromatography (IEC), or chromatofocusing (CF). The purified conjugates are monomeric, and usually contain from 4 to 10% by weight cytotoxic drug/calicheamicin. In a preferred embodiment, the conjugates are purified using hydrophobic interaction chromatography (HIC). In the processes previously used for the production-scale manufacturing of cytotoxic drug/calicheamicin-antibody conjugates (CMA-676 process), the sole post-conjugation separation step employed was size exclusion chromatography (SEC). While this step is quite effective at both removing aggregated conjugate and in accomplishing buffer exchange for formulation, it is ineffective at reducing the LCF content. Consequently, the SEC-based process relies entirely on the chemistry of the conjugation reaction to control the LCF content of the final product. Another disadvantage of SEC is the limitation of the volume of conjugate reaction mixture applied to the column (typically not exceeding 5 percent of the process column bed volume). This severely limits the batch size (and therefore production capacity) that can be supported in a given production space. Finally, the SEC purification process also results in significant dilution of the conjugate solution, which places constraints on the protein concentration that can be dependably achieved in formulation.

When a cytotoxic drug has a highly hydrophobic nature, such as a calicheamicin derivative, and is used in a conjugate, hydrophobic interaction chromatography (HIC) is a preferred candidate to provide effective separation of conjugated and unconjugated antibody. HIC presents three key advantages over SEC: (1) it has the capability to efficiently reduce the LCF content as well as the aggregate; (2) the column load capacity for HIC is much higher; and (3) HIC avoids excessive dilution of the product.

A number of high-capacity HIC media suitable for production scale use, such as Butyl, Phenyl and Octyl SEPHAROSE™ 4 Fast Flow (Amersham Biosciences, Piscataway, N.J.), can effectively separate unconjugated components and aggregates of the conjugate from monomeric conjugated components following the conjugation process.

VI. Compositions and Formulations

The present invention also provides a process for the preparation of a therapeutic or diagnostic composition/formulation comprising admixing the monomeric cytotoxic drug derivative/carrier conjugate of the present invention together with a pharmaceutically acceptable excipient, diluent or carrier.

The monomeric cytotoxic drug derivative/carrier conjugate may be the sole active ingredient in the therapeutic or diagnostic composition/formulation or may be accompanied by other active ingredients including other antibody ingredients, for example anti-CD19, anti-CD20, anti-CD33, anti-T cell, anti-IFNγ or anti-LPS antibodies, or non-antibody ingredients such as cytokines, growth factors, hormones, antihormones, cytotoxic drugs and xanthines.

Cytokines and growth factors that may be used to treat proliferative disorders such as cancer, and which may be used together with the cytotoxic drug derivative/carrier conjugates of the present invention include interferons, interleukins such as interleukin 2 (IL-2), TNF, CSF, GM-CSF and G-CSF.

Hormones commonly used to treat proliferative disorders such as cancer and which may be used together with the cytotoxic drug derivative/carrier conjugates of the present invention include estrogens such as diethylstilbestrol and estradiol, androgens such as testosterone and HALOTESTIN®, progestins such as MEGACE® and PROVERA®, and corticosteroids such as prednisone, dexamethasone, and hydrocortisone.

Antihormones such as antiestrogens, i.e., tamoxifen, antiandrogens i.e., flutamide and antiadrenal agents are commonly used to treat proliferative disorders such as cancer, and may be used together with the cytotoxic drug derivative/carrier conjugate of the present invention.

Chemotherapeutic/antineoplastic agents commonly used to treat proliferative disorders such as cancer, and which may be used together with the cytotoxic drug derivative/carrier conjugate of the present invention include, but are not limited to, ADRIAMYCIN®, cisplatin, carboplatin, vinblastine, vincristine, bleomycin, methotrexate, doxorubicin, fluorouracils, etoposide, taxol and its various analogs, and mitomycin.

The compositions should preferably comprise a therapeutically effective amount of a conjugate of the invention. The term "therapeutically effective amount" as used herein refers to an amount of a therapeutic agent needed to treat, ameliorate or prevent a targeted disease or condition, or to exhibit a detectable therapeutic or preventative effect. For any conjugate, the therapeutically effective dose can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgment of the clinician. Generally, an effective dose will be from 0.1 mg/m$^2$ to 50 mg/m$^2$, preferably 0.4 mg/m$^2$ to 30 mg/m$^2$, more preferably 2 m g/m$^2$ to 9 mg/m$^2$, which dose is calculated on the basis of the proteinaceous carrier.

Compositions may be administered individually to a patient or may be administered in combination with other agents, drugs or hormones. The dose at which the monomeric cytotoxic drug derivative/antibody conjugate of the present invention is administered depends on the nature of the condition to be treated, the grade of the malignant lymphoma or leukemia and on whether the conjugate is being used prophylactically or to treat an existing condition.

The frequency of dose will depend on the half-life of the conjugate and the duration of its effect. If the conjugate has a short half-life (e.g., 2 to 10 hours) it may be necessary to give one or more doses per day. Alternatively, if the conjugate molecule has a long half-life (e.g., 2 to 15 days) it may only be necessary to give a dosage once per day, once per week or even once every 1 or 2 months.

A composition may also contain a pharmaceutically acceptable carrier for administration of the antibody conjugate. The carrier should not itself induce the production of antibodies harmful to the individual receiving the composition and should not be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulfates, or salts of organic acids, such as acetates, propionates, malonates and benzoates.

Pharmaceutically acceptable carriers in these compositions may additionally contain liquids such as water, saline, glycerol, and ethanol. Additionally, auxiliary substances, such as wetting or emulsifying agents or pH buffering substances, may be present in such compositions. Such carriers enable the compositions to be formulated as tablets, pills, dragees, capsules, liquids, gels, syrups, slurries or suspensions, for ingestion by the patient.

Preferred forms for administration include forms suitable for parenteral administration, e.g., by injection or infusion, for example by bolus injection or continuous infusion. Where the product is for injection or infusion, it may take the form of a suspension, solution or emulsion in an oily or aqueous vehicle and it may contain formulatory agents, such as suspending, preserving, stabilizing and/or dispersing agents.

Although the stability of the buffered conjugate solutions is adequate for short-term stability, long-term stability is poor. To enhance stability of the conjugate and to increase its shelf life, the antibody-drug conjugate may be lyophilized to a dry form, for reconstitution before use with an appropriate sterile liquid. The problems associated with lyophilization of a protein solution are well documented. Loss of secondary, tertiary and quaternary structure can occur during freezing and drying processes. Consequently, cryoprotectants may have to be included to act as an amorphous stabilizer of the conjugate and to maintain the structural integrity of the protein during the lyophilization process. In one embodiment, the cryoprotectant useful in the present invention is a sugar alcohol, such as alditol, mannitol, sorbitol, inositol, polyethylene glycol, and combinations thereof. In another embodiment, the cryoprotectant is a sugar acid, including an aldonic acid, an uronic acid, an aldaric acid, and combinations thereof.

The cryoprotectant of this invention may also be a carbohydrate. Suitable carbohydrates are aldehyde or ketone compounds containing two or more hydroxyl groups. The carbohydrates may be cyclic or linear and include, for example, aldoses, ketoses, amino sugars, alditols, inositols, aldonic acids, uronic acids, or aldaric acids, or combinations thereof. The carbohydrate may also be a mono-, a di-, or a polycarbohydrate, such as for example, a disaccharide or polysaccharide. Suitable carbohydrates include for example, glyceraldehydes, arabinose, lyxose, pentose, ribose, xylose, galactose, glucose, hexose, idose, mannose, talose, heptose, glucose, fructose, gluconic acid, sorbitol, lactose, mannitol, methyl α-glucopyranoside, maltose, isoascorbic acid, ascorbic acid, lactone, sorbose, glucaric acid, erythrose, threose, arabinose, allose, altrose, gulose, idose, talose, erythrulose, ribulose, xylulose, psicose, tagatose, glucuronic acid, gluconic acid, glucaric acid, galacturonic acid, mannuronic acid, glucosamine, galactosamine, sucrose, trehalose or neuraminic acid, or derivatives thereof. Suitable polycarbohydrates include, for example, arabinans, fructans, fucans, galactans, galacturonans, glucans, mannans, xylans (such as, for example, inulin), levan, fucoidan, carrageenan, galactocarolose, pectins, pectic acids, amylose, pullulan, glycogen, amylopectin, cellulose, dextran, pustulan, chitin, agarose, keratin, chondroitin, dermatan, hyaluronic acid, alginic acid, xanthin gum, or starch. Among particularly useful carbohydrates are sucrose, glucose, lactose, trehalose, and combinations thereof. Sucrose is a particularly useful cryoprotectant.

Preferably, the cryoprotectant of the present invention is a carbohydrate or "sugar" alcohol, which may be a polyhydric alcohol. Polyhydric compounds are compounds that contain more than one hydroxyl group. Preferably, the polyhydric compounds are linear. Suitable polyhydric compounds include, for example, glycols such as ethylene glycol, polyethylene glycol, and polypropylene glycol, glycerol, or pentaerythritol; or combinations thereof.

In some preferred embodiments, the cryoprotectant agent is sucrose, trehalose, mannitol, or sorbitol.

Once formulated, the compositions of the invention can be administered directly to the subject. The subjects to be treated can be animals. However, it is preferred that the compositions are adapted for administration to human subjects.

The compositions of the present invention may be administered by any number of routes including, but not limited to, oral, intravenous, intramuscular, infra-arterial, intramedullary, intrathecal, intraventricular, transdermal, transcutaneous (see PCT Publication No. WO 98/20734), subcutaneous, intraperitoneal, intranasal, enteral, topical, sublingual, intravaginal or rectal routes. Hyposprays may also be used to administer the compositions of the invention. Typically, the compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be a cytotoxic drug/proteinaceous carrier conjugate. As such, it will be susceptible to degradation in the gastrointestinal tract. Thus, if the composition is to be administered by a route using the gastrointestinal tract, the composition will need to contain agents which protect the conjugate from degradation, but which release the conjugate once it has been absorbed from the gastrointestinal tract.

A thorough discussion of pharmaceutically acceptable carriers is available in Remington's Pharmaceutical Sciences (Mack Publishing Company, N.J. 1991).

The present invention in particular provides a monomeric calicheamicin derivative/humanized anti-CD22 antibody (G5/44), CMC-544, for use in treating proliferative disorders characterized by cells expressing CD22 antigen on their surface.

The present invention further provides the use of CMC-544 in the manufacture of a composition or a medicament for the treatment of a proliferative disorder characterized by cells expressing CD22.

CMC-544 may also be utilized in any therapy where it is desired to reduce the level of cells expressing CD22 that are present in the subject being treated with the composition or a medicament disclosed herein. Specifically, the composition or medicament is used to treat humans or animals with proliferative disorders namely lymphomas and leukemias, which express CD22 antigen on the cell surface. These CD22-expressing cells may be circulating in the body or be present in an undesirably large number localized at a particular site in the body.

CMC-544 may also be preferably used for treatment of malignancies of B-lymphocyte lineage including lymphomas and leukemias, most preferably Non-Hodgkin's Lymphoma (NHL), acute lymphocytic leukemia (ALL), multiple myeloma, acute lymphocyte leukemia (ALL) and chronic lymphocytic leukemia (CLL). CMC-544 can be used alone or in combination with other bioactive agents to treat subjects suffering from B-cell malignancies.

Bioactive agents commonly used include growth factors, cytokines, and cytotoxic drugs. Cytotoxic drugs commonly used to treat proliferative disorders such as cancer, and which may be used together with CMC-544 include an anthracycline such as doxorubicin, daunorubicin, idarubicin, aclarubicin, zorubicin, mitoxantrone, epirubicin, carubicin, nogalamycin, menogaril, pitarubicin, and valrubicin for up to three days; and a pyrimidine or purine nucleoside such as cytarabine, gemcitabine, trifluridine, ancitabine, enocitabine, azacitidine, doxifluridine, pentostatin, broxuridine, capecitabine, cladribine, decitabine, floxuridine, fludarabine, gougerotin, puromycin, tegafur, and tiazofurin. Other chemotherapeutic/antineoplastic agents that may be administered in combination with CMC-544 include ADRIAMYCIN®, cisplatin, carboplatin, cyclophosphamide, dacarbazine, vinblastine, vincristine, mitoxantrone, bleomycin, mechlorethamine, prednisone, procarbazine, methotrexate, fluorouracils, etoposide, taxol and its various analogs, and mitomycin. CMC-544 may be administered concurrently with one or more of these therapeutic agents. Alternatively, CMC-544 may be administered sequentially with one or more of these therapeutic agents.

CMC-544 may also be administered alone, concurrently, or sequentially with a combination of other bioactive agents such as growth factors, cytokines, steroids, antibodies such as anti-CD20 antibody, rituximab (RITUXAN®), and chemotherapeutic agents as a part of a treatment regimen. Established treatment regimens for the treatment of malignant lymphoproliferative disorders include CHOPP (cyclophosphamide, doxorubicin, vincristine, prednisone, and procarbazine), CHOP (cyclophosphamide, doxorubicin, vincristine, and prednisone), COP (cyclophosphamide, vincristine, and prednisone), CAP-BOP (cyclophosphamide, doxorubicin, procarbazine, bleomycin, vincristine, and prednisone), m-BACOD (methotrexate, bleomycin, doxorubicin, cyclophosphamide, vincristine, dexamethasone, and leucovorin), ProMACE-MOPP (prednisone, methotrexate, doxorubicin, cyclophosphamide, etoposide, leucovorin, mechloethamine, vincristine, prednisone, and procarbazine), ProMACE-CytaBOM (prednisone, methotrexate, doxorubicin, cyclophosphamide, etoposide, leucovorin, cytarabine, bleomycin, and vincristine), MACOP-B (methotrexate, doxorubicin, cyclophosphamide, vincristine, fixed dose prednisone, bleomycin, and leucovorin), MOPP (mechloethamine, vincristine, prednisone, amd procarbazine), ABVD (ADRIAMYCIN®/doxorubicin, bleomycin, vinblastine, and dacarbazine), MOPP alternating with ABV (ADRIAMYCIN®/doxorubicin, bleomycin, and vinblastine), and MOPP (mechloethamine, vincristine, prednisone, and procarbazine) alternating with ABVD (ADRIAMYCIN®/doxorubicin, bleomycin, vinblastine, and dacarbazine), and Ch1VPP (chlorambucil, vinblastine, procarbazine, and prednisone). Therapy may comprise an induction therapy phase, a consolidation therapy phase and a maintenance therapy phase. CMC-544 may also be administered alone, concurrently, or sequentially with any of the above identified therapy regimens as a part of induction therapy phase, a consolidation therapy phase and a maintenance therapy phase.

The conjugates of the present invention may also be administered together with other bioactive and chemotherapeutic agents as a part of combination chemotherapy regimen for the treatment of relapsed aggressive lymphomas. Such a treatment regimen includes IMVP-16 (ifosfamide, methotrexate, and etoposide), MIME (methyl-gag, ifosfamide, methotrexate, and etoposide), DHAP (dexamethasone, high-dose cytaribine, and cisplatin), ESHAP (etoposide, methylpredisolone, high-dose cytarabine, and cisplatin), EPOCH (etoposide, vincristine, and doxorubicin for 96 hours with bolus doses of cyclophosphamide and oral prednisone), CEPP(B) (cyclophosphamide, etoposide, procarbazine, prednisone, and bleomycin), CAMP (lomustine, mitoxantrone, cytarabine, and prednisone), CVP-1 (cyclophosphamide, vincristine and prednisone), CHOP-B (cyclophosphamide, doxorubicin, vincristine, prednisone, and Bleomycin), CEPP-B (cyclophosphamide, etoposide, procarbazine, and bleomycin), and P/DOCE (epirubicin or doxorubicin, vincristine, cyclophosphamide, and prednisone) Additional treatment regimens for aggressive lymphomas may include in phase 1 a first line of treatment with CHOP (cyclophosphamide, doxorubicin, vincristine, and prednisone)-rituximab (RITUXAN®)-CMC-544, followed in phase 2 and phase 3 with CHOP-rituximab (RITUXAN®) CHOP-CMC-544 or CHOP-rituximab (RITUXAN®)-CMC-544. Alternatively, phase 1 may have a first line of treatment with COP (cyclophosphamide, vincristine, and prednisone)-rituximab (RITUXAN®)-CMC-544, followed in phase 2 and phase 3 with COP-rituximab (RITUXAN®), COP-CMC-544 or COP-rituximab (RITUXAN®)-CMC-544. In a further embodiment, treatment of aggressive lymphomas may include a first or second line of treatment with the antibody drug conjugate CMC-544 in phase 1, followed in phase 2 and 3 with CMC-544 and CHOP (cyclophosphamide, doxorubicin, vincristine, and prednisone), CMC-544 and COP (cyclophosphamide, vincristine, and prednisone), CMC-544 with rituximab (RITUXAN®) or rituximab (RITUXAN®) alone. In yet another embodiment, the treatment of aggressive lymphomas may include a first or line of treatment with the antibody drug conjugate CMC-544 followed in phase 2 and 3 with CMC-544 alone or in combination with other treatment regimens including, but not limited to, ESHOP (etoposide, methylpredisolone, high-dose cytarabine, vincristine and cisplatin), EPOCH (etoposide, vincristine, and doxorubicin for 96 hours with bolus doses of cyclophosphamide and oral prednisone), IMVP-16 (ifosfamide, methotrexate, and etoposide), ASHAP (ADRIAMYCIN®, solumedrol, Ara-C, and cisplatin), MIME (methyl-gag, ifosfamide, methotrexate, and etoposide) and ICE (ifosfamide, cyclophosphamide, and etoposide). Details of various cytotoxic drugs used in chemotherapy of malignancies including combination chemotherapeutic regimens, dosages etc. that are provided in this application can be found in Cancer Principles and Practice of Oncology, Eds. Vincent T. DeVita, Samuelo Hellman, Steven A. Rosenberg, 6th Edition, Publishers: Lippincott, Williams and Wilkins (2001) and Physician's Cancer Chemotherapy Drug Manual, Eds. Edward Chu and Vincent T. DeVita, Publishers: Jones and Bartlett, (2002).

The present invention also provides a method of treating human or animal subjects suffering from or at risk of a proliferative disorder characterized by cells expressing CD22, the method comprising administering to the subject an effective amount of CMC-544 of the present invention.

The present invention is further described below in specific working examples, which are intended to further describe the invention without limiting its scope.

EXAMPLE 1

Generation of Candidate Antibodies

A panel of antibodies against CD22 were selected from hybridomas using the following selection criteria: binding to Daudi cells, internalization on Daudi cells, binding to peripheral blood mononuclear cells (PBMC), internalization on PBMC, affinity (greater than $10^{-9}$ M), mouse γ1 and production rate. 5/44 was selected as the preferred antibody.

I. Gene Cloning and Expression of a Chimeric 5/44 Antibody Molecule a) Preparation of 5/44 Hybridoma Cells and RNA Preparation Therefrom Hybridoma 5/44 was generated by conventional hybridoma technology following immunization of mice with human CD22 protein. RNA was prepared from 5/44 hybridoma cells using a RNEasy kit (Qiagen, Crawley, UK; Catalogue No. 74106). The RNA obtained was reverse transcribed to cDNA, as described below.

b) Distribution of CD22 on NHL Tumors

An immunohistochemistry study was undertaken to examine the incidence and distribution of staining using the 5/44 anti-CD22 monoclonal antibodies. Control anti-CD20 and anti-CD79a antibodies were included in the study to confirm B cell areas of tumors. A total of 50 tumors were studied and these were categorized as follows by using the Working Formulation and REAL classification systems:

7 B lymphoblastic leukemia/lymphoma (High/I)
4 B-CLL/small lymphocytic lymphoma (Low/A)
3 lymphoplasmacytoid/Immunocytoma (Low/A)
1 Mantle cell (Int/F)
14 Follicle center lymphoma (Low to Int/D)
13 Diffuse large cell lymphoma (Int to High/G,H)
6 Unclassifiable (K)
2 T cell lymphomas Forty B cell lymphomas were positive for CD22 antigen with the 5/44 antibody at 0.1 µg/ml and a further six became positive when the concentration was increased to 0.5 µg/ml. For the remaining two B cell tumors that were negative at 0.1 µg/ml, there was insufficient tissue remaining to test at the higher concentration. However, parallel testing with another anti-CD22 antibody designated 6/13 (Celltech, Slough, UK), which gave stronger staining than 5/44, resulted in all 48 B cell lymphomas staining positive for CD22.

Thus, it is possible to conclude that the CD22 antigen is widely expressed on B cell lymphomas and therefore provides a suitable target for immunotherapy in NHL.

c) PCR Cloning of 5/44 $V_H$ and $V_L$ cDNA sequences coding for the variable domains of 5/44 heavy and light chains were synthesized using reverse transcriptase to produce single stranded cDNA copies of the mRNA present in the total RNA. This was then used as the template for amplification of the murine V-region sequences using specific oligonucleotide primers by the Polymerase Chain Reaction (PCR).

i) cDNA Synthesis cDNA was synthesized in a 20 µl reaction volume containing the following reagents: 50 mM Tris-HCl pH 8.3, 75 mM KCl, 10 mM dithiothreitol, 3 mM $MgCl_2$, 0.5 mM of dATP, dTTP, dCTP, and dGTP, 20 units RNAsin, 75 ng random hexanucleotide primer, 2 µg 5/44 RNA and 200 units Moloney Murine Leukemia Virus reverse transcriptase. After incubation at 42° C. for 60 minutes, the reaction was terminated by heating at 95° C. for 5 minutes.

ii) PCR

Aliquots of the cDNA were subjected to PCR using combinations of primers specific for the heavy and light chains. Degenerate primer pools designed to anneal with the conserved sequences of the signal peptide were used as forward primers. These sequences all contain, in order, a restriction site ($V_L$ SfuI; $V_H$ HindIII) starting 7 nucleotides from their 5' ends, the sequence GCCGCCACC (SEQ ID NO:50), to allow optimal translation of the resulting mRNAs, an initiation codon and 20-30 nucleotides based on the leader peptide sequences of known mouse antibodies (Kabat et al., Sequences of Proteins of Immunological Interest, 5th Edition, 1991, U.S. Department of Health and Human Services, Public Health Service, National Institutes of Health).

The 3' primers are designed to span the framework 4 J-C junction of the antibody and contain a restriction site for the enzyme BsiWI to facilitate cloning of the $V_L$ PCR fragment. The heavy chain 3' primers are a mixture designed to span the J-C junction of the antibody. The 3' primer includes an ApaI restriction site to facilitate cloning. The 3' region of the primers contains a mixed sequence based on those found in known mouse antibodies (Kabat et al., 1991, supra).

The combinations of primers described above enable the PCR products for $V_H$ and $V_L$ to be cloned directly into an appropriate expression vector (see below) to produce chimeric (mouse-human) heavy and light chains and for these genes to be expressed in mammalian cells to produce chimeric antibodies of the desired isotype.

Incubations (100 µl) for the PCR were set up as follows. Each reaction contained 10 mM Tris-HCl pH 8.3, 1.5 mM $MgCl_2$, 50 mM KCl, 0.01% w/v gelatin, 0.25 mM of dATP, dTTP, dCTP, and dGTP, 10 pmoles 5' primer mix, 10 pmoles 3' primer, 1 µl cDNA and 1 unit Taq polymerase. Reactions were incubated at 95° C. for 5 minutes and then cycled through 94° C. for 1 minute, 55° C. for 1 minute and 72° C. for 1 minute. After 30 cycles, aliquots of each reaction were analyzed by electrophoresis on an agarose gel.

For the heavy chain V-region, an amplified DNA product was only obtained when a primer pool annealing within the start of framework I replaced the signal peptide primer pool. The fragments were cloned into DNA sequencing vectors. The DNA sequence was determined and translated to give a deduced amino acid sequence. This deduced sequence was verified by reference to the N-terminal protein sequence determined experimentally. FIG. 1 shows the amino acid sequence of the CDRs of the mouse monoclonal antibody 5/44. FIGS. 2 and 3 show the DNA/protein sequence of the mature light and heavy chain V-regions of mouse monoclonal 5/44, respectively.

iii) Molecular Cloning of the PCR Fragments

The murine V-region sequences were then cloned into the expression vectors pMRR10.1 and pMRR14 (FIGS. 7 and 8). These are vectors for the expression of light and heavy chain containing DNA encoding constant regions of human kappa light chain and human gamma-4 heavy chain. The $V_L$ region was sub-cloned into the expression vector by restriction digest and ligation from the sequencing vector, using SfuI and BsiWI restriction sites, creating plasmid pMRR10(544cL) (FIG. 8). The heavy chain DNA was amplified by PCR using a 5' primer to introduce a signal peptide, since this was not obtained in the cloning strategy—a mouse heavy chain antibody leader from a different in-house hybridoma (termed 162) was employed. The 5' primer had the following sequence:

(SEQ ID NO: 51)
5'GCGCGCAAGCTTGCCGCCACCATGGACTTCGGATTCTCTCTCGTGTT

CCTGGCACTCATTCTCAAGGGAGTGCAGTGTGAGGTGCAGCTCGTCGAG

TCTGG3'.

The reverse primer was identical to that used in the original $V_H$ gene cloning. The resultant PCR product was digested with enzymes HindIII and ApaI, was sub-cloned, and its DNA sequence was confirmed, creating plasmid pMRR14(544cH) (FIG. 7). Transient co-transfection of both expression vectors into CHO cells generated chimeric c5/44 antibody. This was achieved using the Lipofectamine reagent according to the manufacturer's protocols (InVitrogen: Life Technology, Groningen, The Netherlands. Catalogue no. 11668-027).

II. Removal of Glycosylation Site and Reactive Lysine

A potential N-linked glycosylation site sequence was observed in CDR-H2, having the amino acid sequence N-Y-T (FIG. 3). SDS-PAGE, Western blotting and carbohydrate staining of gels of 5/44 and its fragments (including Fab) indicated that this site was indeed glycosylated (not shown). In addition, a lysine residue was observed at an exposed position within CDR-H2, which had the potential to reduce the binding affinity of the antibody by providing an additional site for conjugation with an agent with which the antibody may be conjugated.

A PCR strategy was used to introduce amino acid substitutions into the CDR-H2 sequence in an attempt to remove the glycosylation site and/or the reactive lysine, as shown in FIG. 4 (SEQ ID NOS:9-12 and 14). Forward primers encoding the mutations N55Q, T57A or T57V were used to remove the glycosylation site (FIG. 4, SEQ ID NOS:10-12) and a fourth forward primer containing the substitution K60R, was generated to remove the reactive lysine residue (FIG. 4, SEQ ID NO:14). A framework 4 reverse primer was used in each of these PCR amplifications. The PCR products were digested with the enzymes XbaI and ApaI and were inserted into pMRR14(544cH) (also cleaved with XbaI and ApaI) to generate expression plasmids encoding these mutants. The N55Q, T57A and T57V mutations ablate the glycosylation site by changing the amino acid sequence away from the consensus N-X-T/S while the K60R mutation replaces the potentially reactive lysine with the similarly positively.

III. Evaluation of Activities of Chimeric Genes

The activities of the chimeric genes were evaluated following transient transfection into CHO cells and determination of affinity constants by BIACORE™ analysis.

The affinities of chimeric 5/44 or its variants, which have had their glycosylation site or their reactive lysine removed, were investigated using BIA technology for binding to CD22-mFc constructs. The results are shown in FIG. 9. All binding measurements were performed in the BIACORE™ 2000 instrument (Pharmacia Biosensor AB, Uppsala, Sweden). The assay was performed by capture of CD22mFc via the immobilized anti-mouse Fc. The antibody was in the soluble phase. Samples, standard, and controls (50 μl) were injected over immobilized anti-mouse Fc followed by antibody in the soluble phase. After each cycle, the surface was regenerated with 50 μl of 40 mM HCl at 30 μl/min. The kinetic analysis was performed using the BIAevaluation 3.1 software (Pharmacia).

Removal of the glycosylation site in construct T57A resulted in a slightly faster on-rate and a significantly slower off-rate compared to the chimeric 5/44, giving an affinity improvement of approximately 5-fold. The N55Q mutation had no effect on affinity. This result was unexpected as it suggests that the removal of the carbohydrate itself apparently has no effect on binding (as with the N55Q change). The improved affinity was observed only with the T57A change. One possible explanation is that, regardless of the presence of carbohydrate, the threonine at position 57 exerts a negative effect on binding that is removed on conversion of threonine to alanine. The hypothesis that the small size of alanine is important, and that the negative effect of threonine is related to its size, is supported from the result obtained using the T57V mutation: that replacement with valine at position 57 is not beneficial (results not shown).

Removal of the lysine residue by the K60R mutation had a neutral effect on affinity, i.e. the introduction of the arginine residue removes a potential reactive site without compromising affinity.

The mutations for removal of the glycosylation site and for removal of the reactive lysine were therefore both included in the humanization design.

EXAMPLE 2

CDR-Grafting of 5/44

The molecular cloning of genes for the variable regions of the heavy and light chains of the 5/44 antibody and their use to produce chimeric (mouse/human) 5/44 antibodies has been described above. The nucleotide and amino acid sequences of the mouse 5/44 VL and VH domains are shown in FIGS. 2 and 3 (SEQ ID NOS:7 and 8), respectively. This example describes the CDR-grafting of the 5/44 antibody onto human frameworks to reduce potential immunogenicity in humans, according to the method of Adair et al., (PCT Publication No. WO 91/09967).

I. CDR-Grafting of 5/44 Light Chain

Protein sequence alignment with consensus sequences from human sub-group I kappa light chain V region indicated 64% sequence identity. Consequently, for constructing the CDR-grafted light chain, the acceptor framework regions chosen corresponded to those of the human VK sub-group I germline O12,DPK9 sequence. The framework 4 acceptor sequence was derived from the human J-region germline sequence JK1 (SEQ ID NO:18).

A comparison of the amino acid sequences of the framework regions of murine 5/44 (SEQ ID NO:7) and the acceptor sequence (SEQ ID NO:17) is given in FIG. 5 and shows that there are 27 differences between the donor and acceptor chains. At each position, an analysis was made of the potential of the murine residue to contribute to antigen binding, either directly or indirectly, through effects on packing or at the $V_H/V_L$ interface. If a murine residue was considered important and sufficiently different from the human residue in terms of size, polarity or charge, then that murine residue was retained. Based on this analysis, two versions of the CDR-grafted light chain, having the sequences given in SEQ ID NO:19 and SEQ ID NO:20 (FIG. 5), were constructed.

II. CDR-Grafting of 5/44 Heavy Chain

CDR-grafting of the 5/44 heavy chain was accomplished using the same strategy as described for the light chain. The V-domain of the 5/44 heavy chain was found to be homologous to human heavy chains belonging to sub-group I (70% sequence identity) and therefore the sequence of the human sub-group I germline framework VH1-3,DP7 was used as an acceptor framework. The framework 4 acceptor sequences were derived from human J-region germline sequence JH4 (SEQ ID NO:22).

A comparison of the 5/44 heavy chain with the framework regions is shown in FIG. 6 where it can be seen that the 5/44 heavy chain differs (SEQ ID NO:8) from the acceptor sequence (SEQ ID NO:21) at 22 positions. Analysis of the contribution that any of these might make to antigen binding led to 5 versions of the CDR-grafted heavy chains being constructed, having the sequences given in SEQ ID NO:23, SEQ ID NO:24, SEQ ID NO:25, SEQ ID NO:26 and SEQ ID NO:27 (FIG. 6).

III. Construction of Genes for Grafted Sequences

Genes were designed to encode the grafted sequences gH1 and gL1, and a series of overlapping oligonucleotides were designed and constructed (FIG. 10, SEQ ID NOS:32-47). A PCR assembly technique was employed to construct the CDR-grafted V-region genes. Reaction volumes of 100 μL were set up containing 10 mM Tris-HCl pH8.3, 1.5 mM MgCl$_2$, 50 mM KCl, 0.001% gelatin, 0.25 mM of dATP, dTTP, dCTP, and dGTP, 1 pmole each of the 'internal' primers (T1, T2, T3, B1, B2, B3), 10 pmole each of the 'external' primers (F1, R1), and 1 unit of Taq polymerase (AmpliTaq, Applied BioSystems, catalogue no. N808-0171). PCR cycle parameters were 94° C. for 1 minute, 55° C. for 1 minute and 72° C. for 1 minute, for 30 cycles. The reaction products were then run on a 1.5% agarose gel, excised and recovered using QIAGEN spin columns (QIAquick® gel extraction kit, cat no. 28706). The DNA was eluted in a volume of 30 μl. Aliquots (1 μl) of the gH1 and gL1 DNA were then cloned into the InVitrogen TOPO® TA cloning vector pCR2.1 TOPO® (catalogue no. K4500-01) according to the manufacturer's instructions. This non-expression vector served as a cloning intermediate to facilitate sequencing of a large number of clones. DNA sequencing using vector-specific primers was used to identify correct clones containing gH1 and gL1, creating plasmids pCR2.1 (544gH1) and pCR2.1(544gL1) (FIGS. 11 and 12).

An oligonucleotide cassette replacement method was used to create the humanized grafts gH4, 5, 6 and 7, and gL2. FIG. 13 shows the design of the oligonucleotide cassettes (SEQ ID NOS:56-65). To construct each variant, the vector pCR2.1 (544gH1) or pCR2.1(544gL1)) was cut with the restriction enzymes shown (XmaI/SacII for the heavy chain, XmaI/BstEII for the light chain). The large vector fragment was gel purified from agarose and was used in ligation with the oligonucleotide cassette. These cassettes are composed of 2 complementary oligonucleotides (shown in FIG. 13, SEQ ID NOS:56-65), mixed at a concentration of 0.5 pmoles/μl in a volume of 200 μl 12.5 mM Tris-HCl pH 7.5, 2.5 mM MgCl$_2$, 25 mM NaCl, 0.25 mM dithioerythritol. Annealing was achieved by heating to 95° C. for 3 minutes in a water bath (volume 500 ml) then allowing the reaction to slow-cool to room temperature. The annealed oligonucleotide cassette was then diluted ten-fold in water before ligation into the appropriately cut vector. DNA sequencing was used to confirm the correct sequence, creating plasmids pCR2.1 (5/44-gH4-7)

and pCR2.1 (5/44-gL2). The verified grafted sequences were then sub-cloned into the expression vectors pMRR14 (heavy chain) and pMR10.1 (light chain).

IV. CD22 Binding Activity of CDR-Grafted Sequences

The vectors encoding grafted variants were co-transfected into CHO cells in a variety of combinations, together with the original chimeric antibody chains. Binding activity was compared in a competition assay, competing the binding of the original mouse 5/44 antibody for binding to Ramos cells (obtained from ATCC, a Burkitt's lymphoma lymphoblast human cell line expressing surface CD22). This assay was considered the best way to compare the grafts in their ability to bind to cell surface CD22. The results are shown in FIGS. 14 and 15. As can be seen, there is very little difference between any of the grafts, all performed more effectively than the chimeric at competing against the murine parent. The introduction of the 3 additional human residues at the end of CDR-H2 (gH6 and gH7) did not appear to have affected binding.

The graft combination with the least number of murine residues gL1gH7 was selected. The light chain graft gL1 has 6 donor residues. Residues V2, V4, L37 and Q45 are potentially important packing residues. Residue H38 is at the $V_H/V_L$ interface. Residue D60 is a surface residue close to the CDR-L2 and may directly contribute to antigen binding. Of these residues, V2, L37, Q45 and D60 are found in germline sequences of human kappa genes from other sub-groups. The heavy chain graft gH7 has 4 donor framework residues (Residue R28 is considered to be part of CDR-H1 under the structural definition used in CDR-grafting (see Adair et al. (1991), PCT Publication No. WO 91/09967)). Residues El and A71 are surface residues close to the CDRs. Residue I48 is a potential packing residue. Residue T93 is present at the $V_H/V_L$ interface. Of these residues, El and A71 are found in other germline genes of human sub-group I. Residue I48 is found in human germline sub-group 4, and T73 is found in human germline sub-group 3.

The full DNA and protein sequence of both the light chain and heavy chain, including approximate position of introns within the constant region genes provided by the vectors, are shown in FIG. 16 and are given in SEQ ID NO:29 and SEQ ID NO:28, respectively, for the light chain and SEQ ID NO:31 and SEQ ID NO:30, respectively, for the heavy chain.

DNA encoding these light and heavy chain genes was excised from these vectors. Heavy chain DNA was digested at the 5' HindIII site, then was treated with the Klenow fragment of E. coli DNA polymerase I to create a 5' blunt end. Cleavage at the 3' EcoRI site resulted in the heavy chain fragment, which was purified, from agarose gels. In the same way, a light chain fragment was produced, blunted at the 5' SfuI site and with a 3' EcoRI site. Both fragments were cloned into DHFR-based expression vectors and used to generate stable cell lines in CHO cells.

EXAMPLE 3

Conjugation of NAc-Gamma Calicheamicin DMH AcBut to Humanized Anti-CD22 Antibody (G5/44)

In a typical conjugation reaction, humanized anti-CD22 antibody (G5/44) was conjugated to NAc-gamma calicheamicin DMH AcBut OSu (calicheamicin derivative) (see FIG. 17), where the target protein concentration was 7.5 mg/ml and the target calicheamicin derivative loading was 8.5 percent by weight of the protein. The target reaction pH was 8.5±0.2, and the target concentrations of the other reaction components were as follows: 50 mM N-(2-Hydroxyethyl) piperazine-N'-(4-butanesulfonic acid) (HEPBS), 37.5 mM sodium decanoate, and 9% v/v total ethanol. The reaction was conducted at 33±2° C. for one hour. Results of the analysis of this typical reaction prior to purification were as follows: Protein: 7.34 mg/ml; Calicheamicin Loading: 82.7 µg/mg; Aggregate: 93.25%; and Unconjugated Protein (LCF): 1.07% (UV Area % by HPLC).

Effect of various surfactant additives and their concentrations on product yield and purity were tested to determine their effect on the production of conjugated monomer (see Table 2). Reactions were run where everything was held constant except for the additive and its concentration. The conjugates produced from these reactions were analyzed for protein concentration, calicheamicin loading, aggregate content, and LCF. Although all n-carboxylic acids in the range of $C_6$ (hexanoate) to $C_{12}$ (dodecanoate) gave acceptable results, the best overall results (low LCF, low aggregate, and high recovery of monomeric conjugate) were obtained with decanoate in a concentration range of 30 mM to 50 mM.

TABLE 2

EFFECT OF ADDITIVE IDENTITY AND CONCENTRATION ON CONJUGATION RESULTS

| Additive/Concentration | Protein Recovery (% recovery) | Percent Aggregate | Percent LCF |
|---|---|---|---|
| Hexanoate-500 mM | 51.3 | 3.36 | 38.3 |
| Heptanoate-400 mM | 49.9 | 4.7 | 20.6 |
| Octanoate-200 mM | 57.3 | 3.27 | 10.6 |
| Nanonoate-100 mM | 54.7 | 1.41 | 0.3 |
| Decanoate-50 mM | 56.7 | 1.35 | 0.2 |
| Undecanoate-20 mM | 46.9 | 2.95 | 0.6 |
| Dodecanoate-5 mM | 65.6 | 0.78 | 7.0 |

EXAMPLE 4

Chromatographic Purification Process

I. Chromatographic Separation Processes

Although Butyl SEPHAROSE™ 4 Fast Flow was identified as the best HIC media, acceptable results can be obtained with slight alterations in the chromatographic conditions using other resins such as Octyl SEPHAROSE™ Fast Flow, PPG-600C (Tosoh Biosep), FRACTOGEL® EMD Propyl (EM Processing) and Source 15ISO (Amersham Biosciences, Piscataway, N.J.).

The starting material for the purification was a conjugation reaction mixture containing 7.2 mg/mL protein at a calicheamicin derivative loading of 83 µg/mg, with an aggregate content of 10.1% (area percent by HPLC), and an LCF content of 5.6% (area percent by HPLC)

After the conjugation reaction was completed, the reaction mixture was diluted four-fold by the addition of potassium phosphate solution to a final phosphate concentration of 0.7M (pH 8.2). After mixing, this solution was filtered through 0.45-micron filters. The diluted solution was loaded on a Butyl SEPHAROSE™ 4 Fast Flow column. The total amount of protein loaded on the column was 29 mg per ml bed volume. After a wash with 0.7 M potassium phosphate, the column was eluted using a step gradient from 0.7 M to 4 mM potassium phosphate, pH 8.2. The fractions eluted in the step gradient were pooled for further processing, with the pool consisting of monomeric conjugate with less than 1 area percent each of aggregate and LCF. This pool was loaded on a SEPHADEX™ G-25 (Amersham Biosciences) desalting column for exchange to a buffer appropriate for formulation, consisting of 20 mM Tris-HCl and 100 mM sodium chloride at pH 8.0. The purified, buffer-exchanged CMC-544 preparation had the following properties: Calicheamicin Loading: 81 μg/mg; Aggregate: 0.4% (area percent by HPLC) LCF: 0.8% (area percent by HPLC).

EXAMPLE 5

Binding Analysis of NAc-Gamma Calicheamicin DMH AcBut-G5/44 Immunoconjugate (CMC-544)

Immunoconjugate of humanized anti-CD22 antibody (G5/44) with calicheamicin (CMC-544) generated by the above conjugation process was analyzed in a binding study to determine whether the conjugate generated using the improved process had any adverse effect on antigen binding. Table 3 shows that the conjugation procedure does not have any impact on the antigen binding affinity of the antibody. CMC-544 immunoconjugate made by either the old or new conjugation procedure bound the target antigen with similar affinities, which did not differ from that of the unconjugated antibody G5/44.

TABLE 3

BINDING AFFINITIES OF CMC-544 MADE BY USING CMA-676 AND CMC-544 CONJUGATION PROCEDURES

| Anti-CD22 Antibody | $K_D$ (M) | $K_A$ (1/M) | $K_d$ (1/s) | $K_a$ (1/Ms) | Percent LCF |
|---|---|---|---|---|---|
| Humanized G5/44 | $1.30 \times 10^{-10}$ | $7.90 \times 10^9$ | $2.80 \times 10^{-5}$ | $2.20 \times 10^5$ | 100 |
| CMC-544 (21 μg/mg) (CMA-676 procedure) | $1.20 \times 10^{-10}$ | $8.10 \times 10^9$ | $6.10 \times 10^{-5}$ | $4.90 \times 10^5$ | 25 |
| CMC-544 (87 μg/mg) (CMA-544 procedure) | $1.50 \times 10^{-10}$ | $6.60 \times 10^9$ | $6.90 \times 10^{-5}$ | $4.60 \times 10^5$ | 3.3 |

Biosensor analyses were carried out using a BIACORE™ 2000 (BIAcore AB, Uppsala, Sweden). CD22mFc was covalently immobilized on the N-hydroxysuccinimide-activated carboxymethyl dextran-coated biosensor chip (CM5) using a standard amine-coupling chemistry at a protein density of approximately 2000 resonance units. Samples of CMC-544 or G5/44 were diluted in the HBS buffer (10 mM HEPES, pH 7.4, containing 150 mM NaCl, 3 mM EDTA and 0.005% polysorbate 20 (v/v)) and injected in the concentration range of 1 to 100 nM over the CD22mFc-coated biosensor chip surface at a flow rate of 30 μl/min for 3 min to allow binding. After the binding phase, dissociation of the bound antibody was monitored by washing the chip with the HBS buffer over a 15 minute period. The antigenic surface was regenerated by washing the Biosensor chip with 15 μl of the regeneration buffer (10 mM NaOH and 200 mM NaCl) for 30 seconds, followed by a stabilization time of 2 minutes before the next cycle. Kinetic constants were calculated by nonlinear least square regression analysis using a 1:1 Langmuir binding curve fitting model and BIAevaluation program (version 3.0, BIAcore). The antigen binding of CMC-544 was evaluated by surface plasmon resonance analysis using CD22mFc covalently immobilized on a biosensor chip. The results of kinetic analyses of the binding of CMC-544 and G5/44 to CD22mFc show that, after the data were fitted globally to a 1:1 Langmuir binding model with compensation for mass transfer, both CMC-544 and unconjugated G544 bound CD22 with a similar affinity (CMC-544:CD22 $K_D$=200 pM; G5/44:CD22 $K_D$=235 pM). Conjugation to calicheamicin did not impact the ability of G5/44 to effectively bind CD22mFc.

The binding of CMC-544 and G5/44 to CD22 expressed on the surface of B lymphoma cells was also examined by flow cytometry. Anti-CD33 mAb gemtuzumab (hP67.6) and its calicheamicin conjugate CMA-676 (gemtuzumab ozogamicin) were used as isotype-matched controls in this evaluation. Rituximab (RITUXAN®), a chimeric human IgG1 anti-human CD20 mAb, was used as a positive control. Purified human polyclonal IgG1 and IgG4 were also used as negative controls. Binding of CMC-544 and G5/44 to CD22 on Ramos or RL BCL was similar and distinguishable from that of human polyclonal IgG4. RL BCL displayed lower surface expression of CD22 than Ramos BCL. In contrast, the binding of CMA-676 or gL1 gH7 to either BCL was similar to that of human polyclonal IgG4 consistent with their lack of expression of CD33 (data not shown). The same cells demonstrated strong binding of anti-CD20 rituximab (RITUXAN®). Unlike hP67.6 and CMA-676, neither CMC-544 nor G5/44 demonstrated any binding to CD22$^-$ CD33$^+$ HL-60 leukemia cells (data not shown). These results suggest that the conjugation of G5/44 to calicheamicin does not affect its antigen specificity. CMC-544 specifically recognizes CD22 on human B cells, but not on murine, rat, canine, porcine or primate (cynomolgus and rhesus) B cells (data not shown).

EXAMPLE 6

Analysis of In Vitro and In Vivo Effects of CMC-544

I. In Vitro Cytotoxicity

The effect of CMC-544 made by using CMA-676 and CMC-544 processes on the in vitro growth of CD22$^+$ B-Cell lymphoma cell lines, RL, Daudi, Raji and Ramos, were compared. An isotype-matched calicheamicin conjugate targeted at human CD33 (CMA-676) was used to reflect antigen-nonspecific effects of the conjugate. The use of unconjugated N—Ac gamma calicheamicin DMH (the drug released from the conjugate upon acid hydrolysis) in this evaluation indicated that each of these cell lines used was sensitive to the lethal effects of calicheamicin. Table 4 shows the results of these evaluations based on the calicheamicin equivalence and Table 5 shows these results expressed as the concentrations of conjugated antibody protein. CD22-mediated delivery of calicheamicin to the CD22$^+$ cells was at least 10 times more efficient in killing the target cells than the unconjugated drug itself. The isotype-matched control conjugate (CMA-676) showed cytotoxicity that was either less than or similar to the unconjugated calicheamicin derivative. It is apparent from Table 4 that conjugate made by the CMC-544 conjugation process can generate equivalent cytotoxic effect at lower antibody concentrations than conjugate made by the CMA-676 conjugation process.

TABLE 4

GROWTH INHIBITION BY CONJUGATED CALICHEAMICIN
($IC_{50}$ Pm OF CALICHEAMICIN)

| B-CELL LYMPHOMA LINES | | CMC-544 PROCESS CMC-544 LOADING 65 µg/mg | CMC-676 PROCESS CMC-544 LOADING 35 µg/mg | NEGATIVE CONTROL CMA-676 LOADING 35 µg/mg | N-ACETYL GAMMA CALICHEAMICIN DMH |
|---|---|---|---|---|---|
| RL | #1 | 6 | 30 | 600 | 226 |
|  | #2 | 12 | 40 | 400 | 270 |
| Daudi | #1 | 21 | 80 | 1886 | 260 |
| Raji | #1 | 500 | ND | 2800 | 460 |
|  | #2 | 560 | 520 | 4100 | 490 |
| Ramos | #1 | 200 | 130 | ND | 700 |
|  | #2 | 260 | ND | ND | 1000 |

*ND, not determined

TABLE 5

GROWTH INHIBITION BY CONJUGATED ANTIBODY
($IC_{50}$ µg/mL OF ANTIBODY)

| B-CELL LYMPHOMA LINES | | CMC-544 PROCESS CMC-544 LOADING 65 µg/mg | CMC-676 PROCESS CMC-544 LOADING 35 µg/mg | NEGATIVE CONTROL CMA-676 LOADING 35 µg/mg | ANTIBODY CONTROL G5/44 |
|---|---|---|---|---|---|
| RL | #1 | 0.09 | 0.86 | 17.14 | >100 |
|  | #2 | 0.18 | 1.14 | 11.43 | >100 |
| Daudi | #1 | 0.32 | 2.29 | 53.89 | >100 |
| Raji | #1 | 7.69 | ND | 80.00 | >100 |
|  | #2 | 8.62 | 14.86 | 117.14 | >100 |
| Ramos | #1 | 3.08 | 3.71 | ND | >100 |
|  | #2 | 4.00 | ND | ND | >100 |

*ND, not determined

TABLE 6

ANTI-TUMOR EFFECT OF CMC-544 AGAINST RL NHL XENOGRAFTS IN NUDE MICE

| CALICHEAMICIN DOSE µg/kg | MEAN RELATIVE TUMOR GROWTH[1] | % T/C[2] | p-VALUE VS VEHICLE[3] |
|---|---|---|---|
| Vehicle | 6.74 | — | 125.00 |
| 20 | 2.87 | 43 | 125.00 |
| 40 | 1.34 | 20 | 125.00 |
| 60 | 0.58 | 9 | 125.00 |
| 80 | 0.54 | 8 | 125.00 |
| 160 | 0.21 | 3 | 125.00 |
| 320 | 0.10 | 1 | 64.00 |

[1] Relative tumor growth (RTG) computed as tumor mass at Week 3/tumor mass on day 1) for each animal
[2] 100 * (mean RTG for CMC-544 dose/mean RTG for vehicle group)
[3] p-value from one-sided t-test comparison of CMC-544 vs. vehicle, using rank-transformed RTG as the response variable. Error term for all t-tests based on pooled variance, $s^2$, across all treatment groups ($s^2 = 154.54$)

In Vivo Cytotoxicity. CMC-544 made by the CMC-544 process was further evaluated in B-cell lymphoma xenografts. In these studies, two B-cell lymphoma tumors, RAMOS and RL, were used. RL lymphoma is a non-Burkitt's NHL-derived cell line whereas RAMOS was originally derived from a Burkitt's lymphoma. In a representative experiment shown in FIG. 18, CMC-544 and its murine antibody counterpart were shown to be efficacious in inhibiting, in a dose-dependent manner, the growth of RAMOS B-cell lymphoma.

The conjugate of the humanized antibody was shown to be more potent than its murine counterpart. In this study, the lowest dose of calicheamicin conjugate capable of causing significant growth inhibition of lymphoma was 10 µg/kg of conjugated NAc-gamma calicheamicin DMH. In contrast, the unconjugated antibody, G5/44, at 10 mg/kg administered intraperitoneal on a similar schedule as conjugates had no effect on tumor growth.

Similar studies were carried out using the RL lymphoma model. Table 6 shows the combined analyses of three independent experiments in which the anti-tumor effects of CMC-544 were assessed on RL NHL tumors staged to 300-400 mg in size in nude mice. CMC-544 in a dose-dependent manner caused tumors to regress over a 3-week time frame. The minimally effective dose of CMC-544 in the RL lymphoma model was established from statistical analyses of these studies to be 20 µg/kg based on calicheamicin content. There were no deaths in any of these three studies. Higher doses (60-320 µg/kg) of CMC-544 caused almost complete regression of RL lymphoma. Taken together, the results obtained with the two B-cell lymphoma models clearly demonstrate the capability of CMC-544 to cause tumor regression.

The ability of CMC-544 made by the new procedure to inhibit growth of large established B-cell lymphoma xenografts using both the RAMOS and RL lymphoma models was also investigated. The tumors were allowed to grow and staged to 1.5 or 2 g of tumor mass after which CMC-544 or an isotype-matched negative control conjugate (CMA-676) were administered intraperitoneally at the dose of 160 µg/kg of conjugated calicheamicin keeping the original schedule of dosing on days 1, 5 and 9.

The same schedule of dosing was shown earlier to cause long lasting regression of small staged tumors (see Table 6). As shown in FIG. 19, administration of CMC-544 to large RAMOS lymphoma-bearing mice caused gradual regression of the preexisting lymphoma mass and by day 20, 3 out of 4 tumor-bearing mice were tumor-free. Monitoring these tumor-freed mice up to day 50 did not indicate any re-growth of regressed RAMOS lymphoma. In contrast, an isotype matched control, CMA-676, had no effect on the tumor growth. Four out of five CMA-676-treated large tumor-bearing mice had to be sacrificed before day 15 because their tumor burden reached close to 15% of their body weight.

A similar experiment using CMC-544 was carried out in the RL lymphoma model. Intraperitoneal administration of CMC-544 at a dose of 160 µg/kg on a similar schedule as described before caused >90% regression of the pre-existing mass of RL lymphoma within 30 days. However by day 45, 2 mice in this group with shrunken lymphomas showed re-growth of the tumors. These results indicate that CMC-544 is able to cause regression of small, as well as large, established lymphomas. In a small number of studies not shown here, RL lymphomas that re-grew sporadically after the initial CMC-544-induced regression were retreated with CMC-544 again. These studies showed that the RL tumors were still responsive to the second course of the treatment with CMC-544 and regressed again. Thus, the treatment with CMC-544 can be effective against both small and large masses of B-cell lymphomas with the potential for repeat therapy.

II. In Vivo Comparison of Conjugate Made with CMA-676 and CMC-544 Conjugation Processes FIG. 20 shows the results of a representative experiment in which staged RL lymphoma-bearing mice received two different doses (80 and 320 µg/kg of conjugated calicheamicin) of CMC-544 made using the CMA-676 conjugation process and the CMC-544 conjugation process using the standard dosing schedule. The observed anti-tumor efficacy was dose-dependent as expected and there was no difference in the efficacies of either of the two CMC-544 preparations. In contrast, unconjugated N Acetyl-gamma calicheamicin DMH administered intraperitoneally at 160 µg/kg was inactive. However, it should be emphasized that for each dose of conjugated calicheamicin, the quantity of antibody protein administered in the form of a conjugate was four times higher for CMC-544 made by the CMA-676 process versus that made by the CMC-544 process. Since the calicheamicin content of the targeted conjugate is primarily responsible for causing the anti-tumor effect, it is possible to deliver the required quantity of calicheamicin via the conjugate made by the new procedure using much smaller quantities of the targeting antibody. The increased loading of the conjugate made by the CMC-544 process is, in effect, due to the lack of significant amounts of the low conjugated fraction (LCF).

III. Treatment of Rituximab (RITUXAN™)-Resistant Tumors

The next question to be explored was whether the B-cell lymphomas grown after the discontinuation of the commercially available, anti-CD20 rituximab (RITUXAN®) treatment would still responsive to the CMC-544 treatment. To this end, developing (unstaged) RL lymphomas were treated with rituximab (RITUXAN®) for three weeks. As long as the rituximab (RITUXAN®) therapy was continued, the growth of RL lymphoma was inhibited. Upon cessation of rituximab (RITUXAN®) therapy, RL lymphomas grew rapidly to the size of ~1 g mass at which time they were treated with CMC-544 at the intraperitoneal dose of 160 µg/kg. As shown in FIGS. 21 and 22, these RL lymphomas were still responsive to CMC-544 with 80% of mice becoming tumor-free by day 60. Thus, CMC-544 is able to cause regression of B-cell lymphomas with three doses that could only be inhibited by the continuous dosing of rituximab (RITUXAN®).

EXAMPLE 7

In Vitro and In Vitro In Vivo Effect of CMC-544

I. Binding and Toxicity Studies

CMC-544 was evaluated for its binding to CD22 and also for its activity in in vitro and in vivo models. CMC-544 was also compared to CMA-676, an isotype-matched control conjugate of hP67.6 (IgG4) with AcBut linked calicheamicin, and to rituximab (RITUXAN®), a chimeric IgG1 anti-CD20 mAb, (IDEC Pharmaceuticals, San Diego, Calif.), which is commercially available and was purchased from Medworld Pharmacy (Chestnut Ridge, N.Y.). The following antibodies were used in the G5/44 binding domain studies: BU12 (Celltech, Slough, UK); BLCAM, HD239 (Santa Cruz Biotech, Santa Cruz, Calif.); RFB-4 (Ancell Corp, Bayport, Minn.); SHCL-1, Leu 14 (Becton Dickinson, Franklin Lakes, N.J.); 4 KB128 and To 15 (Dako Corp, Carpinteria, Calif.); M6/13 and M5/44 (Celltech, Slough, UK). Additional antibodies used in the blocking studies were SJ10 (Immunotech, Fullerton, Calif.) and M17.1.1, M19.1.1, M38.1.1 (Celltech, Slough, UK). Cell lines for the studies including Burkitt's lymphoma cell line Ramos (CRL-1923) and the Non-Hodgkin's lymphoma (NHL) cell line RL (CRL-2261) were all obtained from the American Type Culture Collection. The cell lines were determined to be mycoplasma free by a polymerase chain reaction mycoplasma detection assay (ATCC, Manassas, Va.). The cell lines were maintained as suspension cultures in RPMI medium plus 10% FBS, 10 mM HEPES, 1 mM sodium pyruvate, 0.2% glucose, Penicillin G sodium 100 U/ml, and streptomycin sulfate 100 µg/ml.

Whether or not G5/44 can inhibit the binding of murine mAbs of known specificity to CD22 was evaluated by BIACORE™ analysis using Fc-CD22 immobilized to a BIACORE™ CM5 chip. The surface plasmon resonance units (RU) obtained with and without prior saturation of the immobilized Fc-CD22 with G5/44 were compared. Biomolecular interaction analysis was performed using a BIACORE™ 2000. Antibodies were passed over a blank control surface (flowcell 1, serves as a control, no protein was coupled) and the test surface of Fc-CD22 (flowcell 2) immobilized on a CM5 sensor chip via amine coupling chemistry to a level of 9,042 RU. The resultant sensorgram was the response (RU) on flowcell 2 minus the response (RU) on flowcell 1. A second sensorgram was obtained by first saturating the flowcells with G5/44 (100 µg/ml) before the introduction of murine mAbs against CD22 that had been previously characterized for their binding. Immediately upon measuring the G5/44 response, murine anti-CD22 mAbs were individually perfused without removing G544. The second combined response generated due to the binding of murine anti-CD22 mAb to G5/44-coated CD22 was also recorded. If the murine antibody bound to CD22 at sites unrelated to those occupied by G5/44, then the combined responses would be additive. If the binding of G5/44 to CD22 interfered with or prevented the binding of the second antibody, then the combined responses would not be additive. Each of the second combined measurements were corrected for the "off-rate" of the G5/44:CD22 interaction.

G5/44 blocked the binding of only those antibodies that bound to epitope A/Ig-like domain 1 of CD22 (SHCL1 Leu 14 and HD239), indicating that G5/44 also binds in this domain of CD22. Antibodies that bind to epitope B/Ig-like domain 3 of CD22 (RFB-4), epitope C/Ig-like domain 4 of CD22 (To 15) and Ig-like domain 2 of CD22 (4 KB128), were not blocked by G5/44. These results indicate that G5/44-binding site on CD22 is located on the first Ig-like domain because it prevents the binding of those anti-CD22 mAbs that recognize the first Ig-like domain of CD22 (epitope A). Another anti-CD22 antibody, M6/13 (Celltech, Slough, UK), of unknown subspecificity was also blocked by G5/44 (Celltech, Slough, UK), thus mapping the binding site of M6/13 to epitope A/Ig-like domain 1 of CD22. The antibody M5/44, the murine parent of G5/44 that has the same specificity as G5/44, inhibits the binding of G5/44, and serves as a positive control. Anti-CD19 antibody BU12 serves as a negative control in these evaluations. The results are summarized in Table 7.

TABLE 7

BINDING OF MURINE ANTI-CD22 M/AB WITH DEFINED SPECIFICITIES TO
G544-PRETREATED FC-CD22. BINDING RESPONSE EXPRESSED AS SURFACE
PLASMON RESONANCE UNITS (RU)

| Antibody | Epitope Ig Domain of CD22 | Response 1 with G544 | Response 2 with G544 | Response 3 (Response 2-1) | Response 3 adjusted for "OFF" rate of G544 | Binding of 2nd mAb without G544 adjusted for background | Inhibition by G544 (%) |
|---|---|---|---|---|---|---|---|
| Anti-CD22 Leu 14 | A 1, 2 | 654.3 | 579.8 | −74.5 | 9 | 29.3 | 69 |
| Anti-CD22 HD239 | A 1 | 710.5 | 628.7 | −81.8 | 1.7 | 19.3 | 91 |
| Anti-CD22 M 6/13 | ? ? | 710.0 | 652.7 | −57.3 | 26.2 | 152.4 | 83 |
| Anti-CD22 RFB-4 | B 3 | 703.5 | 1108.5 | 405 | 488.5 | 534 | 9 |
| Anti-CD22 4KB128 | ? 2 | 691.0 | 1343.5 | 652.5 | 736.0 | 738.8 | 0 |
| Anti-CD22 To 15 | C 4 | 676.9 | 1163.6 | 486.7 | 570.2 | 614.6 | 7 |
| Anti-CD22 M5/44 | Positive Control | 725.1 | 679.3 | −45.8 | 37.7 | 613.9 | 94 |
| Anti-CD22 BU12 | Negative Control | 686.2 | 602.7 | −83.5 | 0 | 0 | 0 |

Using murine mAbs of known binding specificities for individual domains to CD22, the ability of G5/44 to block the binding of these antibodies to B cells was investigated. Additionally, the ability of the mAbs to block the binding of G5/44 to B cells was also investigated. In these studies, $1\times10^5$ Ramos cells were first exposed to murine anti-CD22 antibody (10 μg/ml humanized G5/44 or mouse monoclonal anti-CD22) for 1 hour at 4° C. prior to the exposure of the cells to G5/44 (10 μg/ml). Cells were incubated for an additional 1 hour at 4° C. After the antibody treatments, B cells were pelleted and washed with PBS-1% BSA and the appropriate secondary antibody was added (either FITC-goat anti-human (heavy and light chain) or FITC-goat anti-mouse (heavy and light chain)) at 100 μl of a 1:100 dilution in PBS-1% BSA for 30 minutes at 4° C. Cells were again pelleted, washed, and resuspended in PBS-1% BSA and added to a tube containing 250 μl of PBS-1% formaldehyde. Fluorescence intensity associated with cells was measured by flow cytometry using BD FACSORT™ flow cytometer.

The results showed that prior exposure of G5/44 to CD22+ B cells resulted in significant inhibition of the subsequent binding of anti-CD22 mAbs M5/44 and M6/13. In contrast, the binding of anti-CD22 mAbs RFB4, To15, HD239, and 4 KB to B cells was not inhibited by G5/44. The lack of significant inhibition of HD239 binding to B cells by G5/44 as detected by flow cytometry was unexpected, especially since the BIACORE™ analysis indicated that G5/44 can block the binding of HD239 to CD22. The lack of strong inhibition of HD239 binding by G5/44 may be explained based on the differences in their relative affinities for CD22. When the above murine anti-CD22 mAbs were examined for their ability to inhibit the binding of G5/44 to CD22+ B cells, SHCL1 and M6/13, but the not other anti-CD22 mAbs, inhibited the binding of G5/44. The binding epitopes of HD239 and SHCL1 have been mapped to the first Ig-like domain of CD22. However, the epitopes recognized by M6/13 or M5/44 have not been mapped. The blocking studies detailed above indicate that the above antibodies recognize epitopes located on the first Ig-like domain of CD22, collectively known as epitope A.

Twenty thousand Ramos cells were incubated with various doses of CMC-544 with and without rituximab (RITUXAN®) for 96 hours. After 96 hours, cell viability was measured by propidium iodide exclusion analyzed by flow cytometry. The mean viability of 3 to 6 wells was calculated and the dose response inhibition of cell viability was calculated for the various treatments. The background response inhibition of cell viability was calculated from a zero concentration of CMC-544. Logistic regression was used to test whether CMC-544 caused a statistically significant dose-dependent inhibition of Ramos cell growth over the dose range of 0.01 to 3 ng calicheamicin DMH/ml. Logistic regression was also used to determine whether the interaction of CMC-544 with rituximab (RITUXAN®) was statistically significant. Median inhibitory concentrations ($IC_{50}$) were also computed and the effectiveness of each treatment relative to the treatment with CMC-544 alone was recorded. The statistical analysis was conducted using the PROBIT procedure in SAS version 8.2.

The results of the study showed that CMC-544 caused a dose-dependent inhibition of Ramos cell growth over the dose range of 0.01 to 3 ng calicheamicin DMH/ml. The median inhibitory concentration ($IC_{50}$) of CMC-544 alone was 0.029 ng/ml. The concentrations of 2, 20, and 200 μg/ml of rituximab (RITUXAN®) were added to CMC-544 treated cells to determine whether the interaction of rituximab (RITUXAN®) with the cytotoxicity activity of CMC-544 is statistically significant. Rituximab (RITUXAN®), added at 20 and 200 µg/ml without CMC-544, had no significant effect on cell growth by itself (111.7% and 94.0% of vehicle growth, respectively). In combination with CMC-544, all three concentrations of (RITUXAN®) produced statistically significant ($p<0.05$) shifts to the left in the slope and intercept of the CMC-544 dose-response curve. The combination with 2 and 200 µg/ml of rituximab produced the largest shifts in the dose-response curves. These 2 curves were not statistically different from each other but were significantly different ($p<0.05$) from the 20 µg/ml dose combination. A second study (results not reported) confirmed the results observed in the first study. The median inhibitory concentrations for the combinations of 2, 20, and 200 µg/ml of rituximab (RITUXAN®) plus CMC-544 are 0.0072, 0.0081, and 0.0072 ng/ml, respectively. The median inhibitory concentrations of CMC-544 plus rituximab (RITUXAN®) are approximately four-fold more potent than the $IC_{50}$ of CMC-544 alone.

II. In Vivo Anti-Tumor Activity Subcutaneous Xenografts and Systematically Disseminated B-Cell Lymphomas in SCID Mice Female, athymic nude mice, 18-22 g, were given total body irradiation (400 rads). Irradiation further suppressed the immune system of the mice to enhance tumor take. Three days after irradiation, mice were injected subcutaneously with 107 RL cells in MATRIGEL™ (Collaborative Biomedical Products, Belford, Mass., diluted 1:1 in RPMI medium) in the dorsal, right flank. When the tumors reached the appropriate size, (0.3 g, typically 21 days later), CMC-544, rituximab (RITUXAN®) or CHOP therapy (see below) was administered in sterile saline, 0.2 ml/mouse ip. The initial day of drug administration was considered day 1. Two additional doses were given on days 5 and 9 (treatment=q4Dx3). CHOP therapy consisted of cyclophosphamide (C), (CYTOXAN®, Bristol-Meyers Squibb Co., Princeton, N.J.) 40 mg/kg ip; doxorubicin HCl (H), (Sigma-Aldrich, Co., St Louis, Mo.) 3.3 mg/kg ip; vincristine (0), (GensiaSicor Pharmaceuticals, Irvine, Calif.) 0.5 mg/kg ip; and prednisone (P), (Roxane Labs., Columbia, Ohio) 0.2 mg/kg po. CHO was administered according to the same dosing schedule as both CMC-544 and rituximab (RITUXAN®) (q4Dx3) while prednisone was administered orally every other day for 5 doses (q2Dx5). Tumors were measured at least once a week and calculated as tumor mass (g)=0.5 (tumor width/2)(tumor length). Group means SEM were calculated and compared to the vehicle-treated group for statistical significance using multiple T-tests. Group means were recorded up to 50 days or until either a mouse died (which disrupted the group mean) or the tumor grew too large (>3.5 g) and the mouse had to be euthanized. After this time, tumor mass was reported only for each individual mouse in all treatment groups. The number of tumor free mice at the end of each study for each treatment group was also recorded.

To determine the effect of CMC-544 alone or in combination with other bioactive agents on disseminated lymphomas, the SCID mouse model was used. Male SCID mice (CB17 SCID), 20-25 g, were injected with 106 Ramos cells through the tail vein (0.2 ml). Either 3 or 9 days after cell injection, the mice were administered vehicle, conjugates (CMC-544 or CMC-676), or rituximab (RITUXAN®) ip, for a total of 3 doses. For the day 3 treatment schedule, mice were dosed on days 3, 7, and 11. For the day 9 treatment schedule, mice were dosed on days 9, 13 and 17. In the day 9 treatment schedule, combinations of CMC-544 and rituximab (RITUXAN®) were also given as described below. Mice were monitored daily for the presence of hind limb paralysis at which time they were killed. Seven to 10 mice per treatment group were used. The group average survival time (±SD), median, minimum, and maximum survival times were all calculated. The difference in survival distribution between groups was determined by using a nonparametric Log-rank test with significance reported at the 0.05 level. The survival curves were constructed using the Kaplan-Meier method.

The initial study examined the effect of two different dosing schedules on survival times of the SCID mice with the disseminated lymphoma. The first study looked at initiating drug dosing 3 days after the tumor cells were injected intravenously (developing model), while the second study delayed drug dosing until 9 days post tumor cell injection (established model). In each study, CMC-544 (160 µg/kg), CMA-676 (160 µg/kg), or rituximab (RITUXAN®) (20 mg/kg) were administered 3 doses ip, 4 days apart (Q4Dx3). In the developing model, vehicle-treated mice had an average survival time of 27 days (FIG. 23, Table 8). CMA-676, the isotype-matched control for CMC-544, did not increase survival time significantly ($p>0.05$). CMC-544 significantly increased survival time to 41 days while rituximab had a profound effect, increasing survival time to >125 days (significantly greater than CMC-544, $p<0.05$). Delaying dosing until the tumor cells had an opportunity to circulate (homing) and deposit in the target tissues (established model) changed the results for CMC-544 and rituxumab (RITUXAN®). CMA-676 again had no significant effect on survival times (FIG. 24, Table 8). Rituximab (RITUXAN®) increased the average survival time to 62.6 days while CMC-544 improved the average survival time to 83.5 days. There was no significant difference between the effects of CMC-544 and rituximab (RITUXAN®) in the established model.

TABLE 8

DESCRIPTIVE MEASURES OF SURVIVAL TIMES

| Study | Compound | Average Survival Time | Median Survival Time | Standard Deviation | Minimum Survival Time | Maximum Survival Time | Number of Animals |
|---|---|---|---|---|---|---|---|
| Developing Model | CMA-676 | 32.9 | 34.0 | 3.9 | 28.0 | 36.0 | 7 |
| | CMC-544 | 41.0 | 38.0 | 10.1 | 32.0 | 60.0 | 7 |
| | Rituximab | 128.4 | >130.0 | 4.7 | 119.0 | >130.0 | 7 |
| | Vehicle | 27.2 | 28.0 | 1.4 | 25.0 | 28.0 | 8 |
| Established Model | CMA-676 | 33.7 | 31.0 | 4.6 | 30.0 | 42.0 | 7 |
| | CMC-544 | 83.5 | 76.5 | 41.6 | 34.0 | >130.0 | 8 |
| | Rituximab | 62.6 | 37.0 | 46.2 | 31.0 | >130.0 | 7 |
| | Vehicle | 30.5 | 29.0 | 3.6 | 27.0 | 36.0 | 8 |

A preliminary study was conducted to determine if rituximab (RITUXAN®) had any effect, either positive or negative, on the survival response of CMC-544. CMC-544 (160 µg) was administered with and without rituximab (RITUXAN®) (20 mg/kg, labeled the high dose drug combination (HD)). In addition, lower doses of CMC-544 (80 µg/kg) were co-administered with lower doses of rituximab (RITUXAN®) (10 mg/kg). The compounds were not given separately at the respective 80 µg/kg or 10 mg/kg doses due to the limited number of mice in the study. This combination, CMC-544 (80 µg/kg) with rituximab (RITUXAN®) (10 mg/kg), was labeled the medium dose combination (MD) and was run to determine the feasibility of lower dose combinations of drugs on SCID mouse survival. CMC-544 (160 µg/kg) and rituximab (RITUXAN®) (20 mg/kg), administered alone, performed as reported in the established model above. Each prolonged average survival times to 58.5 and 50.5 days, respectively (FIG. 25, Table 9). In combination, the average survival time was slightly (though not statistically significant, p>0.05) improved to 64.4 days for the high-dose combination. The medium dose combination of 80 µg/kg CMC-544 and 10 mg/kg rituximab (RITUXAN®) significantly improved (p<0.05 vs vehicle-treated) survival time to an average of 92.4 days. These results suggested that lower dose combinations of CMC-544 and rituximab (RITUXAN®) were warranted.

TABLE 9

DESCRIPTIVE MEASURES OF SURVIVAL TIMES FOR INITIAL COMBINATION STUDIES

| Treatment | Average Survival Time | Median Survival Time | Standard Deviation | Minimum Survival Time | Maximum Survival Time | Number of Animals |
|---|---|---|---|---|---|---|
| CMC MD + Ritux MD | 92.4 | >100.0 | 16.0 | 62.0 | >100.0 | 10 |
| CMC HD + Ritux HD | 64.4 | 58.5 | 26.7 | 29.0 | >100.0 | 10 |
| CMC-544 | 58.5 | 34.5 | 35.8 | 27.0 | >100.0 | 10 |
| Rituximab | 50.5 | 41.0 | 26.4 | 30.0 | >100.0 | 10 |
| Vehicle | 31.0 | 27.0 | 9.7 | 27.0 | 56.0 | 9 |

CMC MD = CMC-544 medium dose, 80 µg/kg
CMC HD = CMC-544 high dose, 160 µg/kg
Ritux MD = Rituximab medium dose, 10 mg/kg
Ritux HD = Rituximab high dose, 20 mg/kg A further combination study with CMC-544 and rituximab (RITUXAN®) was conducted. The following treatment groups were run: CMC-544 at 40, 80 and 160 µg/kg; rituximab (RITUXAN®) at 5, 10, and 20 mg/kg; and CMC-544 at 40 µg/kg plus rituximab (RITUXAN®) 5 mg/kg, CMC-544 at 80 µg/kg plus rituximab (RITUXAN®) 10 mg/kg, and CMC-544 at 160 µg/kg plus rituximab (RITUXAN®) 20 mg/kg. All doses of rituximab (RITUXAN®) slightly improved average survival time to the range of 33-40 days, (all doses p<0.05 compared with the vehicle-treated average survival time of 25.8, FIG. 26, Table 10). The CMC-544 high dose, 160 µg/kg, improved average survival time to 85 days, consistent with the results reported in the earlier two studies. Combining CMC-544 with rituximab (RITUXAN®) made no significant improvement in the survival times (FIG. 27, Table 10). The two lower doses of CMC-544 (80 and 40 µg/kg) each significantly improved (p<0.05) average survival times above that of the high dose CMC-544. For the 40 and 80 µg/kg doses of CMC-544, 90% and 80% of the mice, respectively, were still surviving at 125 days. Both drug combination groups had 100% of the mice survive until day 125. Lower doses of CMC-544 are more efficacious than the high dose of 160 µg/kg.

Rituximab (RITUXAN®), in combination with CMC-544, had no obvious effect on CMC-544's activity in the disseminated B-cell model in SCID mice at the doses tested (see above). Whether CMC-544, co-administered with rituximab (RITUXAN®) resulted in either enhancement or inhibition of anti-tumor activity was also evaluated using the subcutaneous RL B lymphoma xenograft model in Balb/c nude mice. In the subcutaneous B lymphoma model, tumors were staged to an average tumor mass of 300 mg after which the two therapeutics under study were administered IP. CMC-544 was used at 20 or 80 µg/kg Q4Dx3 with or without rituximab (RITUXAN®) (20 mg/kg Q4Dx3). The co-administration of rituximab (RITUXAN®) neither enhanced nor inhibited significantly (p>0.05) the therapeutic efficacy of CMC-544 (FIG. 28). Rituximab (RITUXAN®), administered alone, inhibited RL B lymphoma growth (57% inhibition of tumor growth at day 20, p<0.05 vs vehicle-treated) in this study, similar to that observed with the lower dosage of CMC-544.

The combination chemotherapeutic regimen CHOP (cyclophosphamide, doxorubicin, vincristine, and prednisone) is the most commonly used treatment modality for non-Hodgkin lymphoma patients. The anti-tumor effect of CHOP was compared with that of CMC-544 in established RL B lymphoma xenografts. Individual components of the CHOP regimen were used at their respective maximum tolerated doses assessed in nude mice (data not reported) and were as follows: Cyclophosphamide (C) 40 mg/kg IP, doxorubicin (H) 3.3 mg/kg IP, vincristine (O) 0.5 mg/kg IP, and prednisone (P) 0.2 mg/kg PO. CHO were administered Q4Dx3 and P was administered PO, Q2Dx5. CMC-544 was administered IP, Q4Dx3 at a dosage of 160 µg/kg calicheamicin equivalents. The CHOP treatment initially caused a significant inhibition of the RL B lymphoma growth (FIG. 29). However, 3 weeks later, tumors re-grew with similar growth rates as the vehicle-treated group. In contrast, the antitumor effect of CMC-544 was complete and lasted throughout the experimental period. These results suggest that CMC-544, at a dose significantly lower than the maximum nonlethal dose in nude mice, was more efficacious than the CHOP combination therapy.

These studies showed that rituximab (RITUXAN®), added to CMC-544 caused a significant increase in CMC-544's cytotoxic activity observed with Ramos B lymphoma cells. A synergistic interaction in Ramos cells for rituximab (RITUXAN®) and glucocorticoids was also recently reported. Additionally, a synergistic growth inhibition in 4 of 8 additional cell lines was observed with rituximab (RITUXAN®) when given in combination with 10 µM dexamethasone.

Rituximab (RITUXAN®) by itself, 0.4 to 10 µg/ml, was reported to cause a significant, though small (18% maximum) inhibition of Ramos cell growth. Additionally, it was active in 6 of 8 B-cell non-Hodgkin lymphoma cell lines when incubated at 10 µg/ml (48 h incubation). Ghetie et al, showed that rituximab (RITUXAN®), 10 µg/ml, caused a 6.2% increase in apoptosis (versus 3.5% in vehicle-treated cells) after 24 hours incubation with Ramos cells. In the current studies, rituximab (RITUXAN®), at doses 20 and 200 µg/ml had no effect on Ramos cell growth when administered alone. In mice, there was no evidence of any interaction between CMC-544 and rituximab (RITUXAN®) in either the disseminated model or the subcutaneous xenograft model. The drug combinations tested did not interfere with each other's effects nor enhance them. Whether reducing the doses of each drug in the disseminated model will change this observation needs to be determined.

The disseminated B-cell lymphoma model with Ramos cells has been described by Flavell et al. Median survival times for vehicle-treated mice were reported to be 34-36 days. Mice developed hind-limb paralysis and progressed to becoming moribund, dying soon after. Histological analysis of the organs revealed that the most commonly involved organs were the adrenal gland, spleen and sub-arachnoid space. The sub-arachnoid space infiltrate frequently extended into the brain. Rituximab (RITUXAN®) performed well when administered in the early phase of the disease process for the disseminated SCID mice (FIG. 23), but was less impressive when administered at day 9 in the established phase of the model (FIG. 24). Rituximab (RITUXAN®), being of the IgG1 isotype, most likely works through the mouse host effector mechanisms. These mechanisms include complement-mediated cytotoxicity and/or antibody dependent cellular cytotoxicity through recruitment of natural killer cells that are present in SCID mice. The injected Ramos tumor cells are probably more susceptible early on to the host immune mechanisms that are activated by rituximab. (RITUXAN®), before the cells have an opportunity to infiltrate into the affected organs. The unconjugated G5/44 antibody (the targeting molecule in CMC-544) had not yet been tested in the disseminated tumor model in SCID mice, but it had no effect when administered in subcutaneous xenografts. G5/44, being of the IgG4 isotype, would not be expected to activate the host effector mechanisms and, therefore, would not produce anti-tumor activity.

Calicheamicin conjugated G5/44 (CMC-544) behaved in the opposite fashion than rituximab (RITUXAN®), producing better results when administered in the established phase of the disease. The reason for CMC-544 performing better in the established phase is not clear, but the established phase more closely represents the linical situation. CMA-676, the isotype matched, nonbonding control conjugate, did, no have any significant effects on the average survival times. The results in the disseminated SCID model clearly suggest that the doses of CMC-544 need to be reduced to determine the maximum efficacious dose (MED). The 160 µg/kg dose was less active than the lower doses of 80 and 40 µg/kg. It is not clear why this is so but the 160 µg/kg dose may be well over the MED. Further studies are planned to address this issue.

Mohammad et al., used CHOP therapy (Cyclophosphamide (C) 40 mg/kg IV, doxorubicin (H) 3.3 mg/kg IV, vincristine (O) 0.5 mg/kg IV, and prednisone (P) 0.2 mg/kg PO) in a model of subcutaneous xenografts with a diffuse large cell lymphoma cell line, DLCL. The doses used for the CHOP therapy were determined to be their maximum tolerated dose. Therapy, CHO given once IV and P, given daily for 5 days, was rated 'active', producing a T/C of 25.8%. No tumor cures were recorded. The results in the model described by Mohammad et al., appear similar to those observed with CHOP therapy (administered IP, Q4Dx3) in the RL model described herein. In neither study did CHOP produce long-term cures, unlike CMC-544.

TABLE 10

DESCRIPTIVE MEASURES OF SURVIVAL TIME FOR COMBINATION STUDIES

| Treatment | Average Survival Time | Median Survival Time | Standard Deviation | Minimum Survival Time | Maximum Survival Time | Number of Animals |
|---|---|---|---|---|---|---|
| CMC-544 40 µg/kg | 118.90 | 125.00 | 19.29 | 64.00 | 125.00 | 10 |
| CMC LD + Ritux LD | 125.00 | 125.00 | 0.00 | 125.00 | 125.00 | 10 |
| CMC-544 80 µg/kg | 118.22 | 125.00 | 17.86 | 71.00 | 125.00 | 9 |
| CMC MD + Ritux MD | 125.00 | 125.00 | 0.00 | 125.00 | 125.00 | 10 |
| CMC-544 160 µg/kg | 85.22 | 82.00 | 40.37 | 35.00 | 125.00 | 9 |
| CMC HD + Ritux HD | 91.30 | 100.00 | 36.31 | 44.00 | 125.00 | 10 |
| Rituximab 5 mg/kg | 40.70 | 36.50 | 9.57 | 34.00 | 64.00 | 10 |
| Rituximab 10 mg/kg | 33.80 | 34.00 | 3.26 | 29.00 | 41.00 | 10 |
| Rituximab 20 mg/kg | 40.50 | 34.00 | 15.45 | 31.00 | 82.00 | 10 |
| Vehicle | 25.80 | 25.00 | 3.12 | 22.00 | 34.00 | 10 |

CMC LD = CMC-544 low dose, 40 µg/kg
CMC MD = CMC-544 medium dose, 80 µg/kg
CMC HD = CMC-544 high dose, 160 µg/kg
Ritux LD = Rituximab low dose, 5 mg/kg
Ritux MD = Rituximab medium dose, 10 mg/kg
Ritux HD = Rituximab high dose, 20 mg/kg

EXAMPLE 8

Stable Formulations of CMC-544

Stable formulations of CMC-544 for in vivo administration were prepared by adding diluents, excipients, carriers and stabilizers. Following HIC chromatography, the chromatographic fractions are assayed by SEC-HPLC and multiwavelength UV analysis. Appropriate fractions were selected for pooling on the basis of the above analysis, which provided information on aggregate content, protein concentration, and calicheamicin loading. Excipients, stabilizers, bulking agents and buffering agents were added to stabilize the solution. Since CMC-544 can undergo degradation via a number of degradation pathways, physical instabilities need to be considered in the development of formulations. One of the main considerations in the development of formulations is that the rate of hydrolysis of calicheamicin from the antibody must be minimized while the physical and chemical integrity of the anti-CD22 antibody must be maintained. In addition, precipitation of the calicheamicin-antibody conjugate, which can occur under certain pH and concentration conditions, needs to be minimized.

In developing a formulation of a monomeric calicheamicin derivative-antibody conjugate, the pH of the formulation is critical, as this minimizes degradation and physical instability. A pH of 8.0 was selected to minimize hydrolysis of calicheamicin and maintain adequate solubility of the conjugate. Additional data, obtained using SDS-PAGE and antigen binding ELISA, indicated that the significant structural integrity and specificity of the antibody are maintained at a pH of 8.0. Consequently, tromethamine was chosen as a buffering agent to maintain a pH of 8.0. An alternative buffer could include dibasic sodium or potassium phosphate. The range of buffer concentration can be 5 to 50 mM. A preferred pH range of 7.5 to 8.5 is suggested for optimum stability/solubility. The current pH specification for the finished product is 7.0-9.0.

Although the stability of the buffered conjugate solutions is adequate for the short time, long-term stability is poor. Lyophilization is used to improve the shelf life of the conjugates. The problems associated with lyophilization of a protein solution are well documented, and the loss of secondary, tertiary and quaternary structure can occur during freezing and drying processes. Sucrose is included in the formulation to act as an amorphous stabilizer of the conjugate and maintain the structural integrity of the antibody during freezing and drying. Concentrations of 1.5-5.0% w/v sucrose have been used. In addition, a polymeric bulking agent, such as Dextran 40 or hydroxyethyl starch can be incorporated to enhance the appearance and physical rigidity of the lyophilized cakes at a concentration of 0.5-1.5% by weight. These materials form lyophilized cakes at relatively low concentrations and can be used to minimize the overall solids content of the lyophilized formula, thus permitting more rapid freeze drying. Formulation studies have used a Dextran 40 concentration of 0.9% by weight.

Polysorbate 80 is included in the formulation to enhance the solubility of the conjugate. A preferred concentration of 0.01% is used with a potential range of 0.005-0.05%. TWEEN® is also added to the formulation at a concentration of 0.01-0.05% by volume.

An electrolyte may also be present in the formula and may be used to improve the efficiency of the final purification process. Sodium chloride is typically used at a concentration of 0.01M to 0.1M. Additional electrolytes such as sodium sulfate may also be used as a replacement for sodium chloride since it may be more easily lyophilized. Optimally, the final CMC-544 solution comprises 1.5% sucrose (by weight), 0.9% Dextran 40 (by weight), 0.01% TWEEN® 80, 50 mM sodium chloride, 0.01% polysorbate 80 (by weight) and 20 mM tromethamine.

A representative formula for the solution prior to lyophilization is presented below: CMC-544 0.5 mg/mL, sucrose 1.5% by weight, Dextran 40 0.9% by weight, sodium chloride 0.05M, TWEEN® 0.01-0.05% by volume, polysorbate 80 0.01% by weight, tromethamine 0.02M, pH 8.0, and water. The solution is dispensed into amber vials at a temperature of +5° C. to 10° C., (optimally at +5° C.); the solution is frozen at a freezing temperature of −35° C. to −50° C., (optimally at −45° C.); the frozen solution is subjected to an initial freeze drying step at a primary drying pressure of 20 to 80 microns, (optimally at 60 microns); the freeze-dried product is held at a shelf temperature at −10° C. to −40° C., (optimally at −30° C.), for 24 to 72 hours, (optimally for 60 hours); and finally the freeze-dried product is subjected to a secondary drying step at a drying pressure of 20-80 microns, (optimally at 60 microns) at a shelf temperature of +10° C. to +35° C., (optimally +25° C.), for 15 to 30 hours (optimally for 24 hours). A pressure rise test is used to determine the end of primary drying. At the conclusion of the lyophilization cycle, the vials are back-filled with nitrogen and stoppered.

Table 11 sets out the differences in the formulation used for CMC-544 and the formulation used for CMC-676. Significant differences between the CMA-676 formulation and the formulation used for CMC-544 include reduced protein concentration in the new formulation (0.5 mg/mL), the use of tromethamine as a buffer and the presence of 0.01% TWEEN® 80. This results in the reconstituted CMC-544 in the new formulation being clear as opposed to the turbidity seen in the reconstituted CMA-676 formulation (see Tables 12 and 13).

TABLE 11

COMPARISON OF THE CMA-676 FORMULATION AND CMC-544 FORMULATION FOR CMC-544

| | CMA-676 Formulation | CMC-544 Formulation |
|---|---|---|
| Protein Concentration | 1.0 mg/mL | 0.5 mg/mL |
| Formulation | 1.5% sucrose, 0.9% Dextran 40, 100 mM sodium chloride, 5 mM phosphate buffer | 1.5% sucrose, 0.9% Dextran 40, 0.01% TWEEN® 80, 0.01% polysorbate 80, 50 mM sodium chloride, 20 mM tromethamine |

TABLE 12

STABILITY AND PHYSICO-CHEMICAL OBSERVATIONS OF THE CMA-676 AND CMC-544 FORMULATION LYOPHILIZED AND STORED AT 5° C.

| | CMA-676 FORMULATION | | CMC-544 FORMULATION | |
|---|---|---|---|---|
| Time | Initial | 4 weeks | Initial | 4 weeks |
| Physical Observation of Reconstituted Conjugates | Slightly turbid | Slightly turbid | Clear | Clear |
| pH | 7.5 | 7.5 | 7.8 | 7.8 |
| Total Protein (mg/mL) | 1.07 | 1.07 | 0.52 | 0.52 |
| Total Calicheamicin (μg/mg of protein) | 67 | 67 | 57 | 57 |
| Unconjugated Calicheamicin (μg/mg of protein) | 1.21 | 2.82 | 0.97 | 1.13 |
| % Aggregates | 3.03 | 2.81 | 1.59 | 1.70 |

TABLE 13

STABILITY AND PHYSICO-CHEMICAL OBSERVATIONS OF THE CMA-676 AND CMC-544 FORMULATION LYOPHILIZED AND STORED AT 25° C.

| | CMA-676 FORMULATION | | CMC-544 FORMULATION | |
|---|---|---|---|---|
| Time | Initial | 4 weeks | Initial | 4 weeks |
| Physical Observation of Reconstituted Conjugates | Slightly turbid | Slightly turbid | Clear | Clear |
| pH | 7.5 | 7.5 | 7.8 | 7.8 |
| Total Protein (mg/mL) | 1.03 | 1.03 | 0.51 | 0.51 |
| Total Calicheamicin (μg/mg of protein) | 67 | 67 | 57 | 57 |
| Unconjugated Calicheamicin (μg/mg of protein) | 1.13 | 1.03 | 1.03 | 0.94 |
| % Aggregates | 2.63 | 2.96 | 1.49 | 2.09 |

All references and patents cited above are incorporated herein by reference. Numerous modifications and variations of the present inventions are included in the above-identified specification and are expected to be obvious to one of skill in the art. Such modifications and alterations to the conjugation process, the conjugates made by the process, and to the compositions/formulations comprising conjugates are believed to be encompassed within the scope of the claims.

BIBLIOGRAPHY

1. G. Kohler and Milstein, C., Nature, 256:495 (1975).
2. T. G. Hose and Blair, A. H., CRC Critical Rev. Drug Carrier Systems, 3:263 (1987).
3. U.S. Pat. No. 5,877,296

4. U.S. Pat. No. 5,773,001
5. U.S. Pat. No. 5,714,586
6. U.S. Pat. No. 5,712,374
7. U.S. Pat. No. 5,053,394
8. J. Tramontano, et al., J. Mol. Recognit., 7:9 (1994).
9. H. McConnell and Hoess, J., J. Mol. Biol., 250:460 (1995).
10. Nord et al., Nat. Biotechnol., 15:772 (1997).
11. Nord et al., Protein Eng., 8:601 (1995).
12. Ku and Schultz, Proc. Natl. Acad. Sci., USA 92:6552 (1995).
13. Markand et al., Biochemistry, 35:8045 (1996).
14. Markand et al., Biochemistry, 35:8098 (1996).
15. Rottgen and Collins, Gene, 164:243 (1995).
16. Wang et al, J. Biol. Chem., 270:12250 (1995).
17. I. D. Bernstein et al., J. Clin. Invest., 79:1153 (1987).
18. I. D. Bernstein et al., J. Immunol., 128:867-881 (1992).
19. Kabat et al., Sequencing of Proteins of Immunological Interest, 1:310-334 (1994).
20. PCT Publication No. WO 91/09967.
21. Yang et al., J. Mol. Biol., 254:392-403 (1995).
22. Low et al., J. Mol. Biol., 260:359-368 (1996).
23. Patten et al., Curr. Opin. Biotechnol., 8:724-733 (1997).
24. Thompson et al., J. Mol. Biol., 256:77-88 (1996).
25. Crameri et al., Nature, 391:288-291 (1998).
26. U.S. Pat. No. 4,671,958
27. U.S. Pat. No. 4,970,198
28. U.S. Pat. No. 5,037,651
29. U.S. Pat. No. 5,079,233
30. U.S. Pat. No. 5,877,296
31. PCT Publication No. WO 98/20734
32. Trail P and Bianchi A., Current Opin. Immunol., 11:584-588 (1999).
33. Dubowchik G. and Walker M., Pharmacol. & Therapeutics, 83:67-123 (1999).
34. Bross P. F., Beitz J., Chen G., Chen X. H., Duffy E., Keiffer-Bross P., Beitz J., Chen G., Chen X., Duffy E., Kieffer L., Roy S., Sridhara R., Rahman A., Williams G., Pazdur R., Clin. Cancer Res., 7:1490-1496 (2001).
35. Berger M., Leopold L., Dowell J., Korth-Bradley J., Sherman M., Invest. New Drugs; 20: 395-406 (2002).
36. Sievers E., Larson R., Stadmauer E., Estey E., Lowenberg B., Dombret H., Karanes C., Theobald M., Bennet J., Sherman M., et al., J. Clin. Oncol., 19:3244-3254 (2001).
37. Larson R., Boogaerts M., Estey E., Karanes C., Stadtmauer E., Sievers E., Mineur P., Bennett J., Berger M., Eten C. et al. Leukemia, 16:1627-1636 (2002).
38. Hamann P., Hinman L., Beyer C., Kindh D., Upeslacis J., Flowers D., Bernstein I., Choice of Linker. Bioconj. Chem., 13:40-46 (2002).
39. Hamann P., Hinman L., Hollander I., Beyer C., Lindh D., Holcomb R., Hallet W., Tsou H., Upeslacis J., Shochat D., et al., Bioconj. Chem., 13:47-58 (2002).
40. Lee M., Dunne T., Chang C., Siegal M., Morton G., Ellestad G., McGahren W., Borders D., J. Am. Chem. Soc., 114:985-987 (1992).
41. Zein N., Sinha A., McGahren W., Ellestad G., Science, 240:1198-1201 (1988).
42. Thorson J., Sievers E., Ahlert J., Shepard E., Whitwam R., Onwueme K., Ruppen M., Current Pharmaceut. Design, 6:1841-1879 (2000).
43. Andrews R., Singer J., Bernstein I., J. Exp. Med., 169: 1721-1731 (1989).
44. Kreitman R. J., Current Pharmaceut. Biotech., 2:313-325 (2001).
45. Pastan I., Kreitman R. J., Current Opin. Investig. Drugs, 3(7):1089-1091 (2002).
46. Kreitman R. J., Curr. Opin. Mol. Ther., 5:44-551 (2003).
47. Crocker P. R. and Varki A. Siglecs, Trends in Immunol., 22:337-342 (2001).
48. Hursey M., Newton D. L., Hansen H. J., Ruby D., Goldenberg D. M., Rybak S. M., Leukemia and Lymphoma, 43:953-959 (2002).
49. Nitschke L., Floyd H., and Crocker P. R., Scand. J. Immunol., 53:227-234 (2001).
50. Moyron-Quiroz J. E., Partida-Sanchez S., Donis-Hernandez R., Sandoval-Montes C. and Santos-Argumedo L., Scand. J. Immunol., 55:343-351 (2002).
51. Tedder T. F., Tuscano J., Sato S., Kehrl J. H., Ann. Rev. Immunol., 15:481-504 (1997).
52. Hanna R., Ong G. L., Mattes M. J., Cancer Res., 56:3062-3068 (1996).
53. Shan D. and Press O. W., J. Immunol., 154:4466-4475 (1995).
54. Dowell J. A., Korth-Bradley J., Liu H., King S. P., Berger M. S., J. Clin. Pharmacol., 41:1206-1214 (2001).
55. Gibaldi M., Perrier D., Pharmacokinetics, 2nd ed., Marcel-Dekker Inc., NY (1982).
56. Van Horssen P. J., Preijers, F. W., Van Oosterhout, Y. V., Eling W. M. and De Witte, T., Leukemia & Lymphoma, 39(5-6):591-599 (2000).
57. Hinman L. M., Hamann P. R., Wallace R., Menendez A. T., Dun F. E., Upeslacis J., Cancer Res., 53:3336-3342 (1993).
58. Kreitman R. J., Wilson W. H., Bergeron K., Raggio M., Stetler-Stevenson M., Fitzgerald D. J., Pastan, Engl. J. Med., 345:241-247 (2001).
59. Leonard J. P. and Link B. K., Sem. Oncol., 29:81-86 (2002).
60. Schindler J., Sausville E., Messmann R., Uhr J. W. & Vitetta, E. S., Clin. Cancer Res., 7:255-258 (2001).
61. Vincent T. DeVita, Samuelo Hellman, Steven A. Rosenberg, Eds., Cancer Principles and Practice of Oncology, 6th Edition, Publishers: Lippincott, Williams and Wilkins (2001).
62. Edward Chu and Vincent T. DeVita, Physician's Cancer Chemotherapy Drug Manual, Publishers: Jones and Bartlett (2002).

SEQUENCE LISTING

<160> NUMBER OF SEQ ID NOS: 65

<210> SEQ ID NO 1
<211> LENGTH: 5
<212> TYPE: PRT
<213> ORGANISM: Mus musculus
<220> FEATURE:
<223> OTHER INFORMATION: mouse monoclonal 5/44 CDR-H1

<400> SEQUENCE: 1

-continued

```
Asn Tyr Trp Ile His
1               5

<210> SEQ ID NO 2
<211> LENGTH: 16
<212> TYPE: PRT
<213> ORGANISM: Mus musculus
<220> FEATURE:
<223> OTHER INFORMATION: mouse monoclonal 5/44 CDR-H2gL1 T3

<400> SEQUENCE: 2

Gly Ile Asn Pro Gly Asn Asn Tyr Thr Thr Tyr Lys Arg Asn Leu Lys
1               5                   10                  15

<210> SEQ ID NO 3
<211> LENGTH: 12
<212> TYPE: PRT
<213> ORGANISM: Mus musculus
<220> FEATURE:
<223> OTHER INFORMATION: mouse monoclonal 5/44 CDR-H3

<400> SEQUENCE: 3

Glu Gly Tyr Gly Asn Tyr Gly Ala Trp Phe Ala Tyr
1               5                   10

<210> SEQ ID NO 4
<211> LENGTH: 15
<212> TYPE: PRT
<213> ORGANISM: Mus musculus
<220> FEATURE:
<223> OTHER INFORMATION: mouse monoclonal 5/44 CDR-L1

<400> SEQUENCE: 4

Arg Ser Ser Gln Ser Leu Ala Asn Ser Tyr Gly Asn Thr Phe Leu
1               5                   10                  15

<210> SEQ ID NO 5
<211> LENGTH: 7
<212> TYPE: PRT
<213> ORGANISM: Mus musculus
<220> FEATURE:
<223> OTHER INFORMATION: mouse monoclonal 5/44 CDR-L2

<400> SEQUENCE: 5

Gly Ile Ser Asn Arg Phe Ser
1               5

<210> SEQ ID NO 6
<211> LENGTH: 9
<212> TYPE: PRT
<213> ORGANISM: Mus musculus
<220> FEATURE:
<223> OTHER INFORMATION: mouse monoclonal 5/44 CDR-L3

<400> SEQUENCE: 6

Leu Gln Gly Thr His Gln Pro Tyr Thr
1               5

<210> SEQ ID NO 7
<211> LENGTH: 113
<212> TYPE: PRT
<213> ORGANISM: Mus musculus
<220> FEATURE:
<223> OTHER INFORMATION: mouse monoclonal 5/44 VL domain

<400> SEQUENCE: 7
```

Asp Val Val Val Thr Gln Thr Pro Leu Ser Leu Pro Val Ser Phe Gly
1               5                   10                  15

Asp Gln Val Ser Ile Ser Cys Arg Ser Ser Gln Ser Leu Ala Asn Ser
            20                  25                  30

Tyr Gly Asn Thr Phe Leu Ser Trp Tyr Leu His Lys Pro Gly Gln Ser
        35                  40                  45

Pro Gln Leu Leu Ile Tyr Gly Ile Ser Asn Arg Phe Ser Gly Val Pro
    50                  55                  60

Asp Arg Phe Thr Gly Ser Gly Ser Gly Thr Asp Phe Thr Leu Lys Ile
65                  70                  75                  80

Ser Thr Ile Lys Pro Glu Asp Leu Gly Met Tyr Tyr Cys Leu Gln Gly
                85                  90                  95

Thr His Gln Pro Tyr Thr Phe Gly Gly Gly Thr Lys Leu Glu Ile Lys
            100                 105                 110

Arg

<210> SEQ ID NO 8
<211> LENGTH: 121
<212> TYPE: PRT
<213> ORGANISM: Mus musculus
<220> FEATURE:
<223> OTHER INFORMATION: mouse monoclonal 5/44 VH domain

<400> SEQUENCE: 8

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Arg Phe Thr Asn Tyr
            20                  25                  30

Trp Ile His Trp Val Lys Gln Arg Pro Gly Gln Gly Leu Glu Trp Ile
        35                  40                  45

Gly Gly Ile Asn Pro Gly Asn Asn Tyr Thr Thr Tyr Lys Arg Asn Leu
    50                  55                  60

Lys Gly Lys Ala Thr Leu Thr Ala Val Thr Ser Ala Ser Thr Ala Tyr
65                  70                  75                  80

Met Asp Leu Ser Ser Leu Thr Ser Glu Asp Ser Ala Val Tyr Tyr Cys
                85                  90                  95

Thr Arg Glu Gly Tyr Gly Asn Tyr Gly Ala Trp Phe Ala Tyr Trp Gly
            100                 105                 110

Gln Gly Thr Leu Val Thr Val Ser Ser
        115                 120

<210> SEQ ID NO 9
<211> LENGTH: 13
<212> TYPE: PRT
<213> ORGANISM: Artificial Sequence
<220> FEATURE:
<223> OTHER INFORMATION: cH

<400> SEQUENCE: 9

Gly Asn Asn Tyr Thr Thr Tyr Lys Arg Asn Leu Lys Gly
1               5                   10

<210> SEQ ID NO 10
<211> LENGTH: 13
<212> TYPE: PRT
<213> ORGANISM: Artificial Sequence
<220> FEATURE:
<223> OTHER INFORMATION: N55Q

<400> SEQUENCE: 10

```
Gly Asn Gln Tyr Thr Thr Tyr Lys Arg Asn Leu Lys Gly
1               5                   10

<210> SEQ ID NO 11
<211> LENGTH: 13
<212> TYPE: PRT
<213> ORGANISM: Artificial Sequence
<220> FEATURE:
<223> OTHER INFORMATION: T57A

<400> SEQUENCE: 11

Gly Asn Asn Tyr Ala Thr Tyr Lys Arg Asn Leu Lys Gly
1               5                   10

<210> SEQ ID NO 12
<211> LENGTH: 13
<212> TYPE: PRT
<213> ORGANISM: Artificial Sequence
<220> FEATURE:
<223> OTHER INFORMATION: T57V

<400> SEQUENCE: 12

Gly Asn Asn Tyr Val Thr Tyr Lys Arg Asn Leu Lys Gly
1               5                   10

<210> SEQ ID NO 13
<211> LENGTH: 17
<212> TYPE: PRT
<213> ORGANISM: Artificial Sequence
<220> FEATURE:
<223> OTHER INFORMATION: CDR-H2 (T57)A H'

<400> SEQUENCE: 13

Gly Ile Asn Pro Gly Asn Asn Tyr Ala Thr Tyr Lys Arg Asn Leu Lys
1               5                   10                  15

Gly

<210> SEQ ID NO 14
<211> LENGTH: 13
<212> TYPE: PRT
<213> ORGANISM: Artificial Sequence
<220> FEATURE:
<223> OTHER INFORMATION: K60R

<400> SEQUENCE: 14

Gly Asn Asn Tyr Thr Thr Tyr Arg Arg Asn Leu Lys Gly
1               5                   10

<210> SEQ ID NO 15
<211> LENGTH: 17
<212> TYPE: PRT
<213> ORGANISM: Artificial Sequence
<220> FEATURE:
<223> OTHER INFORMATION: CDR-H2 (K60R)R H''

<400> SEQUENCE: 15

Gly Ile Asn Pro Gly Asn Asn Tyr Thr Thr Tyr Arg Arg Asn Leu Lys
1               5                   10                  15

Gly

<210> SEQ ID NO 16
<211> LENGTH: 17
<212> TYPE: PRT
<213> ORGANISM: Artificial Sequence
<220> FEATURE:
```

<223> OTHER INFORMATION: CDR-H2 (T57A K60R) H'''

<400> SEQUENCE: 16

Gly Ile Asn Pro Gly Asn Asn Tyr Ala Thr Tyr Arg Arg Asn Leu Lys
1               5                   10                  15
Gly

<210> SEQ ID NO 17
<211> LENGTH: 70
<212> TYPE: PRT
<213> ORGANISM: Homo sapiens
<220> FEATURE:
<223> OTHER INFORMATION: DKP9

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Gly
        35                  40                  45

Ser Gly Thr Asp Phe Thr Leu Thr Ile Ser Ser Leu Gln Pro Glu Asp
    50                  55                  60

Phe Ala Thr Tyr Tyr Cys
65                  70

<210> SEQ ID NO 18
<211> LENGTH: 11
<212> TYPE: PRT
<213> ORGANISM: Homo sapiens
<220> FEATURE:
<223> OTHER INFORMATION: JK1

<400> SEQUENCE: 18

Phe Gly Gln Gly Thr Lys Val Glu Ile Lys Arg
1               5                   10

<210> SEQ ID NO 19
<211> LENGTH: 113
<212> TYPE: PRT
<213> ORGANISM: Artificial Sequence
<220> FEATURE:
<223> OTHER INFORMATION: gL1

<400> SEQUENCE: 19

Asp Val Gln Val Thr Gln Ser Pro Ser Ser Leu Ser Ala Ser Val Gly
1               5                   10                  15

Asp Arg Val Thr Ile Thr Cys Arg Ser Ser Gln Ser Leu Ala Asn Ser
            20                  25                  30

Tyr Gly Asn Thr Phe Leu Ser Trp Tyr Leu His Lys Pro Gly Lys Ala
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Leu Gln Gly
                85                  90                  95

Thr His Gln Pro Tyr Thr Phe Gly Gln Gly Thr Lys Val Glu Ile Lys
            100                 105                 110

Arg

<210> SEQ ID NO 20
<211> LENGTH: 113
<212> TYPE: PRT
<213> ORGANISM: Artificial Sequence
<220> FEATURE:
<223> OTHER INFORMATION: gL2

<400> SEQUENCE: 20

Asp Val Val Thr Gln Ser Pro Ser Ser Leu Ser Ala Ser Val Gly
1               5                   10                  15

Asp Arg Val Thr Ile Thr Cys Arg Ser Gln Ser Leu Ala Asn Ser
            20                  25                  30

Tyr Gly Asn Thr Phe Leu Ser Trp Tyr Leu His Lys Pro Gly Lys Ala
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Leu Gln Gly
                85                  90                  95

Thr His Gln Pro Tyr Thr Phe Gly Gln Gly Thr Lys Val Glu Ile Lys
                100                 105                 110

Arg

<210> SEQ ID NO 21
<211> LENGTH: 80
<212> TYPE: PRT
<213> ORGANISM: Homo sapiens
<220> FEATURE:
<223> OTHER INFORMATION: DP7

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Trp Val
            20                  25                  30

Arg Gln Ala Pro Gly Gln Gly Leu Glu Trp Met Gly Lys Phe Gln Gly
        35                  40                  45

Arg Val Thr Met Thr Arg Asp Thr Ser Thr Ser Thr Val Tyr Met Glu
    50                  55                  60

Leu Ser Ser Leu Arg Ser Glu Asp Thr Ala Val Tyr Tyr Cys Ala Arg
65                  70                  75                  80

<210> SEQ ID NO 22
<211> LENGTH: 11
<212> TYPE: PRT
<213> ORGANISM: Homo sapiens
<220> FEATURE:
<223> OTHER INFORMATION: JH4

<400> SEQUENCE: 22

Trp Gly Gln Gly Thr Leu Val Thr Val Ser Ser
1               5                   10

<210> SEQ ID NO 23
<211> LENGTH: 121
<212> TYPE: PRT
<213> ORGANISM: Artificial Sequence
<220> FEATURE:
<223> OTHER INFORMATION: gH1

-continued

<400> SEQUENCE: 23

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asn Tyr
            20                  25                  30

Trp Ile His Trp Val Arg Gln Ala Pro Gly Gln Gly Leu Glu Trp Ile
        35                  40                  45

Gly Gly Ile Asn Pro Gly Asn Gln Tyr Thr Thr Tyr Lys Arg Asn Leu
    50                  55                  60

Lys Gly Arg Ala Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Glu Gly Tyr Gly Asn Tyr Gly Ala Trp Phe Ala Tyr Trp Gly
            100                 105                 110

Gln Gly Thr Leu Val Thr Val Ser Ser
        115                 120

<210> SEQ ID NO 24
<211> LENGTH: 121
<212> TYPE: PRT
<213> ORGANISM: Artificial Sequence
<220> FEATURE:
<223> OTHER INFORMATION: gH4

<400> SEQUENCE: 24

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asn Tyr
            20                  25                  30

Trp Ile His Trp Val Arg Gln Ala Pro Gly Gln Gly Leu Glu Trp Ile
        35                  40                  45

Gly Gly Ile Asn Pro Gly Asn Asn Tyr Ala Thr Tyr Arg Arg Asn Leu
    50                  55                  60

Lys Gly Arg Ala Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Glu Gly Tyr Gly Asn Tyr Gly Ala Trp Phe Ala Tyr Trp Gly
            100                 105                 110

Gln Gly Thr Leu Val Thr Val Ser Ser
        115                 120

<210> SEQ ID NO 25
<211> LENGTH: 121
<212> TYPE: PRT
<213> ORGANISM: Artificial Sequence
<220> FEATURE:
<223> OTHER INFORMATION: gH5

<400> SEQUENCE: 25

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Asn Tyr
            20                  25                  30

Trp Ile His Trp Val Arg Gln Ala Pro Gly Gln Gly Leu Glu Trp Ile
        35                  40                  45

```
Gly Gly Ile Asn Pro Gly Asn Asn Tyr Ala Thr Tyr Arg Arg Asn Leu
        50                  55                  60

Lys Gly Arg Val Thr Met Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Thr Arg Glu Gly Tyr Gly Asn Tyr Gly Ala Trp Phe Ala Tyr Trp Gly
            100                 105                 110

Gln Gly Thr Leu Val Thr Val Ser Ser
            115                 120
```

<210> SEQ ID NO 26
<211> LENGTH: 121
<212> TYPE: PRT
<213> ORGANISM: Artificial Sequence
<220> FEATURE:
<223> OTHER INFORMATION: gH6

<400> SEQUENCE: 26

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Arg Phe Thr Asn Tyr
                20                  25                  30

Trp Ile His Trp Val Arg Gln Ala Pro Gly Gln Gly Leu Glu Trp Ile
            35                  40                  45

Gly Gly Ile Asn Pro Gly Asn Asn Tyr Ala Thr Tyr Arg Arg Lys Phe
        50                  55                  60

Gln Gly Arg Ala Thr Leu Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Thr Arg Glu Gly Tyr Gly Asn Tyr Gly Ala Trp Phe Ala Tyr Trp Gly
            100                 105                 110

Gln Gly Thr Leu Val Thr Val Ser Ser
            115                 120
```

<210> SEQ ID NO 27
<211> LENGTH: 121
<212> TYPE: PRT
<213> ORGANISM: Artificial Sequence
<220> FEATURE:
<223> OTHER INFORMATION: gH7

<400> SEQUENCE: 27

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Arg Phe Thr Asn Tyr
                20                  25                  30

Trp Ile His Trp Val Arg Gln Ala Pro Gly Gln Gly Leu Glu Trp Ile
            35                  40                  45

Gly Gly Ile Asn Pro Gly Asn Asn Tyr Ala Thr Tyr Arg Arg Lys Phe
        50                  55                  60

Gln Gly Arg Val Thr Met Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Thr Arg Glu Gly Tyr Gly Asn Tyr Gly Ala Trp Phe Ala Tyr Trp Gly
```

```
                      100                 105                 110
Gln Gly Thr Leu Val Thr Val Ser Ser
        115                 120

<210> SEQ ID NO 28
<211> LENGTH: 239
<212> TYPE: PRT
<213> ORGANISM: Artificial Sequence
<220> FEATURE:
<223> OTHER INFORMATION: Full sequence of g5/44 light chain

<400> SEQUENCE: 28

Met Lys Leu Pro Val Arg Leu Leu Val Leu Leu Leu Phe Trp Ile Pro
1               5                   10                  15

Ala Ser Arg Gly Asp Val Gln Val Thr Gln Ser Pro Ser Ser Leu Ser
            20                  25                  30

Ala Ser Val Gly Asp Arg Val Thr Ile Thr Cys Arg Ser Ser Gln Ser
        35                  40                  45

Leu Ala Asn Ser Tyr Gly Asn Thr Phe Leu Ser Trp Tyr Leu His Lys
    50                  55                  60

Pro Gly Lys Ala Pro Gln Leu Leu Ile Tyr Gly Ile Ser Asn Arg Phe
65                  70                  75                  80

Ser Gly Val Pro Asp Arg Phe Ser Gly Ser Gly Ser Gly Thr Asp Phe
                85                  90                  95

Thr Leu Thr Ile Ser Ser Leu Gln Pro Glu Asp Phe Ala Thr Tyr Tyr
            100                 105                 110

Cys Leu Gln Gly Thr His Gln Pro Tyr Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 29
<211> LENGTH: 781
<212> TYPE: DNA
<213> ORGANISM: Artificial Sequence
<220> FEATURE:
<223> OTHER INFORMATION: DNA coding strand for g5/44 light chain

<400> SEQUENCE: 29
ttcgaagccg ccaccatgaa gttgcctgtt aggctgttgg tgcttctgtt gttctggatt      60
cctgcttccc ggggtgacgt tcaagtgacc cagagcccat ccagcctgag cgcatctgta     120
ggagaccggg tcaccatcac ttgtagatcc agtcagagtc ttgcaaacag ttatgggaac     180 accttttgt cttggtatct gcacaaacca ggtaaagccc cacaattgct catctacgga     240
atctctaaca gatttagtgg tgtaccagac aggttcagcg gttccggaag tggtactgat     300
```

-continued

```
ttcaccctca cgatctcgtc tctccagcca gaagatttcg ccacttatta ctgtttacaa    360
ggtacacatc agccgtacac attcggtcag ggtactaaag tagaaatcaa acgtacggta    420
gcggccccat ctgtcttcat cttcccgcca tctgatgagc agttgaaatc tggaactgcc    480
tctgttgtgt gcctgctgaa taacttctat cccagagagg ccaaagtaca gtggaaggtg    540
gataacgccc tccaatcggg taactcccag gagagtgtca cagagcagga cagcaaggac    600
agcacctaca gcctcagcag caccctgacg ctgagcaaag cagactacga gaaacacaaa    660
gtctacgcct gcgaagtcac ccatcagggc ctgagctcgc ccgtcacaaa gagcttcaac    720 agggagagt gttagaggga gaagtgcccc cacctgctcc tcagttccag cctgggaatt    780
c                                                                    781
```

<210> SEQ ID NO 30
<211> LENGTH: 467
<212> TYPE: PRT
<213> ORGANISM: Artificial Sequence
<220> FEATURE:
<223> OTHER INFORMATION: Full sequence of g5/44 heavy chain

<400> SEQUENCE: 30

```
Met Asp Phe Gly Phe Ser Leu Val Phe Leu Ala Leu Ile Leu Lys Gly
1               5                   10                  15

Val Gln Cys Glu Val Gln Leu Val Gln Ser Gly Ala Glu Val Lys Lys
            20                  25                  30

Pro Gly Ala Ser Val Lys Val Ser Cys Lys Ala Ser Gly Tyr Arg Phe
        35                  40                  45

Thr Asn Tyr Trp Ile His Trp Val Arg Gln Ala Pro Gly Gln Gly Leu
    50                  55                  60

Glu Trp Ile Gly Gly Ile Asn Pro Gly Asn Asn Tyr Ala Thr Tyr Arg
65                  70                  75                  80

Arg Lys Phe Gln Gly Arg Val Thr Met Thr Ala Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Thr Arg Glu Gly Tyr Gly Asn Tyr Gly Ala Trp Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270
```

```
Ile Ser Arg Thr Pro Glu Val Thr Cys Val Val Val Asp Val Ser Gln
            275                 280                 285
Glu Asp Pro Glu Val Gln Phe Asn Trp Tyr Val Asp Gly Val Glu Val
290                 295                 300
His Asn Ala Lys Thr Lys Pro Arg Glu Glu Gln Phe Asn Ser Thr Tyr
305                 310                 315                 320
Arg Val Val Ser Val Leu Thr Val Leu His Gln Asp Trp Leu Asn Gly
            325                 330                 335
Lys Glu Tyr Lys Cys Lys Val Ser Asn Lys Gly Leu Pro Ser Ser Ile
            340                 345                 350
Glu Lys Thr Ile Ser Lys Ala Lys Gly Gln Pro Arg Glu Pro Gln Val
            355                 360                 365
Tyr Thr Leu Pro Pro Ser Gln Glu Glu Met Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
            405                 410                 415
Val Leu Asp Ser Asp Gly Ser Phe Phe Leu Tyr Ser Arg Leu Thr Val
            420                 425                 430
Asp Lys Ser Arg Trp Gln Glu Gly Asn Val Phe Ser Cys Ser Val Met
            435                 440                 445
His Glu Ala Leu His Asn His Tyr Thr Gln Lys Ser Leu Ser Leu Ser
    450                 455                 460
Leu Gly Lys
465

<210> SEQ ID NO 31
<211> LENGTH: 2160
<212> TYPE: DNA
<213> ORGANISM: Artificial Sequence
<220> FEATURE:
<223> OTHER INFORMATION: DNA coding strand for g5/44 heavy chain

<400> SEQUENCE: 31
aagcttgccg ccaccatgga cttcggattc tctctcgtgt tcctggcact cattctcaag    60
ggagtgcagt gtgaggtgca attggtccag tcaggagcag aggttaagaa gcctggtgct   120
tccgtcaaag tttcgtgtaa ggctagcggc tacaggttca caaattattg gattcattgg   180
gtcaggcagg ctccgggaca aggcctggaa tggatcggtg cattaatccc gggaataac   240 tacgctacat ataggagaaa attccagggc agagttacga tgaccgcgga cacctccaca   300
agcactgtct acatggagct gtcatctctg gatccgagg acaccgcagt gtactattgt   360
actagagaag gctacggtaa ttacggagcc tggttcgcct actggggcca gggtaccta   420 gtcacagtct cctcagcttc tacaaagggc ccatccgtct tccccctggc gccctgctcc   480
aggagcacct ccgagagcac agccgccctg ggctgcctgg tcaaggacta cttcccgaa   540 ccggtgacgg tgtcgtggaa ctcaggcgcc ctgaccagcg gcgtgcacac cttcccggct   600
gtcctacagt cctcaggact ctactccctc agcagcgtgg tgaccgtgcc ctccagcagc   660
ttgggcacga agacctacac ctgcaacgta gatcacaagc ccagcaacac caaggtggac   720
aagagagttg gtgagaggcc agcacaggga gggaggtgt ctgctggaag ccaggctcag   780
ccctcctgcc tggacgcacc ccggctgtgc agccccagcc cagggcagca aggcatgccc   840
catctgtctc ctcacccgga ggcctctgac cacccccactc atgcccaggg agagggtctt   900
```

```
ctggattttt  ccaccaggct  ccgggcagcc  acaggctgga  tgccctacc   ccaggccctg    960 cgcatacagg  ggcaggtgct  gcgctcagac  ctgccaagag  ccatatccgg  gaggaccctg   1020
cccctgacct  aagcccaccc  caaaggccaa  actctccact  ccctcagctc  agacaccttc   1080
tctcctccca  gatctgagta  actcccaatc  ttctctctgc  agagtccaaa  tatggtcccc   1140
catgcccacc  atgcccaggt  aagccaaccc  aggcctcgcc  ctccagctca  aggcgggaca   1200
ggtgccctag  agtagcctgc  atccaggac   aggcccagc   cgggtgctga  cgcatccacc   1260
tccatctctt  cctcagcacc  tgagttcctg  ggggaccat   cagtcttcct  gttccccca    1320 aaacccaagg  acactctcat  gatctcccgg  accctgagg   tcacgtgcgt  ggtggtggac   1380
gtgagccagg  aagaccccga  ggtccagttc  aactggtacg  tggatggcgt  ggaggtgcat   1440
aatgccaaga  caaagccgcg  ggaggagcag  ttcaacagca  cgtaccgtgt  ggtcagcgtc   1500
ctcaccgtcc  tgcaccagga  ctggctgaac  ggcaaggagt  acaagtgcaa  ggtctccaac   1560
aaaggcctcc  cgtcctccat  cgagaaaacc  atctccaaag  ccaaaggtgg  acccacgggg   1620
gtgcgagggc  cacatggaca  gaggtcagct  cggcccaccc  tctgccctgg  gagtgaccgc   1680
tgtgccaacc  tctgtcccta  cagggcagcc  ccgagagcca  caggtgtaca  ccctgccccc   1740
atcccaggag  gagatgacca  agaaccaggt  cagcctgacc  tgcctggtca  aaggcttcta   1800
ccccagcgac  atcgccgtgg  agtgggagag  caatgggcag  ccggagaaca  actacaagac   1860
cacgcctccc  gtgctggact  ccgacggctc  cttcttcctc  tacagcaggc  taaccgtgga   1920
caagagcagg  tggcaggagg  ggaatgtctt  ctcatgctcc  gtgatgcatg  aggctctgca   1980
caaccactac  acacagaaga  gcctctccct  gtctctgggt  aaatgagtgc  cagggccggc   2040
aagcccccgc  tccccgggct  ctcggggtcg  cgcgaggatg  cttggcacgt  accccgtcta   2100
catacttccc  aggcacccag  catggaaata  aagcacccac  cactgccctg  gctcgaattc   2160
```

<210> SEQ ID NO 32
<211> LENGTH: 94
<212> TYPE: DNA
<213> ORGANISM: Artificial Sequence
<220> FEATURE:
<223> OTHER INFORMATION: 5/44gH1 T1

<400> SEQUENCE: 32

```
agtgtgaggt  gcaattggtc  cagtcaggag  cagaggttaa  gaagcctggt  gcttccgtca    60
aagtttcgtg  taaggctagc  ggctacaggt  tcac                                  94
```

<210> SEQ ID NO 33
<211> LENGTH: 96
<212> TYPE: DNA
<213> ORGANISM: Artificial Sequence
<220> FEATURE:
<223> OTHER INFORMATION: 5/44gH1 T2

<400> SEQUENCE: 33

```
gtggcattaa  tcccgggaat  cagtacacta  catataaaag  aaatctaaag  ggcagagcaa    60
cgctgaccgc  ggacacctcc  acaagcactg  tctaca                                96
```

<210> SEQ ID NO 34
<211> LENGTH: 95
<212> TYPE: DNA
<213> ORGANISM: Artificial Sequence
<220> FEATURE:
<223> OTHER INFORMATION: 5/44gH1 T3

<400> SEQUENCE: 34
agagaaggct acgtaatta cggagcctgg ttcgcctact ggggccaggg taccctagtc    60
acagtctcct cagcttctac aaagggccca agaaa    95

<210> SEQ ID NO 35
<211> LENGTH: 94
<212> TYPE: DNA
<213> ORGANISM: Artificial Sequence
<220> FEATURE:
<223> OTHER INFORMATION: 5/44gH1 B1

<400> SEQUENCE: 35
ggaccaattg cacctcacac tgcactccct tgagaatgag tgccaggaac acgagagaga    60
atccgaagtc catggtggcg gcaagctttt attc    94

<210> SEQ ID NO 36
<211> LENGTH: 97
<212> TYPE: DNA
<213> ORGANISM: Artificial Sequence
<220> FEATURE:
<223> OTHER INFORMATION: 5/44gH1 B2

<400> SEQUENCE: 36
gattcccggg attaatgcca ccgatccatt ccaggccttg tcccggagcc tgcctgaccc    60
aatgaatcca ataatttgtg aacctgtagc cgctagc    97

<210> SEQ ID NO 37
<211> LENGTH: 93
<212> TYPE: DNA
<213> ORGANISM: Artificial Sequence
<220> FEATURE:
<223> OTHER INFORMATION: 5/44gH1 B3

<400> SEQUENCE: 37
cgtaattacc gtagccttct ctagtacaat agtacactgc ggtgtcctcg gatctcagag    60
atgacagctc catgtagaca gtgcttgtgg agg    93

<210> SEQ ID NO 38
<211> LENGTH: 21
<212> TYPE: DNA
<213> ORGANISM: Artificial Sequence
<220> FEATURE:
<223> OTHER INFORMATION: 5/44gH1 F1

<400> SEQUENCE: 38
gaataaaagc ttgccgccac c    21

<210> SEQ ID NO 39
<211> LENGTH: 22
<212> TYPE: DNA
<213> ORGANISM: Artificial Sequence
<220> FEATURE:
<223> OTHER INFORMATION: 5/44gH1 R1

<400> SEQUENCE: 39
tttcttgggc cctttgtaga ag    22

<210> SEQ ID NO 40
<211> LENGTH: 87
<212> TYPE: DNA
<213> ORGANISM: Artificial Sequence
<220> FEATURE:
<223> OTHER INFORMATION: 5/44gL1 T1

<400> SEQUENCE: 40
gcttcccggg gtgacgttca agtgacccag agcccatcca gcctgagcgc atctgtagga    60
gaccgggtca ccatcacttg tagatcc    87

<210> SEQ ID NO 41
<211> LENGTH: 90
<212> TYPE: DNA
<213> ORGANISM: Artificial Sequence
<220> FEATURE:
<223> OTHER INFORMATION: 5/44gL1 T2

<400> SEQUENCE: 41
tatctgcaca aaccaggtaa agccccacaa ttgctcatct acggaatctc taacagattt    60
agtggtgtac cagacaggtt cagcggttcc    90

<210> SEQ ID NO 42
<211> LENGTH: 91
<212> TYPE: DNA
<213> ORGANISM: Artificial Sequence
<220> FEATURE:
<223> OTHER INFORMATION: 5/44gL1 T3

<400> SEQUENCE: 42
agatttcgcc acttattact gtttacaagg tacacatcag ccgtacacat tcggtcaggg    60
tactaaagta gaaatcaaac gtacggcgtg c    91

<210> SEQ ID NO 43
<211> LENGTH: 88
<212> TYPE: DNA
<213> ORGANISM: Artificial Sequence
<220> FEATURE:
<223> OTHER INFORMATION: 5/44gL1 B1

<400> SEQUENCE: 43
gaacgtcacc ccgggaagca ggaatccaga acaacagaag caccaacagc ctaacaggca    60
acttcatggt ggcggcttcg aatcatcc    88

<210> SEQ ID NO 44
<211> LENGTH: 88
<212> TYPE: DNA
<213> ORGANISM: Artificial Sequence
<220> FEATURE:
<223> OTHER INFORMATION: 5/44gL1 B2

<400> SEQUENCE: 44
ctttacctgg tttgtgcaga taccaagaca aaaggtgtt cccataactg tttgcaagac    60
tctgactgga tctacaagtg atggtgac    88

<210> SEQ ID NO 45
<211> LENGTH: 90
<212> TYPE: DNA
<213> ORGANISM: Artificial Sequence
<220> FEATURE:
<223> OTHER INFORMATION: 5/44gL1 B3

<400> SEQUENCE: 45
aacagtaata agtggcgaaa tcttctggct ggagagacga gatcgtgagg gtgaaatcag    60
taccacttcc ggaaccgctg aacctgtctg    90

<210> SEQ ID NO 46

<211> LENGTH: 20
<212> TYPE: DNA
<213> ORGANISM: Artificial Sequence
<220> FEATURE:
<223> OTHER INFORMATION: 5/44gL1 F1

<400> SEQUENCE: 46
ggatgattcg aagccgccac                                                    20

<210> SEQ ID NO 47
<211> LENGTH: 21
<212> TYPE: DNA
<213> ORGANISM: Artificial Sequence
<220> FEATURE:
<223> OTHER INFORMATION: 5/44gL1 R1

<400> SEQUENCE: 47
gcacgccgta cgtttgattt c                                                  21

<210> SEQ ID NO 48
<211> LENGTH: 339
<212> TYPE: DNA
<213> ORGANISM: Mus musculus
<220> FEATURE:
<223> OTHER INFORMATION: DNA coding strand for mouse monoclonal 5/44 VL
      domain

<400> SEQUENCE: 48
gatgttgtgg tgactcaaac tccactctcc ctgcctgtca gctttggaga tcaagtttct         60
atctcttgca ggtctagtca gagtcttgca acagttatg gaacaccctt tttgtcttgg        120
tacctgcaca gcctggcca gtctccacag ctcctcatct atgggatttc aacagattt         180 tctggggtgc cagacaggtt cactggcagt ggttcaggga cagatttcac actcaagatc       240
agcacaataa agcctgagga cttgggaatg tattactgct acaaggtac acatcagccg        300 tacacgttcg gaggggggac caagctggaa ataaaacgt                              339

<210> SEQ ID NO 49
<211> LENGTH: 363
<212> TYPE: DNA
<213> ORGANISM: Mus musculus
<220> FEATURE:
<223> OTHER INFORMATION: DNA coding strand for mouse monoclonal 5/44 VH
      domain

<400> SEQUENCE: 49
gaggtccaac tgcagcagtc tgggactgta ctggcaaggc ctggggcttc cgtgaagatg         60
tcctgcaagg cttctggcta caggtttacc aactactgga ttcactgggt aaaacagagg       120
cctgggcagg gtctagaatg gattggtggt attaatcctg gaaataatta tactacgtat       180
aagaggaact tgaagggcaa ggccacactg actgcagtca catccgccag cactgcctac       240
atggacctca gcagcctgac aagtgaggac tctgcggtct attactgtac aagagagggc       300
tatggtaact acggggcctg gtttgcttac tggggccagg ggactctggt caccgtctcc       360
tca                                                                    363

<210> SEQ ID NO 50
<211> LENGTH: 9
<212> TYPE: DNA
<213> ORGANISM: Artificial Sequence
<220> FEATURE:
<223> OTHER INFORMATION: Sequence within oligonucleotide primer

<400> SEQUENCE: 50

```
gccgccacc                                                             9

<210> SEQ ID NO 51
<211> LENGTH: 101
<212> TYPE: DNA
<213> ORGANISM: Artificial Sequence
<220> FEATURE:
<223> OTHER INFORMATION: 5' oligonucleotide primer

<400> SEQUENCE: 51
gcgcgcaagc ttgccgccac catggacttc ggattctctc tcgtgttcct ggcactcatt    60
ctcaagggag tgcagtgtga ggtgcagctc gtcgagtctg g                       101

<210> SEQ ID NO 52
<211> LENGTH: 339
<212> TYPE: DNA
<213> ORGANISM: Mus musculus
<220> FEATURE:
<223> OTHER INFORMATION: DNA noncoding strand for mouse monoclonal 5/44
      VL domain

<400> SEQUENCE: 52
ctacaacacc actgagtttg aggtgagagg gacggacagt cgaaacctct agttcaaaga    60
tagagaacgt ccagatcagt ctcagaacgt ttgtcaatac ccttgtggaa aaacagaacc   120
atggacgtgt tcggaccggt cagaggtgtc gaggagtaga taccctaaag gttgtctaaa   180
agaccccacg gtctgtccaa gtgaccgtca ccaagtccct gtctaaagtg tgagttctag   240
tcgtgttatt tcggactcct gaacccttac ataatgacga atgttccatg tgtagtcggc   300
atgtgcaagc tcccccctg gttcgacctt tattttgca                           339

<210> SEQ ID NO 53
<211> LENGTH: 363
<212> TYPE: DNA
<213> ORGANISM: Mus musculus
<220> FEATURE:
<223> OTHER INFORMATION: DNA noncoding strand for mouse monoclonal 5/44
      VH domain

<400> SEQUENCE: 53
ctccaggttg acgtcgtcag accctgacat gaccgttccg gaccccgaag gcacttctac    60
aggacgttcc gaagaccgat gtccaaatgg ttgatgacct aagtgaccca ttttgtctcc   120
ggacccgtcc cagatcttac ctaaccacca taattaggac ctttattaat atgatgcata   180
ttctccttga acttcccgtt ccggtgtgac tgacgtcagt gtaggcggtc gtgacggatg   240
tacctggagt cgtcggactg ttcactcctg agacgccaga taatgacatg ttctctcccg   300
ataccattga tgccccggac caaacgaatg acccggtcc cctgagacca gtggcagagg    360
agt                                                                 363

<210> SEQ ID NO 54
<211> LENGTH: 110
<212> TYPE: DNA
<213> ORGANISM: Artificial Sequence
<220> FEATURE:
<223> OTHER INFORMATION: gH4 oligonucleotide

<400> SEQUENCE: 54
ccgggaataa ctacgctaca tataggagaa atctaaaggg cagagcaacg ctgaccgcct    60
tattgatgcg atgtatatcc tctttagatt tcccgtctcg ttgcgactgg              110
```

<210> SEQ ID NO 55
<211> LENGTH: 20
<212> TYPE: PRT
<213> ORGANISM: Artificial Sequence
<220> FEATURE:
<223> OTHER INFORMATION: gH4 graft

<400> SEQUENCE: 55

Pro Gly Asn Asn Tyr Ala Thr Tyr Arg Arg Asn Leu Lys Gly Arg Ala
1               5                   10                  15

Thr Leu Thr Ala
            20

<210> SEQ ID NO 56
<211> LENGTH: 109
<212> TYPE: DNA
<213> ORGANISM: Artificial Sequence
<220> FEATURE:
<223> OTHER INFORMATION: gH5 oligonucleotide

<400> SEQUENCE: 56
ccgggaataa ctacgctaca tataggagaa atctaaaggg cagagttacg atgaccgcct    60
tattgatgcg atgtatatcc tctttagatt tcccgtctca atgctactg              109

<210> SEQ ID NO 57
<211> LENGTH: 20
<212> TYPE: PRT
<213> ORGANISM: Artificial Sequence
<220> FEATURE:
<223> OTHER INFORMATION: gH5 graft

<400> SEQUENCE: 57

Pro Gly Asn Asn Tyr Ala Thr Tyr Arg Arg Lys Phe Gln Gly Arg Val
1               5                   10                  15

Thr Met Thr Ala
            20

<210> SEQ ID NO 58
<211> LENGTH: 110
<212> TYPE: DNA
<213> ORGANISM: Artificial Sequence
<220> FEATURE:
<223> OTHER INFORMATION: gH6 oligonucleotide

<400> SEQUENCE: 58
ccgggaataa ctacgctaca tataggagaa aattccaggg cagagcaacg ctgaccgcct    60
tattgatgcg atgtatatcc tcttttaagg tcccgtctcg ttgcgactgg              110

<210> SEQ ID NO 59
<211> LENGTH: 20
<212> TYPE: PRT
<213> ORGANISM: Artificial Sequence
<220> FEATURE:
<223> OTHER INFORMATION: gH6 graft

<400> SEQUENCE: 59

Pro Gly Asn Asn Tyr Ala Thr Tyr Arg Arg Lys Phe Gln Gly Arg Ala
1               5                   10                  15

Thr Leu Thr Ala
            20

<210> SEQ ID NO 60
<211> LENGTH: 110

```
<212> TYPE: DNA
<213> ORGANISM: Artificial Sequence
<220> FEATURE:
<223> OTHER INFORMATION: gH7 oligonucleotide

<400> SEQUENCE: 60
ccgggaataa ctacgctaca taggagaa aattccaggg cagagttacg atgaccgcct       60
tattgatgcg atgtatatcc tcttttaagg tcccgtctca atgctactgg              110

<210> SEQ ID NO 61
<211> LENGTH: 20
<212> TYPE: PRT
<213> ORGANISM: Artificial Sequence
<220> FEATURE:
<223> OTHER INFORMATION: gH7 graft

<400> SEQUENCE: 61

Pro Gly Asn Asn Tyr Ala Thr Tyr Arg Arg Lys Phe Gln Gly Arg Val
1               5                  10                  15

Thr Met Thr Ala
            20

<210> SEQ ID NO 62
<211> LENGTH: 123
<212> TYPE: DNA
<213> ORGANISM: Artificial Sequence
<220> FEATURE:
<223> OTHER INFORMATION: gL2 oligonucleotide

<400> SEQUENCE: 62
ccggggtgac gttgtcgtga cccagagccc atccagcctg agcgcatctg taggagaccg      60
gccactgcaa cagcactggg tctcgggtag gtcggactcg cgtagacatc ctctggccca    120
gtg                                                                  123

<210> SEQ ID NO 63
<211> LENGTH: 22
<212> TYPE: PRT
<213> ORGANISM: Artificial Sequence
<220> FEATURE:
<223> OTHER INFORMATION: gL2 graft

<400> SEQUENCE: 63

Ser Arg Gly Asp Val Val Val Thr Gln Ser Pro Ser Ser Leu Ser Ala
1               5                  10                  15

Ser Val Gly Asp Arg Val
            20

<210> SEQ ID NO 64
<211> LENGTH: 781
<212> TYPE: DNA
<213> ORGANISM: Artificial Sequence
<220> FEATURE:
<223> OTHER INFORMATION: DNA noncoding strand for g5/44 light chain

<400> SEQUENCE: 64
aagcttcggc ggtggtactt caacggacaa tccgacaaacc acgaagacaa caagacctaa    60
ggacgaaggg ccccactgca agttcactgg gtctcgggta ggtcggactc gcgtagacat   120
cctctggccc agtggtagtg aacatctagg tcagtctcag aacgtttgtc aataccttg     180 tggaaaaaca gaaccataga cgtgtttggt ccatttcggg gtgttaacga gtagatgcct   240
tagagattgt ctaaatcacc acatggtctg tccaagtcgc caaggccttc accatgacta   300
```

```
aagtgggagt gctagagcag agaggtcggt cttctaaagc ggtgaataat gacaaatgtt      360
ccatgtgtag tcggcatgtg taagccagtc ccatgatttc atctttagtt tgcatgccat      420
cgccggggta gacagaagta aagggcggt  agactactcg tcaactttag accttgacgg      480
agacaacaca cggacgactt attgaagata gggtctctcc ggtttcatgt caccttccac      540
ctattgcggg aggttagccc attgagggtc ctctcacagt gtctcgtcct gtcgttcctg      600
tcgtggatgt cggagtcgtc gtgggactgc gactcgtttc gtctgatgct ctttgtgttt      660
cagatgcgga cgcttcagtg ggtagtcccg gactcgagcg ggcagtgttt ctcgaagttg      720 tccctctca  caatctccct cttcacgggg gtggacgagg agtcaaggtc ggacccttaa      780
g                                                                     781

<210> SEQ ID NO 65
<211> LENGTH: 2160
<212> TYPE: DNA
<213> ORGANISM: Artificial Sequence
<220> FEATURE:
<223> OTHER INFORMATION: DNA noncoding strand for g5/44 heavy chain

<400> SEQUENCE: 65
ttcgaacggc ggtggtacct gaagcctaag agagagcaca aggaccgtga gtaagagttc       60
cctcacgtca cactccacgt taaccaggtc agtcctcgtc tccaattctt cggaccacga      120
aggcagtttc aaagcacatt ccgatcgccg atgtccaagt gtttaataac ctaagtaacc      180
cagtccgtcc gaggccctgt tccggacctt acctagccac cgtaattagg gcccttattg      240
atgcgatgta tatcctcttt taaggtcccg tctcaatgct actggcgcct gtggaggtgt      300
tcgtgacaga tgtacctcga cagtagagac tctaggctcc tgtggcgtca catgataaca      360
tgatctcttc cgatgccatt aatgcctcgg accaagcgga tgaccccggt cccatgggat      420
cagtgtcaga ggagtcgaag atgtttcccg ggtaggcaga aggggaccg  cgggacgagg      480 tcctcgtgga ggctctcgtg tcggcggac  ccgacggacc agttcctgat gaagggcttt      540
ggccactgcc acagcacctt gagtccgcgg gactggtcgc cgcacgtgtg aagggccga     600 caggatgtca ggagtcctga gatgaggag  tcgtcgcacc actggcacgg gaggtcgtcg      660
aacccgtgct tctggatgtg gacgttgcat ctagtgttcg ggtcgttgtg gttccacctg      720
ttctctcaac cactctccgg tcgtgtccct ccctcccaca gacgaccttc ggtccgagtc      780
gggaggacgg acctgcgtgg ggccgacacg tcgggtcgg  gtcccgtcgt tccgtacggg      840
gtagacagag gagtgggcct ccggagactg gtggggtgag tacgggtccc tctcccagaa      900
gacctaaaaa ggtggtccga ggcccgtcgg tgtccgacct acggggatgg ggtccgggac      960
gcgtatgtcc ccgtccacga cgcgagtctg gacggttctc ggtataggcc tcctgggac     1020 ggggactgga ttcggttggg gtttccggtt tgagaggtga gggagtcgag tctgtggaag     1080
agaggagggt ctagactcat tgagggttag aagagagacg tctcaggttt ataccagggg     1140
gtacgggtgg tacgggtcca ttcggttggg tccggagcgg gaggtcgagt tccgccctgt     1200
ccacgggatc tcatcggacg taggtccctg tccggggtcg gcccacgact gcgtaggtgg     1260
aggtagagaa ggagtcgtgg actcaaggac cccctggta  gtcagaagga caggggggt     1320 tttgggttcc tgtgagagta ctagagggcc tggggactcc agtgcacgca ccaccacctg     1380
cactcggtcc ttctggggct ccaggtcaag ttgaccatgc acctaccgca cctccacgta     1440
ttacggttct gtttcggcgc cctcctcgtc aagttgtcgt gcatggcaca ccagtcgcag     1500
gagtggcagg acgtggtcct gaccgacttg ccgttcctca tgttcacgtt ccagaggttg     1560
```

```
tttccggagg gcaggaggta gctcttttgg tagaggtttc ggtttccacc ctgggtgccc    1620
cacgctcccg gtgtacctgt ctccagtcga gccgggtggg agacgggacc ctcactggcg    1680
acacggttgg agacagggat gtcccgtcgg ggctctcggt gtccacatgt gggacggggg    1740
tagggtcctc ctctactggt tcttggtcca gtcggactgg acggaccagt ttccgaagat    1800
ggggtcgctg tagcggcacc tcaccctctc gttacccgtc ggcctcttgt tgatgttctg    1860
gtgcggaggg cacgacctga ggctgccgag gaagaaggag atgtcgtccg attggcacct    1920
gttctcgtcc accgtcctcc ccttacagaa gagtacgagg cactacgtac tccgagacgt    1980
gttggtgatg tgtgtcttct cggagaggga cagagaccca tttactcacg gtcccggccg    2040
ttcgggggcg aggggcccga gagcccccagc gcgctcctac gaaccgtgca tggggcagat    2100
gtatgaaggg tccgtgggtc gtacctttat ttcgtgggtg gtgacgggac cgagcttaag    2160
```

What is claimed is:

1. A composition comprising monomeric calicheamicin derivative/anti-CD22 antibody conjugates with reduced low conjugated fraction and having the formula, Pr(—X—W)m, wherein:
Pr is an anti-CD22 antibody and comprises SEQ ID NO: 1 for CDR-H1, SEQ ID NO: 2 or SEQ ID NO: 13 or SEQ ID NO: 15 or SEQ ID NO: 16 or residues 50-66 of SEQ ID NO: 23 or residues 50-66 of SEQ ID NO: 27 for CDR-H2, SEQ ID NO: 3 for CDR-H3, SEQ ID NO: 4 for CDR-L1, SEQ ID NO: 5 for CDR-L2 and SEQ ID NO: 6 for CDR-L3;
W is a calicheamicin derivative comprising a calicheamicin;
X is a hydrolyzable linker that links the anti-CD22 antibody to the calicheamicin derivative and that is capable of releasing the calicheamicin derivative from the calicheamicin derivative/anti-CD22 antibody conjugate after binding and entry into target cells;
m is the average loading for a purified conjugation product such that the calicheamicin constitutes 4-10% of the calicheamicin derivative/anti-CD22 antibody conjugate by weight; and
wherein the composition has a low conjugated fraction of less than 10%.

2. The composition of claim 1, wherein the antibody is an anti-CD22 antibody and comprises SEQ ID NO: 1 for CDR-H1, residues 50-66 of SEQ ID NO: 27 for CDR-H2, SEQ ID NO: 3 for CDR-H3, SEQ ID NO: 4 for CDR-L1, SEQ ID NO: 5 for CDR-L2 and SEQ ID NO: 6 for CDR-L3.

3. The composition of claim 1, wherein the antibody is an anti-CD22 antibody and comprises a light chain variable domain comprising SEQ ID NO: 19 and a heavy chain variable domain comprising SEQ ID NO: 27.

4. The composition of claim 1, wherein the antibody is an anti-CD22 antibody and comprises a light chain consisting of residues 21-239 of SEQ ID NO: 28 and a heavy chain consisting of residues 20-466 of SEQ ID NO: 30, and wherein the antibody is expressed in a mammalian cell.

5. The composition of claim 4, wherein the anti-CD22 antibody results from the expression of SEQ ID NO: 29 and SEQ ID NO: 31 in the mammalian cell.

6. The composition of claim 1, wherein the antibody is an anti-CD22 antibody and comprises a light chain comprising SEQ ID NO: 28 and a heavy chain comprising SEQ ID NO: 30.

7. The composition of claim 1, wherein the antibody is selected from a group consisting of a monoclonal antibody, a chimeric antibody, a human antibody, a humanized antibody, a single chain antibody, and a biologically active antibody fragment wherein the biologically active fragment is a Fab, a modified Fab, Fab', F(ab')$_2$ or Fv, or a heavy chain monomer or dimer.

8. The composition of claim 7, wherein the antibody is a humanized antibody.

9. The composition of claim 8, wherein the humanized antibody is a CDR-grafted antibody.

10. The composition of claim 2, wherein the anti-CD22 antibody comprises a variable domain comprising human acceptor framework regions.

11. The composition of claim 10, wherein the variable domain is a heavy chain variable domain comprising a heavy chain framework region comprising donor residues at positions 1, 28, 48, 72, and 97 of SEQ ID NO: 8 occupied by Glu, Arg, Ile, Ala, and Thr, respectively, wherein the remainder of the heavy chain framework region is occupied by corresponding residues of the human acceptor framework of SEQ ID NOs: 21 or 22.

12. The composition of claim 11, wherein the heavy chain variable domain comprises SEQ ID NO: 27.

13. The composition of claim 10, wherein the variable domain is a heavy chain variable domain comprising a heavy chain framework region comprising donor residues at positions 1, 28, 48, 68, 70, 72 and 97 of SEQ ID NO: 8 occupied by Glu, Arg, Ile, Ala, Leu, Ala, and Thr, respectively, wherein the remainder of the heavy chain framework region is occupied by corresponding residues of the human acceptor framework of SEQ ID NOs: 21 or 22.

14. The composition of claim 10, wherein the variable domain is a light chain variable domain comprising a light chain framework region comprising donor residues at positions 2, 4, 42, 43, 50, and 65 of SEQ ID NO: 7 occupied by Val, Val, Leu, His, Gln, and Asp, respectively, wherein the remainder of the light chain framework region is occupied by corresponding residues of the human acceptor framework of SEQ ID NOs: 17 or 18.

15. The composition of claim 2, wherein the light chain variable domain comprises SEQ ID NO: 19.

16. The composition of claim 10, wherein the variable domain is a light chain variable domain comprising a light chain framework region comprising donor residues at positions 2, 3, 4, 42, 43, 50 and 65 of SEQ ID NO: 7 occupied by Val, Val, Val, Leu, His, Gln, and Asp, respectively, wherein the remainder of the light chain framework region is occupied by corresponding residues of the human acceptor framework of SEQ ID NOs: 17 or 18.

17. The composition of claim 11, further comprising a light chain variable domain comprising a light chain framework region comprising donor residues at positions 2, 4, 42, 43, 50, and 65 of SEQ ID NO: 7 occupied by Val, Val, Leu, His, Gln, and Asp, respectively, wherein the remainder of the light chain framework region is occupied by corresponding residues of the human acceptor framework of SEQ ID NOs: 17 or 18.

18. The composition of claim 17, wherein the light chain variable domain comprises SEQ ID NO: 19.

19. The composition of claim 12, further comprising a light chain variable domain comprising a light chain framework region comprising donor residues at positions 2, 4, 42, 43, 50, and 65 of SEQ ID NO: 7 occupied by Val, Val, Leu, His, Gln, and Asp, respectively, wherein the remainder of the light chain framework region is occupied by corresponding residues of the human acceptor framework of SEQ ID NOs: 17 or 18.

20. The composition of claim 19, wherein the light chain variable domain comprises SEQ ID NO: 19.

21. The composition of claim 20, wherein the anti-CD22 antibody comprises a light chain consisting of residues 21-239 of SEQ ID NO: 28 and a heavy chain consisting of residues 20-466 of SEQ ID NO: 30, and wherein the antibody is expressed in a mammalian cell.

22. The composition of claim 21, wherein the anti-CD22 antibody results from the expression of SEQ ID NO: 29 and SEQ ID NO: 31 in the mammalian cell.

23. The composition of claim 1, wherein the calicheamicin is gamma calicheamicin or N-acetyl gamma calicheamicin.

24. The composition of claim 1, wherein the calicheamicin is functionalized with 3-mercapto-3-methyl butanoyl hydrazide.

25. The composition of claim 24, wherein the hydrolyzable linker comprises 4-(4-acetylphenoxy) butanoic acid (AcBut).

26. A lyophilized composition comprising the composition of claim 1 prepared by:
    (a) dissolving the composition of claim 1 to a final concentration of 0.5 to 2 mg/mL in a solution comprising a cryoprotectant at a concentration of 1.5%-5% by weight, a polymeric bulking agent at a concentration of 0.5-1.5% by weight, electrolytes at a concentration of 0.01M to 0.1M, a solubility facilitating agent at a concentration of 0.005-0.05% by weight, buffering agent at a concentration of 5-50 mM such that the final pH of the solution is 7.8-8.2, and water;
    (b) dispensing the above solution into vials at a temperature of +5° C. to +10° C.;
    (c) freezing the solution at a freezing temperature of −35° C. to −50° C.;
    (d) subjecting the frozen solution to an initial freeze drying step at a primary drying pressure of 20 to 80 microns at a shelf-temperature at −10° C. to −40° C. for 24 to 78 hours; and
    (e) subjecting the freeze-dried product of step (d) to a secondary drying step at a drying pressure of 20 to 80 microns at a shelf temperature of +10° C. to +35° C. for 15 to 30 hours.

27. The lyophilized composition of claim 26, wherein the cryoprotectant is selected from a group comprising alditol, mannitol, sorbitol, inositol, polyethylene glycol, aldonic acid, uronic acid, aldaric acid, aldoses, ketoses, amino sugars, glyceraldehydes, arabinose, lyxose, pentose, ribose, xylose, galactose, glucose, hexose, idose, mannose, talose, heptose, fructose, gluconic acid, lactose, methyl α-glucopyranoside, maltose, isoascorbic acid, ascorbic acid, lactone, sorbose, glucaric acid, erythrose, threose, allose, altrose, gulose, talose, erythrulose, ribose, xylulose, psicose, tagatose, glucuronic acid, galacturonic acid, mannuronic acid, glucosamine, galactosamine, sucrose, trehalose, neuraminic acid, arabinans, fructans, fucans, galactans, galacturonans, glucans, mannans, xylans, levan, fucoidan, carrageenan, galactocarolose, pectins, pectic acids, amylose, pullulan, glycogen, amylopectin, cellulose, dextran, pustulan, chitin, agarose, keratin, chondroitin, dermatan, hyaluronic acid, alginic acid, xanthan gum, starch, ethylene glycol, polyethylene glycol, polypropylene glycol, glycerol, and pentaerythritol.

28. The lyophilized composition of claim 27, wherein the cryoprotectant is sucrose.

29. The lyophilized composition of claim 28, wherein the sucrose is present at a concentration of 1.5% by weight.

30. The lyophilized composition of claim 26, wherein the polymeric bulking agent is Dextran 40, and is at a concentration of 0.9% by weight.

31. The lyophilized composition of claim 26, wherein the polymeric bulking agent is hydroxyethyl starch 40, and is at a concentration of 0.9% by weight.

32. The lyophilized composition of claim 26, wherein the electrolyte is sodium chloride, and is present at a concentration of 0.05 M.

33. The lyophilized composition of claim 26, wherein the solubility facilitating agent is a surfactant.

34. The lyophilized composition of claim 26, wherein the surfactant is polysorbate 80, and is present at a concentration of 0.01% by weight.

35. The lyophilized composition of claim 26, wherein the buffering agent is tromethamine, and is present at a concentration of 0.02 M.

36. The lyophilized composition of claim 26, wherein the pH of the solution of step (a) is 8.0.

37. The lyophilized composition of claim 26, wherein the solution in step (b) is dispensed into vials at a temperature of +5° C.

38. The lyophilized composition of claim 26, wherein in step (c) the freezing of the solution in the vials is carried out at a freezing temperature of −45° C.

39. The lyophilized composition of claim 26, wherein in step (d) the frozen solution is subjected to an initial freeze drying step at a primary drying pressure of 60 microns and at a shelf temperature of −30° C. for 60 hours.

40. The lyophilized composition of claim 39, wherein in step (e), the freeze-dried product of step (d) is subjected to a secondary drying step at a drying pressure of 60 microns at a shelf temperature of +25° C. for 24 hours.

* * * * *

UNITED STATES PATENT AND TRADEMARK OFFICE
CERTIFICATE OF CORRECTION

PATENT NO. : 8,835,611 B2
APPLICATION NO. : 13/372172
DATED : September 16, 2014
INVENTOR(S) : Arthur Kunz et al.

Page 1 of 1

It is certified that error appears in the above-identified patent and that said Letters Patent is hereby corrected as shown below:

In the Claims

Column 92, lines 5-22, cancel the text of claim 27 and insert the following claim:

--27. The lyophilized composition of claim 26, wherein the cryoprotectant is selected from the group consisting of alditol, mannitol, sorbitol, inositol, polyethylene glycol, aldonic acid, uronic acid, aldaric acid, aldoses, ketoses, amino sugars, glyceraldehydes, arabinose, lyxose, pentose, ribose, xylose, galactose, glucose, hexose, idose, mannose, talose, heptose, fructose, gluconic acid, lactose, methyl a–glucopyranoside, maltose, isoascorbic acid, ascorbic acid, lactone, sorbose, glucaric acid, erythrose, threose, allose, altrose, gulose, talose, erythrulose, ribose, xylulose, psicose, tagatose, glucuronic acid, galacturonic acid, mannuronic acid, glucosamine, galactosamine, sucrose, trehalose, neuraminic acid, arabinans, fructans, fucans, galactans, galacturonans, glucans, mannans, xylans, levan, fucoidan, carrageenan, galactocarolose, pectins, pectic acids, amylose, pullulan, glycogen, amylopectin, cellulose, dextran, pustulan, chitin, agarose, keratin, chondroitin, dermatan, hyaluronic acid, alginic acid, xanthan gum, starch, ethylene glycol, polyethylene glycol, polypropylene glycol, glycerol, and pentaerythritol.--

Signed and Sealed this
Eighth Day of September, 2015

Michelle K. Lee
*Director of the United States Patent and Trademark Office*